US006953680B2

(12) United States Patent
Fuller et al.

(10) Patent No.: US 6,953,680 B2
(45) Date of Patent: Oct. 11, 2005

(54) MITOFUSINS, FZO HOMOLOGS AND FUNCTIONAL DERIVATIVES THEREOF

(75) Inventors: Margaret T. Fuller, Stanford, CA (US); Karen G. Hales, Davidson, NC (US); Ansgar H. Santel, Berlin (DE)

(73) Assignee: The Board of Trustees of the Leland Stanford, Junior University, Palo Alto, CA (US)

( * ) Notice: Subject to any disclaimer, the term of this patent is extended or adjusted under 35 U.S.C. 154(b) by 66 days.

(21) Appl. No.: 10/117,846

(22) Filed: Apr. 5, 2002

(65) Prior Publication Data

US 2002/0168673 A1 Nov. 14, 2002

Related U.S. Application Data

(63) Continuation-in-part of application No. PCT/US00/27871, filed on Oct. 6, 2000, which is a continuation-in-part of application No. 09/413,285, filed on Oct. 6, 1999, now abandoned.

(51) Int. Cl.$^7$ .............................. C12N 9/00; C12N 9/10; C07H 21/04
(52) U.S. Cl. ............................... 435/193; 435/4; 435/6; 435/69.1; 435/183; 435/252.3; 435/320.1; 536/23.2; 536/23.4; 536/23.5; 536/23.7; 530/350
(58) Field of Search ............................... 435/4, 6, 69.1, 435/183, 193, 252.3, 320.1, 194, 325; 536/23.2–23.7; 530/350

(56) References Cited

U.S. PATENT DOCUMENTS 6,284,507 B1 * 9/2001 Fuller et al.

FOREIGN PATENT DOCUMENTS

WO          95/06764          3/1995

OTHER PUBLICATIONS

Nagase et al. (DNA Res. 1996, vol. 3(5) :321–329).*
Lodes et al. GenBank Accession No. AX321223, Dec. 15, 2001.*
Kawabata A et al. GenBank Accession No. AK000700, Feb. 22, 2000.*
PIR Database accession No. S41785, Dwivedi et al. dated Sep. 10, 1994.*
SPTREMBL Database accession No. Q23424, Wilson et al. dated Nov. 1, 1996.*
Chen et al., Rattus Norvegicus Hypertension–Related Protein MRNA, Complete CDS, EMBL, 1996, abstract.

Hales et al., A Novel Transmembrane GTPASE is Required for Developmentally Regulated Mitochondrial Fusion During *Drosophila* Spermatogenesis, Molecular Biology of the Cell, 1996, 7: 615A.
Hales et al., Developmentally Regulated Mitochondrial Fusion Mediated by a Conserved, Novel, Predicted GTPASE, Cell, 1997, 90: 121–129.
Nagase et al., Prediction of the Coding Sequences of Unidentified Human Genes. VI. The Coding Sequences of 80 New Genes (KIAA0201–KIAA0280) Deduced by Analysis of CDNA Clones from Cell Line KG–1 and Brain, DNA Research, 1996, 3: 321–329.
Bashkin, James K., et al., "Robozyme Mimics as Catalytic Antisense Reagents," *Applied Biochemistry and Biotechnology* (1995) vol. 54:43–56.
Furth, Priscilla A., et al., "Gene Transfer Into Somatic Tissues By Jet Injection," *Analytical Biochemistry* (1992) vol. 205: 365–368.
Kawano, Shigeyuki, et al., "Sexuality Of Mitochondra: Fusion, Recombination, and Plasmids," *International Review of Cytology* (1995) vol. 161:49–110.
Larsson, Nils–Göran, et al., "Molecular Genetic Aspects Of Human Mitochomdrial Disorders," *Annu. Rev. Genetics* (1995) vol. 29:151–178.
Tang, De–chu, et al., "Genetic Immunization Is A Simple Method For Eliciting An Immune Response," *Nature* (Mar. 12, 1992) vol. 356:152–154.
Wagner, Richard W., et al., "Potent and Selective Inhibition Of Gene Expresion By An Antisense Heptanucleotide," *Nature Biotechnology* (Jul. 1996) vol. 14:840–844.
The 1992 Sigma Catalog, Published by Sigma Chemical Company, Jan. 1, 1992, see p. 62, product #A7627.

* cited by examiner

*Primary Examiner*—Manjunath N. Rao
(74) *Attorney, Agent, or Firm*—Pamela J. Sherwood; Bozicevic, Field & Francis LLP

(57) ABSTRACT

Mitofusin genes and encoded polypeptides are provided, including the *Drosophila* Fzo protein and its homologs from insects, other invertebrates, yeast, and vertebrates including mouse and humans. Mitofusins are large predicted GTPases with a predicted trans-membrane domain, coiled-coil regions, and a C-terminal region showing a high pI. The mitofusins are the first known protein mediator of mitochondrial fusion, and mediate developmentally regulated post-meiotic fusion of mitochondria. Missense mutations that alter conserved residues required for GTP binding in other GTPases inhibit the in vivo fusogenic activity of Fzo but do not affect its localization. Fusion proteins having amino acid sequences from mitofusin transmembrane regions localize to mitochondria. Mitofusins may be used in methods of identifying anti-insect and antifungal agents. Functional derivatives of mitofusins useful for such methods are described.

8 Claims, No Drawings

MITOFUSINS, FZO HOMOLOGS AND FUNCTIONAL DERIVATIVES THEREOF

Accumulation of mutations in the mitochondrial genome has been proposed as an important contributor to aging and degenerative diseases. In several cases human mitochondrial disorders have been shown to be caused by mutations or deletions of mitochondrial DNA (for a review, see Larsson et al., 1995, *Ann. Rev. Genet.* 29:151–178). In addition, mitochondria have been implicated in the mechanism of programmed cell death.

There is evidence for defects in energy metabolism, excitotoxicity, and for oxidative damage in the etiology of neurodegenerative diseases, including amyotrophic lateral sclerosis, Huntington's disease, Parkinson's disease, and Alzheimer's disease. It is likely that there is a complex interplay between these mechanisms. Mitochondrial DNA is particularly susceptible to oxidative stress, and there is evidence of age-dependent damage and deterioration of respiratory enzyme activities with normal aging. This may contribute to the delayed onset and age dependence of neurodegenerative diseases.

Mitochondria are dynamic organelles that undergo regulated fusion in many cell types (for reviews, see Kawano et al., 1995, *Int. Rev. Cytol,* 161:49–110, and Bereiter-Hahn et al., 1994, *Microscop. Res. Technique* 27:198–219). Analysis of serial sections from rodent skeletal muscle, lymphocytes, liver, spinal ganglion cells, and from the yeast *Saccharomyces cerevisiae* has shown that all the mitochondrial material of a cell can exist as a giant branched reticulum.

Specific protein mediators that act as biomechanical triggers and/or regulate specificity and timing of membrane fusion events have been identified in a wide variety of other cellular and subcellular contexts. The best characterized biomechanically acting fusogen is influenza virus hemagglutinin (HA) that mediates fusion of endocytosed viruses to cells. Regions resembling the HA fusion peptide exist in the ADAM family proteins, which are implicated in sperm/egg and myoblast fusion.

The identification of protein mediators of mitochondrial fusion and their possible role in maintenance of mitochondrial structure, function and genomic integrity is of great interest for diagnosis, drug screening and potential therapeutic strategies, including targeted delivery of genes, proteins and molecules to existing mitochondria. If recombination between differently mutated mitochondrial DNA molecules allows restoration of a functional copy, the ability of mitochondria to fuse may play an important role in maintenance of mitochondrial genomes. Alternatively, fusion of mitochondria may allow complementation between two mutations in different genes in the mitochondrial genome, allowing restoration of mitochondrial function even in the absence of recombination.

SUMMARY OF THE INVENTION

Mitofusin genes and proteins, various functional derivatives thereof, and their nucleotide and amino acid sequences, are provided. As used herein, the term "mitofusin" indicates the *Drosophila* Fzo protein or any of its homologues from insects, other invertebrates, yeast, and vertebrates including mouse and humans. Mitofusins are large predicted GTPases with a predicted trans-membrane domain, coiled-coil regions, and a C-terminal region showing a high isoelectric point (pI) and a predicted coiled-coil region. The mitofusins are the first known protein mediators of mitochondrial fusion, e.g. mediating developmentally regulated post-meiotic fusion of mitochondria in *Drosophila* spermatids.

In one embodiment of the invention, the mitofusin is a Mfn2 mitofusin, e.g. comprising the amino acid sequence as set forth in any one of SEQ ID NO:4; 10; or 16. In another embodiment of the invention, the mitofusin is a mammalian mitofusin, e.g. comprising the amino acid sequence set forth in any one of SEQ ID NO:6; 8; 10; 14; or 16. The human mitofusin family has been found to comprise the nucleic acid sequences as set forth in SEQ ID NO:5; 7; 9; 11; and 12.

DESCRIPTION OF THE SPECIFIC EMBODIMENTS

Mitofusin genes and proteins, various functional derivatives thereof, and their nucleotide and amino acid sequences, are provided. The mitofusin Fzo is the first known protein mediator of mitochondrial fusion. As used herein, the term "mitofusin" indicates the *Drosophila* Fzo protein or any of its homologs from cells or organisms possessing mitochondria including, byway of non-limiting example, mature and larval stages of insects such as, for example, flies, mosquitoes, butterflies, bees and moths; other invertebrates, such as, for example, worms; protozoa; yeast and other fungi; vertebrates, including birds (such as chickens and turkeys), amphibians such as frogs and salamanders, and mammals such as mice, cows, pigs, sheep, horses and humans.

The term "Fzo homolog" includes all mitofusins as well as homologs of the Fzo protein derived from cells or organisms that lack mitochondria, i.e., eubacteria and archaebacteria. Nucleic acids from different organisms, cells or tissues that encode Fzo homologs and mitofusins can be identified by those skilled in the art by a variety of methods, which may be combined.

Table of Sequences

| SEQ ID NO | Clone Name | Length | Type |
| --- | --- | --- | --- |
| 1 | dMfn1 | 2399 | DNA |
| 2 | dMfn1 | 718 | Protein |
| 3 | dMfn2 | 2501 | DNA |
| 4 | dMfn2 | 832 | Protein |
| 5 | hMfn1 | 2226 | DNA |
| 6 | hMfn1 | 741 | Protein |
| 7 | hMfn1 splice variant | 3148 | DNA |
| 8 | hMfn1 splice variant | 370 | Protein |
| 9 | hMfn2 | 4550 | DNA |
| 10 | hMfn2 | 757 | Protein |
| 11 | hMfn1 homolog | 1812 | DNA |
| 12 | hMfn1 homolog | 2465 | DNA |
| 13 | mMfn1 | 2220 | DNA |
| 14 | mMfn1 | 740 | Protein |
| 15 | mMfn2 | 2744 | DNA |
| 16 | mMfn2 | 758 | Protein |
| 17 | rMfn2 | 1986 | DNA |
| 18 | C. sacc. Mfn | 134 | Protein |
| 19 | yeast Mfn | 157 | Protein |
| 20 | worm Mfn | 163 | Protein |

One method involves detectably labeling a nucleic acid probe, which comprises all or a portion of the nucleic acids that encode Fzo homologs described herein, and hybridizing the detectably labeled probe to nucleic acids prepared from the cell, tissue or organism of interest and separated on the basis of size, charge, or other physical characteristics. A widely used method of separation involves electrophoresis of nucleic acids on agarose of polyacrylamide gels, followed by transfer of the electrophoresed nucleic acids to an appropriate filter such as, e.g., nitrocellulose. Under high stringency hybridization conditions, Fzo homologs having at least a 80% degree of similarity to the Fzo homologs described herein may be detected by hybridization analysis; under low stringency hybridization conditions, Fzo homologs having at least a 30% degree of similarity to the Fzo homologs described herein may be detected. A plurality of probes, derived from more than one of the Fzo homologs described herein, can be used to detect Fzo homologs having a low degree of similarity (e.g., less than about 50%) to the Fzo homologs herein disclosed. Once detected, nucleic acids encoding Fzo homologs may be further purified or amplified by methods known in the art, e.g., affinity purification or polymerase chain reaction (PCR).

Another method involves database searching and/or sequence comparisons using the nucleotide or amino acid sequences provided herein. As described in detail in the Examples, Fzo homologs and mitofusins comprise particular peptide motifs that can be identified by virtue of their having at least 75% identity, with no gaps, with various consensus sequences provided herein. By "having at least 75% identity, with no gaps," it is meant that an amino acid sequence in a Fzo homolog can be aligned, residue by residue, with a consensus amino acid sequence provided herein, without the need to introduce gaps in either of the sequences and with a minimum of 75% sequence identity. By way of example, consider a consensus sequence MVAFFGRTSNGKSTVINA (SEQ ID NO:15). An example of an amino acid sequence having at least 80% identity, with no gaps, with SEQ ID NO:21 is shown below as SEQ ID NO:22:

```
MVAFFGPTSNGKSTVINA        (SEQ ID NO:21)
|||||*|||||||*||||
MVAFFLPTSNGKSHVINA        (SEQ ID NO:22),
``` wherein straight lines ("|") indicate identical residues and asterisks ("*") indicate non-identical residues. In contrast, SEQ ID NO:23 does not have at least 75% identity, with no gaps, with the consensus sequence SEQ ID NO:21, because only about 72% (13 out of 18 residues) of the amino acid residues of SEQ ID NO:23 are identical to the consensus sequence when the two are aligned:

```
MVAFFGPTSNGKSTVINA        (SEQ ID NO:21)
||||**|*| *||*||:|
MVAFKLPHSNPKSHVINA        (SEQ ID NO:23).
```

Similarly, SEQ ID NO:24 does not have at least 75% identity, with no gaps, with the consensus sequence SEQ ID NO:21, because gaps (indicated as "–") must be introduced into one of the sequences in order to achieve this degree of identity when the two sequences are aligned:

```
MVAFFGRTSNGKSTVINA        (SEQ ID NO:21)
|||||  |||||  ||||||
MVAFF-RTSNG-STVINA        (SEQ ID NO:24).
```

Yet another method of identifying Fzo homologs involves preparing proteins en masse from a cell, tissue or organism of interest, separating them by, e.g., electrophoresis and transferring them to, e.g., a nitrocellulose membrane which is then probed using an antibody raised to a herein-described Fzo homolog or functional derivative (Western analysis). Antibodies specific for the consensus sequences of the invention are preferred. The antibodies bind Fzo homologs specifically or at least preferentially, and the proteins that are thereby identified may be extracted from a gel, and portions of their amino sequences determined, according to methods known in the art. The amino acid sequences so derived are used to design probes or PCR primers that can be used to isolate corresponding nucleic acids, or to prepare synthetic polypeptides that are used to immunize animals in order to produce antibodies having a high degree of specificity for the Fzo homolog of interest and which can be used to separate the Fzo homolog protein from other components in an extract by affinity purification techniques.

The provided mitofusin and Fzo homolog genes, and functional derivatives and fragments thereof (including genomic regulatory regions), have utility in the in vitro or in vivo production of mitofusin and Fzo homolog proteins, and functional derivatives and fragments thereof; as probes for the detection of nucleic acids encoding mitofusins, Fzo homologs and related gene products; and for the modulation of gene activity. Mitofusins, including human Mfn1 and Mfn2 proteins, localize to mitochondria and participate in a high-molecular weight, detergent extractable protein complexes. Over-expression of mitofusins in cells causes formation of characteristic networks of mitochondria.

The provided mitofusin and Fzo homolog proteins, and functional derivatives and fragments thereof, have utility in enhancing, modulating or inhibiting the activity of other mitofusins and Fzo homologs, such as those that are endogenous in a cell or organism; for enhancing, modulating or inhibiting the fusion of mitochondria, both in vivo and in vitro; as immunogens to raise specific antibodies; and in drug screening for compositions that mimic or modulate mitofusin activity or expression, including functional derivatives of mitofusin and Fzo homolog proteins.

The term "functional derivative" refers to a fragment, conjugate or mutant derived from a gene or protein of interest, or combinations thereof, wherein a "fragment" is an isolated nucleic acid or polypeptide, respectively, that is derived from the gene or protein of interest. A "mutant" is a gene or protein having a sequence in which one or more nucleotides or amino acid residues, respectively, has been altered relative to the sequence of gene or protein of interest, or a sequence wherein one or more nucleotides or amino acids have been inserted into or deleted from the sequence of gene or protein of interest. Such derivatives (a) retain one or more utilities, biochemical or biological functions of the gene or protein of interest or (b) are capable of enhancing, modulating or inhibiting one or more utilities, biochemical or biological functions of the gene or protein of interest.

Mutations of interest include amino acid changes in the GTPAse domain, i.e. amino acid substitutions in the characteristic GTPase motifs, or deletion or addition of amino acid residue elsewhere in the protein such as the C-terminal predicted coiled coil domain or internal mitochondrial targeting sequences. In some cases, loss of function is observed when mutations are introduced into one or more of these regions, e.g. a K to T substitution at amino acid residue 88 in the G1 motif of the GTPase domain in hMfn1. Substitutions in the analogous residue in the *Drosophila* Fzo and yeast Fzo 1p proteins also block mitochondrial fusion activity.

In other cases mutations result in a dominant negative phenotype eg, a, T to A substitution at amino acid residue 109 in the G2 motif of the GTPase domain in hMfn1. Such mutated constructs may be used to interfere with function of endogenous Mfn1 or Mfn2.

Fragments may be obtained directly, for example, by cleaving a gene with a restriction enzyme and isolating a specific restriction fragment derived from the gene, or indirectly, for example, by choosing a portion of the nucleotide sequence of a gene (or the amino acid sequence of a protein) and chemically synthesizing an oligonucleotide (or polypeptide) having that sequence.

For a protein, functional derivatives include but are not limited to synthetic polypeptides comprising an amino acid sequence derived from the protein of interest; mutant proteins, including dominant-negative mutants (Sheppard (1994) *Am. J. Respir. Cell. Mol. Biol.* 11:1–6); fusion proteins, a type of conjugate wherein a polypeptide having an amino acid sequence derived from the protein of interest is contiguous with one or more polypeptides having amino acid sequences derived from proteins other than the protein of interest; and other conjugates, such as those wherein the protein of interest or a fragment derived therefrom is structurally linked (chemically bonded) to one or more non-proteinaceous chemical moieties.

For a gene, functional derivatives include but are not limited to mutant nucleic acids; nucleic acids encoding fusion proteins; probes, including synthetic oligonucleotides such as PCR primers; antisense (reverse complement) nucleic acids, including ribozymes and synthetic oligonucleotides; molecular decoys, i.e., double-stranded nucleic acids capable of binding genetic regulatory factors by virtue of having a nucleotide sequence that is recognized by such factors; and conjugates, i.e., molecules wherein the gene of interest or a fragment derived therefrom is structurally linked (chemically bonded) to one or more chemical moieties, wherein such chemical moieties are not naturally occurring nucleic acids.

A "conjugate" is a gene, protein or fragment thereof that is chemically linked to a molecular entity that is not a part of the gene or protein of interest. As will be appreciated by those skilled in the art, conjugates may have the useful property of combining, in a single molecular entity, (a) one or more utilities, biochemical or biological functions of the gene or protein of interest with (b) the chemical, physical or biological properties of the chemical moieties structurally linked thereto.

For example, nucleic acid probes can be combined with a detectable label in order to produce a probe that can be used to directly detect nucleic acids capable of hybridizing to the gene of interest or homologs thereof. One type of functional derivative of a mitofusin-encoding nucleic acid is an oligonucleotide having at least 18 nucleotides, and comprising a nucleotide sequence contained within a nucleotide sequence selected from the group consisting of SEQ ID NO:1; 3; 5; 7; 9; 11; 12; 13; 15; and 17 or the reverse complement of such a nucleotide sequence. Such oligonucleotides have the ability to specifically hybridize to nucleic acids encoding a Fzo homolog or a mitofusin.

As another example, one type of functional derivative of a Fzo homolog protein or a mitofusin is a polypeptide having at least 12 amino acids, and comprising an amino acid sequence contained within an amino acid sequence selected from the group consisting of SEQ ID NO:2; 4; 6; 8; 10; 14; 16; 18; 19; or 20. Such polypeptides can be used to immunize animals in order to produce antibodies specific for particular epitopes with a Fzo homolog or mitofusin.

As another example, a fusion protein may combine a binding site for a factor, wherein the binding site corresponds to an amino acid sequence derived from a protein of interest, with an amino acid sequence that fluoresces, in order to produce a fluorescent conjugate that can be used to measure such binding and to identify molecules that enhance, modulate or inhibit such binding.

The mitofusin and Fzo homolog genes, the proteins encoded thereby, and functional derivatives of such genes and proteins may be used to enhance, mediate, modulate or inhibit mitochondrial fusion, for the purposes of introducing intact or partial mitochondrial genomes (DNA molecules) or other molecules (such as mitochondrial proteins and lipids) into mitochondria in diseased host cells or tissues, either in culture or in an intact animal or individual. The use of mitofusin proteins to drive fusion of membrane-bound entities, e.g. mitochondria, in vitro enables investigation of the mechanism of mitochondrial fusion, recombination or complementation between mitochondrial DNA molecules, maintenance of mitochondrial genomes, and complementation between mitochondria. The term "complementation" refers to a situation in which, for example, two mitochondrial genomes are present in a single mitochondrion, wherein the first of such genomes is incapable of providing a mitochondrial function of interest, but the second genome nevertheless provides an amount of such function sufficient to compensate for the deficiency of the first genome.

Mitofusins are herein identified in insects (*Drosophila melanogaster*), yeast (*Saccharomyces cerevisiae*), worms (*Caenorhabditis elegans*), mice (*Mus musculus*), rats (*Rattus norvegica*) and humans (*Homo sapiens*). Representative examples of mitofusin genetic sequences are provided in SEQ ID NO:1 and 3 (*Drosophila*) and SEQ ID NO:5 and 9 (human). The respective encoded proteins are provided as SEQ ID NO:2 and 4 and SEQ ID NO:6 and 10, respectively. At least two distinct forms of mitofusins have been identified in mice and humans, herein termed Mfn1 and Mfn2.

The yeast, worm, mouse and human homologs share signature conserved features with *Drosophila* Fzo protein. All are large GTPases with a predicted trans-membrane domain, and a predicted coiled-coil region (in that order, moving from amino to carboxy termini), near their C-termini. The region of the protein C-terminal to the predicted trans-membrane domain has a high pI, characteristic of proteins found in the mitochondrial matrix, while the region of the protein N-terminal to the predicted trans-membrane domain has a lower pI, characteristic of cytoplasmic proteins. These observations, coupled with the association of mitofusin protein with mitochondria at the time of fusion, with the GTPase domain exposed on the cytoplasmic face of mitochondria. The predicted GTPase activity is required for mitochondrial fusion in vivo, but not for import of the protein into or association with mitochondria.

Nucleic Acids Encoding Mitofusins

The nucleic acid sequence encoding a mitofusin may be cDNA or genomic DNA or a fragment thereof. The term "mitofusin gene" shall be intended to mean the open reading frame encoding specific mitofusin polypeptides, introns, as well as adjacent 5' and 3' non-coding nucleotide sequences involved in the regulation of expression, up to about 1 kb beyond the coding region, but possibly further in either direction. A mitofusin gene, or its corresponding cDNA, may be introduced into an appropriate vector for extrachromosomal maintenance or for integration into the genome of the host cell or organism.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, removed by nuclear RNA splicing, to create a continuous open reading frame encoding a mitofusin protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

Genomic regions of interest include the non-transcribed sequences 5' or 3' to a mitofusin gene. This region of DNA contains the native promoter elements that direct expression of the linked mitofusin gene. A promoter region will usually have at least about 100 nt of sequence located 5' to a mitofusin gene and will often extend 5' to include other regulatory elements.

The sequence of this 5' region may be utilized for promoter elements, including enhancer binding sites, that provide for developmental regulation in tissues where mitofusins are expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Human Mfn1 and Mfn2 mRNAs were expressed at low levels in all tissues tested. However, the levels of Mfn1 and Mfn2 mRNA expression varied in different tissues, with Mfn1 mRNA levels being elevated in more different tissue and cell types than Mfn2 mRNA. An Mfn1-cDNA probe detected two transcripts of 6.4 kb and 3.6 kb in a variety of adult human tissues, including heart, pancreas, skeletal muscle, brain, liver, placenta, lung, and kidney. An Mfn2-specific probe detected a single 5.5 kb mRNA in the same range of tissues. Both Mfn1 and Mfn2 mRNA-levels were elevated in heart compared to other tissues. In addition, Mfn2 mRNA was also elevated in skeletal muscle. In contrast, Mfn1 mRNA-levels appeared slightly elevated in pancreas and liver, but not in skeletal muscle. Expression of both Mfn1 and Mfn2 was detected in fetal tissues, with Mfn1 mRNA more abundant than Mfn2. The levels of Mfn1-mRNA expression were elevated in certain carcinoma and lymphoma derived cancer cell lines, whereas Mfn2 expression was not elevated in the cancer cells lines tested.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. (see, for example, see Blackwell et al. (1995) *Mol Med* 1:194–205; Mortlock et al. (1996) *Genome Res.* 6:327–33; and Joulin and Richard-Foy (1995) *Eur. J. Biochem* 232:620–626.

The regulatory sequences may be used to identify cis acting sequences required for transcriptional or translational regulation of mitofusin expression, especially in different tissues or stages of development, and to identify cis-acting sequences and trans acting factors that regulate or mediate mitofusin expression. Such transcription or translational control regions may be operably linked to a mitofusin gene in order to promote expression of wild type or altered human or *Drosophila* mitofusins or other proteins of interest in cultured cells, or in embryonic, fetal or adult tissues, and for gene therapy.

In addition coding sequences may be used to identify cis acting sequences and possible trans-acting factors that regulate or mediate import of mitofusins into or on to mitochondria. Such mitochondrial import signals may be operably linked to a mitofusin or other gene to promote import of wild-type or altered mitofusins or other proteins of interest into or onto mitochondria in vivo or in vitro.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The mitofusin genes are isolated and obtained in substantial purity, generally as other than an intact chromosome. Usually, the DNA will be obtained substantially free of other nucleic acid sequences that do not include a mitofusin sequence or fragment thereof, generally being at least about 50%, usually at least about 90% pure and are typically "recombinant," i.e. flanked by one or more nucleotides with which it is not normally associated on a naturally occurring chromosome.

The DNA sequences are used in a variety of ways. They may be used as probes for identifying mitofusin related genes. Between mammalian species, e.g. human and mouse, homologs have substantial sequence similarity, i.e. at least 75% sequence identity between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J. Mol. Biol.* 215:403–10.

The amino acid sequence similarity between invertebrates and vertebrates is sufficient to identify homologous genes. Regions of more highly conserved sequence are identified through a comparison of the provided sequences. Such conserved regions are used to design degenerate oligonucleotide primers, as known in the art. Conveniently, the primers are used in an polymerase chain reaction amplification with cDNA or genomic DNA from the target organism as a substrate. The resulting amplified nucleic acid product comprises a fragment of the mitofusin from the target organism, and can be used to isolate the complete gene by various methods known in the art, including rapid amplification of cloned ends (RACE), hybridization to cDNA libraries, etc.

Nucleic acids encoding all or a portion of a mitofusin homolog can also be identified by means of Southern analysis of DNA isolated from different biological sources.

Total DNA can be isolated from any organism (see Ausubel, F. et al Current Protocols in Molecular Biology, 1988). The source of nucleic acids encoding mitofusins and other Fzo homologs may be any species, e.g. primate species, particularly human; rodents, such as rats and mice, canines, felines, bovines, ovines, equines, yeast, Drosophila, Caenorhabditis, etc. The isolated DNA is restriction digested, run in agarose gels and blotted onto either nitrocellulose or nylon filters. These filters are then probed with full or partial-length coding sequences of the Fzo gene or of any of the Fzo homologs or mitofusins described herein.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. At low stringency hybridization and washing conditions, nucleic acids with a degree of similarity to a nucleic acid encoding a Fzo homolog as low as 30% can be identified. Sequence identity may be determined by hybridization under stringent conditions, for example, at 50° C. or higher and 0.1×SSC (9 mM saline/0.9 mM sodium citrate). By using probes, particularly labeled probes of DNA sequences, one can isolate homologous or related genes. At high stringent hybridization and washing conditions, only the genes with a similarity to the probe DNA higher than 80% will be identified. These high stringent conditions consist of an overnight hybridization at 68° C. in a variety of buffers (Ausubel et al., eds., *Current Protocols in Molecular Biology*, 1988), followed by 2 washes of 10 min each at 68° C. in 2× standard saline citrate, SSC,/0.1% SDS, one wash of 10 min at 68° C. in 1×SSC/0.1% SDS, and one wash of 5 min at 68° C. in 0.1×SSC/0.1% SDS).

The DNA may also be used to identify expression of the gene in a biological specimen. The manner in which one probes cells for the presence of particular nucleotide sequences, as genomic DNA or RNA, is well established in the literature and does not require elaboration here. Conveniently, a biological specimen is used as a source of mRNA. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of mitofusin gene expression in the sample.

The sequence of a mitofusin gene, including flanking promoter regions and coding regions, may be mutated in various ways known in the art to generate targeted changes in promoter strength, sequence of the encoded protein, etc. The DNA sequence or product of such a mutation will be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAg system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199:537–9 (1985); and Prentki et al, *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:120–4 (1989).

Such mutated genes may be used to study structure-function relationships of mitofusins, or to alter properties of the protein that affect its function or regulation. For example, constitutively active fusogens, or a dominant negatively active protein to block fusion, may be created in this manner.

Mitofusin Polypeptides

The subject gene may be employed for producing all or portions of the mitofusin protein, or functional derivatives (such as fusion proteins) of mitofusin proteins. For expression, an expression cassette may be employed. The expression cassette will provide a transcriptional and translational initiation region, which may be inducible or constitutive, where the coding region is operably linked under the transcriptional control of the transcriptional initiation region, and a transcriptional and translational termination region wherein these regions are functional in the host cell of choice. These control regions may be native to a mitofusin gene, or may be derived from exogenous sources.

The expression cassette may be integrated into the genome of a host cell, or may be part of an autogenously replicating expression construct that also comprises an origin of replication and a selectable marker such as, for example, a gene that encodes a function that confers resistance to an agent that would otherwise kill or prevent the growth of the host cell (e.g., for bacterial hosts, antibacterial agents such as ampicillin, tetracycline, kanamycin, streptomycin, chloramphenicol and neomycin; for eukaryotic hosts, cytotoxic agents such as G418, blasticidin, hygromycin and Zeocin™).

The peptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In many situations, it may be desirable to express the mitofusin gene in eukaryotic cells, where the mitofusin gene will benefit from native folding and post-translational modifications. Small peptides can also be synthesized in the laboratory. Peptides that are subsets of a complete mitofusin sequence, usually at least about 12 amino acids in length, more usually at least about 20 amino may be used to identify and investigate parts of the protein important for function, such as the GTPase domain, mitochondrial import signals, or the coiled-coil regions, or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The use of the expressed protein for in vitro models of mitochondrial fusion is of particular interest. The protein may be used to explore conditions and sequences that are required for association of the protein with mitochondria in cell extracts, and for setting up in vitro systems to assay mitochondrial fusion.

The expressed mitofusin polypeptides are used for the production of antibodies, where short fragments provide for antibodies specific for the particular polypeptide, and larger fragments or the entire protein allow for the production of antibodies over the surface of the polypeptide. Antibodies may be raised to the wild-type or variant forms of mitofusin. Antibodies may be raised to isolated peptides corresponding to these domains, or to the native protein, e.g. by immunization with cells expressing mitofusin, immunization with liposomes having mitofusin inserted in the membrane, etc.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual,* Harlow and Lane eds., Cold Spring Harbor Laboratories, Cold Spring Harbor, N.Y., 1988. If desired, the mRNA encoding the heavy and light chains may be isolated and mutagenized by cloning in *E. coli,* and the heavy and light chains mixed to further enhance the affinity of the antibody. Alternatives to in vivo immunization as a method of raising antibodies include binding to phage "display" libraries, usually in conjunction with in vitro affinity maturation. Antibodies may be "humanized" to produce therapeutic agents that may be introduced into humans without triggering an undesired immune response (Gussow et al. (1991), *Methods Enz.* 203:99–121).

Antisera were raised against the C-terminal 77 amino acids of Mfn1. The affinity-purified antibodies recognized an endogenous single protein. The affinity purified anti-Mfn1 antiserum also recognized recombinant GFP-tagged Mfn1 fusion protein expressed in mammalian tissue culture cells by transient transfection, but did not crossreact with Mfn2 protein similarly expressed. In addition, the anti-Mfn1 antibody recognized overexpressed Mfn1 but not Mfn2 in immunofluorescence analysis of cells transiently transfected with various Mfn1 and Mfn2 expression constructs. Immunoblotting experiments with the anti-Mfn1 antibodies revealed expression of endogenous Mfn1 protein in HeLa cells, human kidney and heart, as well as in mouse heart, liver, kidney, NIH3T3 fibroblasts, mouse C2C12 myoblasts and differentiated myotubes, and rat clone9 cells. An Mfn2-specific antibody was raised against a peptide from an internal region of Mfn2 with relatively low homology to Mfn1. The affinity-purified antibody detected recombinant and native Mfn2 protein. Mfn2 protein appeared to be present in significantly higher levels in human heart than human kidney.

Diagnostic Uses

Biochemical studies may be performed to determine whether a sequence polymorphism in a mitofusin coding region or control regions is associated with disease, particularly degenerative diseases associated with mitochondrial defects, e.g. amyotrophic lateral sclerosis, Huntington's disease, Parkinson's disease, and Alzheimer's disease. Disease associated polymorphisms may include mutations that alter expression level, that affect the fusogenic activity of the protein, that alter the subcellular localization of the mitofusin, etc.

Changes in the promoter or enhancer sequence that may affect expression levels of mitofusin can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence. Where large amounts of DNA are available, genomic DNA is used directly. Alternatively, the region of interest is cloned into a suitable vector and grown in sufficient quantity for analysis. Cells that express a mitofusin may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of current techniques may be found in Sambrook, et al. *Molecular Cloning: A Laboratory Manual,* CSH Press 1989, pp. 14.2 to 14.33. Amplification may also be used to determine whether a polymorphism is present, by using a primer that is specific for the polymorphism. Alternatively, various methods are known in the art that utilize oligonucleotide ligation as a means of detecting polymorphisms, for examples see Riley et al. (1990) *Nucl. Acids Res.* 18:2887–2890; and Delahunty et al. (1996) *Am. J. Hum. Genet.* 58:1239–1246.

A detectable label may be attached to a nucleic acid probe for hybridization analyses ("Southern" and "Northern"), or linked to one or more PCR primers in an amplification reaction or otherwise included in such reactions. A "detectable label" is a substance which can be covalently attached to or firmly associated with a nucleic acid probe which confers the ability to detect the probe by a given means. A suitable detectable label will not lose the quality responsible for detectability during manipulations thereof. Suitable detectable labels include radio opaque substances (including colloidal metals); chemiluminescent molecules such as digoxigenin; fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); enzymes for which colorometric substrates are available, such as alkaline phosphatase; radioactive labels, e.g. $^{32}P$, $^{33}P$, $^{35}S$, $^{3}H$, $^{14}C$, $^{125}I$; etc. The label may be a two stage system, where the amplified DNA is conjugated to biotin, haptens, etc. having a high affinity binding partner, e.g. streptavidin or avidin in the case of biotin, specific antibodies in the case of haptens, etc., where the binding partner is conjugated to a detectable label. The label may be conjugated to one or both of the primers. Alternatively, the pool of nucleotides used in the amplification is labeled, so as to incorporate the label into the amplification product.

The amplified or cloned fragment may be sequenced by dideoxy or other methods, and the sequence of bases compared to a wild-type mitofusin sequence. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. The hybridization pattern of a control and variant sequence to an array of oligonucleotide probes immobilized on a solid support, as described in PCT application WO 95/11995, may also be used as a means of detecting the presence of variant sequences. Alternatively, where a polymorphism creates or destroys a recognition site for a restriction endonuclease, the fragment is digested with that endonuclease, and the products size fractionated to determine whether the fragment was digested. Fractionation is performed by gel or capillary electrophoresis, particularly acrylamide or agarose gels.

Hybridization with a polymorphism specific probe may also be used to determine its presence, by Southern blots, dot blots, etc. The hybridization pattern of a control and variant sequence to an array of oligonucleotide probes immobilized on a solid support, as described in U.S. Pat. No. 5,445,934, or in PCT application WO 95/35505, may also be used as a means of detecting the presence of variant sequences.

Screening for mutations in mitofusin may be based on the functional or antigenic characteristics of the protein. Various immunoassays designed to detect polymorphisms in mitofusin proteins may be used in screening. Where many diverse genetic mutations lead to a particular disease phenotype, functional protein assays have proven to be effective screening tools. The activity of the encoded mitofusin protein may be determined by comparison with the wild-type protein.

Antibodies specific for a mitofusin may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal mitofusin in patient cells. For example, detection may utilize staining of cells or histological sections, performed in accordance with conventional methods. Cells are permeabilized to stain intra-mitochondrial and/or cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase Alternatively, the secondary antibody conjugated to a fluorescent compound, e.g. fluorescein, rhodamine, Texas red, etc. The absence or presence of antibody binding may be determined by various methods, including flow cytometry of dissociated cells, microscopy, radiography, scintillation counting, etc.

Determination of the subcellular localization of mitofusin through antibody binding may be used in mutation analysis to detect mutations that cause failure to express or properly localize mitofusin proteins. The assay can be performed by immunohistochemistry or immunofluorescence, where the cell sample is stained with a mitofusin specific antibody followed by labeled secondary antibodies as described above to determine whether mitofusin is properly localized in the mitochondria. Alternatively, cell lysates may be fractionated and the level of mitofusin in the mitochondrial fraction quantitated.

Other diagnostic assays of interest are based on the functional properties of mitofusin proteins. For example, a functional assay may be based on the membrane changes mediated by mitofusin gene products. Other assays may, for example, detect conformational changes, or changes in the subcellular localization of mitofusin proteins.

Mitofusin protein co-fractionates with mitochondrial markers during differential centrifugation, and migrates in an apparent high molecular mass complex through a size exclusion gel filtration column. Mfn1 localizes to mitochondria when expressed in tissue culture cells by transient transfection. In contrast, a C-terminal truncated mitofusin protein lacking the conserved transmembrane domain and predicted coiled-coil tail does not localize to mitochondria.

Modulation of Gene Expression

The mitofusin genes, gene fragments, or the encoded protein or protein fragments are useful in gene therapy to treat degenerative and other disorders involving mitochondria, including myopathies and Alzheimer's disease. Expression vectors may be used to introduce the mitofusin gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or mitofusin protein may be introduced into tissues or host cells by any number of routes, including viral infection, microinjection, or fusion of vesicles or mitochondria. Jet injection may also be used for intramuscular administration, as described by Furth et al. (1992) *Anal. Biochem.* 205:365–368. The DNA may be coated onto gold microparticles, and delivered intradermally by a particle bombardment device, or "gene gun" as described in the literature (see, for example, Tang et al. (1992) *Nature* 356:152–154), where gold microprojectiles are coated with the mitofusin or DNA, then bombarded into skin cells.

Antisense molecules can be used to down-regulate expression of mitofusin in cells. The antisense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha-anomer of deoxyribose may be used, where the base is inverted with respect to the natural beta-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to antisense inhibitors, catalytic nucleic acid compounds, e.g. ribozymes, antisense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–4442). Examples of oligonucleotides with catalytic activity are described in WO 9506764. Conjugates of antisense ODN with a metal complex, e.g. terpyridylCu(II), capable of mediating mRNA hydrolysis are described in Bashkin et al. (1995) *Appl. Biochem. Biotechnol.* 54:43–56.

Cell and Animal Models

The subject nucleic acids can be used to generate genetically modified non-human animals or site specific gene modifications in cell lines, for the study of mitofusin function or regulation, or to create animal models of diseases, including mitochondrial diseases, muscle myopathies, neurodegenerative disorders, and aging. The term ☐transgenic☐ is intended to encompass genetically modified animals having a deletion or other knock-out of mitofusin gene activity, having an exogenous mitofusin gene that is stably transmitted in the host cells where the gene may be altered in sequence to produce a modified protein, or having an exogenous mitofusin promoter operably linked to a reporter gene. Transgenic animals may be made through homologous recombination, where the mitofusin locus is altered. Alternatively, a nucleic acid construct is randomly integrated into the genome. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

Investigation of genetic function may also utilize non-mammalian models, particularly using those organisms that are biologically and genetically well-characterized, such as *C. elegans, D. melanogaster* and *S. cerevisiae.* The subject gene sequences may be used to knock-out corresponding gene function or to complement defined genetic lesions in order to determine the physiological and biochemical pathways involved in mitofusin function. Drug screening may be performed in combination with complementation or knock-out studies, e.g. to study progression of degenerative disease, to test therapies, or for drug discovery.

The modified cells or animals are useful in the study of mitofusin function and regulation. For example, a series of small deletions and/or substitutions may be made in the mitofusin gene to determine the role of different domains in GTPase activity, membrane fusion, etc. Specific constructs of interest include, but are not limited to, antisense mitofusin constructs to block mitofusin expression, expression of dominant negative mitofusin mutations, and over-expression of a mitofusin gene. One may also provide for expression of the mitofusin gene or variants thereof in cells or tissues where it is not normally expressed or at abnormal times of development. In addition, by providing expression of mitofusin protein in cells in which it is otherwise not normally produced, one can induce changes in mitochondrial behavior.

DNA constructs for homologous recombination will comprise at least a portion of the mitofusin gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting chimeric animals screened for cells bearing the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on mitochondrial fusion, to test potential therapeutics or treatment regimens, etc.

Screening Assays

By providing for the production of large amounts of mitofusin protein, one can identify ligands or substrates that bind to, modulate or mimic the action of mitofusin. Drug screening identifies agents that provide a replacement or enhancement for mitofusin function in affected cells. A wide variety of assays may be used for this purpose, including labeled in vitro protein-protein binding assays, protein-DNA binding assays, protein-mitochondria or protein mitochondria fraction, electrophoretic mobility shift assays, immunoassays for protein binding, and the like. All or a fragment of the purified protein may also be used for determination of three-dimensional crystal structure, which can be used for modeling intermolecular interactions, membrane fusion, etc. Altered mitofusin molecules, either as an isolated recombinant protein, or as a genetically modified cell or animal model may be assayed to investigate structure function parameters, including but not limited to potential mitochondrial import sequences, protein interaction domains, GTPase motifs, and dominant negative acting forms of the protein.

The term "agent" as used herein describes any molecule, e.g. protein or pharmaceutical, with the capability of altering, mimicking or interfering with the physiological function of a subject mitofusin or Fzo homolog. Generally, a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

It may be preferable in some instances to use a functional derivative of a Fzo homolog or mitofusin in screening assays. For example, a fusion protein in which mitofusin amino acid sequences are linked to a detectable polypeptide, for example green fluorescent protein (GFP), can be directly detected without the need to add additional reagents for detection such as, e.g., antibodies. As another example, specific binding sites (such as the 6×His tag, which binds Nickel; streptavidin or avidin polypeptides, which bind biotin; or glutathione S transferase, GST, which binds glutathione) can be connected to mitofusin polypeptides in fusion proteins.

Naturally occurring mitofusins are typically membrane-bound, at least partially hydrophobic proteins. Because hydrophilic and water-soluble proteins are easier to incorporate into screening assays, including high throughput screening assays, in which reactions and binding events necessary for such assays take place in the aqueous phase, water-soluble functional derivatives of mitofusins have distinct advantages over hydrophobic, membrane-bound forms of mitofusins. As described in more detail in the Examples, functional derivatives of mitofusins that lack amino acid sequences required for membrane insertion are water-soluble, or at least more hydrophilic than the wild type proteins from which they are derived. Such hydrophilic/water-soluble can nonetheless retain one or more biochemical or biological activity or function of interest, and can be used in assays designed to identify agents that interfere with such activities or functions.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening.

Arthropod Fzo proteins, Fzo homologs, mitofusins, nucleic acids encoding such proteins, and functional derivatives thereof, are used in screening assays to identify anti-arthropod agents that act by, for example, inducing sterility in and/or causing the death of undesirable arthropods, preferably in a species-specific manner, by modulating or inhibiting a mitofusin function or activity. By "species-specific," it is meant that such anti-insect agents have a deleterious effect on one or more species of arthropod pests but have little or no deleterious effects, or effects that are acceptable to appropriate regulatory agencies, on desirable insect species, plants and animals. For purposes of the present invention, arthropod pests include insects and arachnids selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, and Acari, particularly Coleoptera and Lepidoptera. A list of arthropod pests associated with major crop plants are described below. Fzo homologs and mitofusins obtained from such pests, functional derivatives thereof, and screening assays incorporating such materials, are included within the scope of the present invention.

Diptera (flies and mosquitoes) and crops affected thereby include *Hylemya platura*, seedcorn maggot and *Mayetiola destructor*, Hessian fly for barley; *Psilia rosae*, carrot rust fly. for carrot; *Delia brassicae*, cabbage maggot; *Delia radicum*, cabbage root fly for crucifers (broccoli, cabbage, cauliflower, collards); *Agromyza parvicornis*, corn blotch leafminer, *Hylemya platura*, seedcorn maggot for maize; *Contarinia sorghicola*, sorghum midge, for sorghum; *Hylemya platura*, seedcorn maggot for soybean; *Tetanops myopaeformis*, sugarbeet root maggot; *Neolasioptera murtfeldtiana*, sunflower seed midge; *Scrobipalpula absoluta*, tomato leafminer; *Liriomyza sativae*, vegetable leafminer; *Liriomyza trifolli*, tomato leafminer; *Liviomyza sativae*, vegetable leaf miner; *Sitodiplosis mosellana*, wheat midge; *Meomyza americana*, wheat stem maggot; *Hylemya coarctata*, wheat bulb fly; *Mayetiola destructor*, Hessian fly (wheat).

Lepidoptera (butterflies and moths) and crops affected thereby include: *Ostrinia nubilalis*, European corn borer (barley); *Plutella xylostella*, diamondback moth (canola); *Heliothis virescens*, cotton boll worm; *Helicoverpa zea*, cotton bollworm; *Helicoverpa armigera*, cotton bollworm; *Spodoptera exigua*, beet armyworm; *Pectinophora gossypiella*, pink bollworm; *Artogeia rapae*, imported cabbageworm (crucifers); *Pieris brassicae*, cabbage butterfly; *Trichoplusia ni*, cabbage looper; *Mamestra configura*, bertha army worm (crucifers); *Spodoptera exigua*, beet armyworm; *Agrotis ipsilon*, black cutworm; *Plutella xylostella*, diamondback moth; *Agrotis segetum*, common cutworm; *Cydia pomonella*, codling moth; *Platynota idaeusalis*, tufted apple bud moth; *Endopiza viteana*, grape berry moth; *Diatraea grandiosella*, southwestern corn borer; *Elasmopalpus lignosellus*, lesser cornstalk borer; *Ostrinia nubilalis*, European corn borer; *Ostrinia furnacali's*, Asian corn borer; *Sesamia nonagroides*, Mediterranean corn borer; *Agrotis ipsilon*, black cutworm; *Spodoptera frugiperda*, fall armyworm; *Helicoverpa zea*, corn earworm; *Diatraea saccharalis*, sugarcane borer; *Spodoptera exigua*, beet armyworm; *Ostrinia nubilalis*, European corn borer; *Spodoptera eridania*, southern armyworm; *Ostrinia nubilalis*, European corn borer; *Phthorimaea operculella*, potato tuberworm; *Spodoptera frugiperda*, fall armyworm; *Diatraea saccharalis*, sugarcane borer; *Chilo suppressalis*, asiatic rice borer; *Helicoverpa zea*, corn earworm; *Scirpophaga* sp.; *Chilo partellus*, sorghum borer; *Elasmopalpus lignosellus*, lesser cornstalk borer; *Feltia subterranea*, granulate cutworm; *Spodoptera frugiperda*, fall armyworm; *Helicoverpa zea*, corn earworm; *Pseudoplusia includens*, soybean looper; *Agrotis ipsilon*, black cutworm; *Anticarsia gemmatalis*, velvetbean caterpillar; *Plathypena scabra*, green cloverworm; *Spodoptera exigua*, beet armyworm; *Ostrinia nubilalis*, European corn borer; *Heliothis virescens*, cotton boll worm; *Helicoverpa zea*, cotton bollworm; *Diatraea saccharalis*, sugarcane borer; *Agrotis ipsilon*, black cutworm; *Suleima helianthana*, sunflower bud moth; *Homoeosoma electellum*, sunflower moth; *Keiferia lycopersicella*, tomato pinworm; *Helicoverpa zea*, tomato fruitworm; *Manduca quinquemaculata*, tomato hornworm; *Spodoptera exigua*, beet armyworm; *Spodoptera praefica*, western yellowstriped armyworm; *Spodoptera ornithogalli*, yellowstriped armyworm; *Spodoptera eridania*, southern armyworm; *Spodoptera frugiperda*, fall armyworm; *Agrotis ipsilon*, black cutworm; *Peridroma saucia*, variegated cutworm; *Papaipema nebris*, stalk borer; *Trichoplusia ni*, cabbage looper; *Manduca sexta*, tobacco hornworm; *Agrotis orthogonia*, pale western cutworm; *Pseudaletia unipunctata*, army worm; *Spodoptera frugiperda*, fall armyworm; *Elasmopalpus lignosellus*, lesser cornstalk borer;

Hemiptera (Bugs) and crops affected thereby include *Blissus leucopterus leucopterus*, chinch bug; *Acrosternum hilare*, green stink bug; *Euschistus servus*, brown stink bug; *Lygus lineolaris*, tarnished plant bug; *Blissus leucopterus leucopterus*, chinch bug; *Blissus leucopterus leucopterus*, chinch bug; *Acrosternum hilare*, green stink bug; *Blissus leucopterus leucopterus*, chinch bug; *Acrosternum hilare*, green stink bug; lygus bug; *Acrosternum hilare*, green stink bug; *Euschistus servus*, brown stick bug; etc.

Beetles of interest include *Ceutorhychus assimils*, cabbage seedpod weevil; *Phyllotreta cruciferae*, crucifer flea beetle; *Anthonomus grandis*, boll weevil; *Phyllotreta cruciferae*, crucifer flea beetle; *Phyllotreta pusilla*, western black flea beetle; *Diabrotica virgifera. virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Anthonomus eugenii*, pepper weevil; *Leptinotarsa decemlineata*, Colorado potato beetle; *Epitrix cucumeris*, potato flea beetle; *Hemicrepidus memnonius*, wireworms; *Colaspis brunnea*, grape colaspis; *Lissorhoptrus oryzophilus*, rice water weevil; *Sitophilus oryzae*, rice weevil; *Oulema oryzae*, rice beetle; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Epilachna varivestis*, Mexican bean beetle; *Zygogramma exclamationis*, sunflower beetle; *Bothyrus gibbosus*, carrot beetle; *Melanotus* spp., wireworms; *Leptinotarsa decemlineata*, Colorado potato beetle; *Epitrix hirtipennis*, tobacco flea beetle; *Oulema melanopus*, cereal leaf beetle; *Hypera punctata,* clover leaf weevil; *Diabrotica undecimpunctata howardi,* southern corn rootworm Hymenoptera (sawflies, ants, wasps etc) and crops affected thereby include *Solenopsis milesta,* thief ant; and *Cephus cinctus,* wheat stem sawfly.

Homoptera (whiteflies, aphids etc.) include *Schizaphis graminum,* greenbug; *Brevicoryne brassicae,* cabbage aphid; *Cavariella aegopodii,* carrot aphid; *Aphis gossypii,* cotton aphid; *Pseudatomoscelis seriatus,* cotton fleahopper; *Trialeurodes abutilonea,* bandedwinged whitefly; *Brevicoryne brassicae,* cabbage aphid; *Myzus persicae,* green peach aphid; *Dysaphis plantaginea,* rosy apple aphid; *Rhopalosiphum maidis,* corn leaf aphid; *Anuraphis maidiradicis,* corn root aphid; *Bemisia argentifolii,* silverleaf whitefly; *Bemisia tabaci,* sweetpotato whitefly; *Brevicoryne brassicae,* cabbage aphid; *Myzus persicae,* green peach aphid; *Enipoasca fabae,* potato leafhopper; *Myzus persicae,* green peach aphid; *Macrosiphum euphorbiae,* potato aphid; *Paratrioza cockerelli,* potato psyllid; *Nephotettix nigropictus,* rice leafhopper; *Nilaparvata lugens; Sogatella furcifera; Laodelphaax striatellus; Rhopalosiphum maidis,* corn leaf aphid; *Sipha flava,* yellow sugarcane aphid; *Myzus persicae,* green peach aphid; *Empoasca fabae,* potato leafhopper; *Pemphigus popullivenae,* sugar beet root aphid; *Saccharosydne saccharivora,* West Indian canefly; *Sipha flava,* yellow sugarcane aphid; *Myzus persicae,* green peach aphid; *Macrosiphum euphorbiae,* potato aphid; *Trileurodes vaporariorum,* greenhouse whitefly; *Bemisia tabaci,* sweetpotato whitefly; *Bemisia argentifolii,* silverleaf whitefly; Russian wheat aphid; *Schizaphis graminum,* greenbug; *Macrosiphum avenae,* English grain aphid; *Aphis fabae,* bean aphid.

Orthoptera (grasshoppers crickets, and cockroaches) include *Melanoplus femurrubrum,* redlegged grasshopper; *Melanoplus differentialis,* differential grasshopper; *Melanoplus femurrubrum,* redlegged grasshopper; *Melanoplus sanguinipes,* migratory grasshopper; *Melanoplus femurrubrum,* redlegged grasshopper; *Melanoplus differentiahs,* differential grasshopper; *Melanoplus femurrubrum,* redlegged grasshopper; *Melanoplus differenualis,* differential grasshopper; *Melanoplus sanguinipes,* migratory grasshopper.

Thysanontera (thrips) and crops affected thereby include *Thrips tabaci,* onion thrips; *Frankliniella fusca,* tobacco thrips; *Thrips tabaci,* onion thrips; *Anaphothrips obscurus,* grass thrips; *Thrips palmi,* melon thrips; *Thrips palmi,* melon thrips; *Sericothrips vanabilis,* soybean thrips; *Thrips tabaci,* onion thrips; *Frankliniella occidentakis,* western flower thrips; *Frankliniella fusca,* tobacco thrips; *Thrips tabaci,* onion thrips; *Frankliniella fusca,* tobacco thrips.

Acari (mites and ticks) and crops affected thereby include *Petrobia latens,* brown wheat mite; *Panonychus citri,* citrus red mite; *Brevipalpus lewisi,* citrus flat mite; *Phyllocoptrutra oleivora,* citrus rust mite; *Tetranychus cinnabarinus,* carmine spider mite; *Tetranychus urticae,* twospotted spider mite; *Panonychus ulmi,* European red mite; *Tetranchus* sp, spider mite; *Tetranychus urticae,* twospotted spider mite; *Tetranychus cinnabarinus,* carmine spider mite; *Tetranychus turkestani,* strawberry spider mite; *Tetranychus urticae,* two spotted spider mite; *Tetranychus urticae,* two spotted spider mite; *Tetranychus urticae,* two spotted spider mite; *Aculops iycopersici,* tomato russet mite; *Steneotarsonemus pallidus,* cyclamen mite; *Aceria tulipae,* wheat curl mite.

Anti-arthropod agents identified according to the methods of the invention are used to management and control such undesirable insects for the purposes of crop protection and improved health and hygiene for animals including mammals such as dogs, cats, minks, horses, cows, oxen, pigs and humans. Adult insects, pupae, larvae, or cultured insect cells (including for example, the Sf9 and Sf21 cell lines derived from *Spodoptera frugiperda,* and the HIGH FIVE™ cell line from *Trichopolusia ni;* these three cell lines are available from InVitrogen, Carlsbad, Calif.) are used to confirm the biological activity of agents that are initially screened in vitro for their ability to enhance, modulate or inhibit one or more functions or activities of Fzo proteins and/or functional derivatives thereof. Other functional derivatives are used for target validation; for example, antisense nucleic acids are used to inhibit expression of a Fzo protein or Fzo homolog, and the effects of such down-regulation are measured in order to confirm that reduced activity of the Fzo protein or homolog will result in the predicted desired result, e.g., sterility, death, etc.

Fungal Fzo proteins, Fzo homologs, mitofusins, nucleic acids encoding such proteins, and functional derivatives thereof, are further used in screening assays to identify antifungal agents that act by, for example, blocking a step in the cell cycle of, promoting the loss of mitochondria from cells, and/or causing the death of undesirable fungi, preferably in a species-specific manner, by modulating or inhibiting a mitofusin function or activity. Functional derivatives of Fzo homologs and mitofusins are used for target validation; for example, antisense nucleic acids are used to inhibit expression of a Fzo homolog or mitofusin, and the effects of such down-regulation are measured in order to confirm that reduced activity of the Fzo homolog or mitofusin will result in the predicted desired result, e.g., cell cycle arrest, cytotoxicity, etc.

One group of undesirable fungi, for which there is a need for antifungal agents for the management thereof, include fungal phytopathogens of plants. A list of fungal pests associated with major crop plants is provided below. Fzo homologs, mitofusins, and functional derivatives thereof, and screening assays incorporating such materials from such fungi are included within the scope of the present invention.

Fungal diseases of plants include Brown stripe downy mildew; *Sclerophthora rayssiae;* Graminicola downy mildew, *Sclerospora graminicola;* Java downy mildew, *Peronosclerospora maydis;* Phillipine downy mildew, Peronoscler. Philippinensis; Rajasthan downy mildew, *Peronosclerospora heteropogoni*; Sorghum downy mildew, *Peronosclerospora sorghi;* Spontaneum downy mildew, *Peronosclerospora spontanea;* Sugarcane downy mildew, *Peronosclerospora sacchari;* Rusts, *Puccinia graminis* f.sp. *tritici; Puccinia recondita* f.sp. *tritici; Puccinia striiformis;* Smuts, *Tilletia tritici; Tilletia controversa; Tilletia indica; Ustilago tritici; Urocystis tritici;* Root rots, Foot rots and Blights, *Gaeumannomyces graminis; Pythium* spp.; *Fusarium culmorum; Fusarium graminaerum; Fusarium avenaceum; Drechslere tritici-repentis; Rhizoctonia* spp.; *Colletotrichum graminicola; Helminthosporium* spp.; *Microdochium nivale; Pseudocercosporella herpotrichoides;* Mildews, *Erysiphe graminis* f.sp. *tritici; Sclerophthora macrospora;* Ear Molds, Gibberella ear mold, *Gibberella zeae; G. saubinetti;* Aspergillus ear rot, *Aspergillus flavus; A. parasiticus;* Diplodia ear rot, *Diplodia maydis; D. macrospora;* Fusarium ear rot, *Fusarium moniliforme; F. monilif.* var. *subglutinans;* Leaf Diseases: Eye spot, *Kabatiella zeae;* Gray leaf spot , *Cercospora zeae-maydis; C. sorghi* var. *maydis;* Anthracnose leaf blight, *Colletotrichum graminicola;* Northern corn leaf blight, *Exserohilum turcicum;* Southern corn leaf blight, *Bipolaris maydis;* Common rust, *Puccinia sorghi; P. maydis;* Southern rust, *Puccinia polysora; Dicaeoma polysorum;* Head smut, *Sphace-* lotheca reiliana; Common smut, *Ustilago maydis;* Carbonum leaf spot, *Helminthosporium carbonum;* Stalk Rots: Fusarium stalk rot, *Fusarium moniliforme;* Gibberella stalk rot, *G. zeae;* Pythium stalk rot, *Pythium aphanidermata;* Anthracnose stalk rot, *Colletotrichum graminicola; Glomerella graminicola; C. tucumanensis;* Diplodia stalk rot, *Diplodia maydis; D. zeae-maydis; Sphaeria maydis; S. zeae; Stenocarpella maydis; Macrodiplodia zeae; D. macrospora; G. saubinetti;* Stewart's wilt & leaf blight, *Erwinia stewartii;* Miscellaneous Fungal Diseases: *Septoria tritici; Septoria nodorum;* etc.

Mammalian Fzo proteins, Fzo homologs, mitofusins, nucleic acids encoding such proteins, and functional derivatives thereof, are further used in screening assays to identify therapeutic agents that act by, for example, preferentially promoting the loss of mitochondria from, blocking a step in the cell cycle of, or causing the death of undesirable cells such as cancer cells and viral-infected cells by modulating or inhibiting a mitofusin function or activity. In other embodiments, mammalian Fzo homologs, mitofusins and functional derivatives thereof are used in screening assays to identify therapeutic agents useful for treating a mitochondrial disease, wherein such agents enhance a mitofusin function or activity and thereby promote intermitochondrial complementation and/or recombination. That is, it is expected that some mitochondrial deficiencies can be corrected or at least ameriolated by promoting mitochondrial fusion by agents that enhance mitofusin functions or activities.

itochondrial diseases include, by way of example and not limitation, chronic neurodegenerative disorders such as Alzheimer's disease (AD) and Parkinson's disease (PD); auto-immune diseases; diabetes mellitus, including Type I and Type II; mitochondria associated diseases, including but not limited to congenital muscular dystrophy with mitochondrial structural abnormalities, fatal infantile myopathy with severe mtDNA depletion and benign "later-onset" myopathy with moderate reduction in mtDNA, MELAS (mitochondrial encephalopathy, lactic acidosis, and stroke) and MIDD (mitochondrial diabetes and deafness); MERFF (myoclonic epilepsy ragged red fiber syndrome); NARP (Neuropathy; Ataxia; Retinitis Pigmentosa); MNGIE (Myopathy and external ophthalmoplegia; Neuropathy; Gastro-Intestinal; Encephalopathy), LHON (Leber's; Hereditary; Optic; Neuropathy), Kearns-Sayre disease; Pearson's Syndrome; PEO (Progressive External Ophthalmoplegia); Wolfram syndrome DIDMOAD (Diabetes Insipidus, Diabetes Mellitus, Optic Atrophy, Deafness); Leigh's Syndrome; dystonia; stroke; schizophrenia; progressive joint disorders, such as osteoarthritis; and hyperproliferative disorders, such as cancer, tumors and psoriasis.

unctional derivatives of Fzo homologs and mitofusins are used for target validation of mitochondrial diseases; for example, antisense nucleic acids are used to inhibit expression of a Fzo homolog or mitofusin in a cultured cell line, and the biochemical or biological effects of such down-regulation are measured in order to confirm that reduced activity of the Fzo homolog or mitofusin will result in the predicted desired result, e.g., enhanced or decreased mitochondrial stability or cytotoxicity.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Example 1

Isolation and Genetic Mapping of fzo Mutations

Flies were grown on standard cornmeal molasses agar media at 25° C. All visible markers and balancer chromosomes were as described in Flybase (1996) *Nucl. Acids Res.* 24:53–56 (flybase.bio.indiana.edu) unless otherwise noted. The $fzo^1$ allele was isolated in a screen for ethyl methanesulfonate (EMS) induced recessive male sterile mutations. The $fzo^2$ allele was isolated in an EMS screen essentially as described in Lin et al. (1996) *Devel.* 122:1331–1341, except that mutagenized chromosomes were tested for failure to complement $fzo^1$. One new allele, $fzo^2$, was identified from 1799 mutagenized third chromosomes screened.

Deletion Mapping. The chromosomal location of the $fzo^1$ allele was initially identified by deletion mapping. The deletions Df(3R)M95A (94D; 95A3) and Df(3R)EB6 (94C2-5; 94E3; Mohler et al. (1995) *Devel.* 121, 237–247). The Df(3R)P2O 12 kb deletion was generated by the mobilization and imprecise excision of a lethal $ry^+$ marked P element in 94E3-5 associated with the $cnc^{03871}$ allele as follows. Flies transheterozygous for $cnc^{03781}$ and a TM3, Sb chromosome carrying the Δ2-3 transposase insert (Reuter et al. (1993) *Dros. Inf. Serv.* 72, 78) were crossed to ry e bar3 tx/TM3, Sb flies. F1 $cnc^{03781*}$/ry e bar3 tx males which had lost the P(ry+) and therefore had $ry^-$ eyes were crossed to e $fzo^1$/TM3, Serfemales. F2 $cnc^{03781*}$/e $fzo^1$ males were tested for the fzo phenotype, and stocks of new alleles were recovered by crossing together male and virgin female $cnc^{03781*}$/TM3, SerF2 siblings. From among approximately 200 $ry^-$ chromosomes tested, two deletions failing to complement $fzo^1$ were identified. Molecular breakpoints of the smaller deletion, Df(3R)P2O were mapped by Southern hybridization analysis using standard methods. Df(3R)P2O failed to complement mutations in cnc and was therefore not homozygous viable.

Recombination Mapping. The $fzo^1$ mutation was mapped by recombination to 0.5 cM distal of $hh^{bar3}$ and 0.5 cM proximal of $pnt^{07825}$ as follows. For initial meiotic mapping, females heterozygous for an e $fzo^1$chromosome and a ru h th st $p^p$ cu sr ca chromosome were crossed to ru h th st $p^p$ cu sr Bsb/TM3 or ru h th st cu e Pri ca/TM3 males. Male progeny with markers indicating single recombination events were selected for each interval and individually crossed to three e $fzo^1$/TM3 females to score fzo and make stocks of the recombinant chromosomes with TM3. The $fzo^1$ mutation mapped between e and ca, roughly 9 cM distal to e.

To localize $fzo^1$ further, $p^p$ e $fzo^1$/$hh^{bar3}$ tx females were crossed to e $hh^{bar3}$ tx/TM3 males and recombinant male progeny crossed individually to e $fzo^1$/TM3 females to score fzo and make stocks with TM3.$fzo^1$ mapped 0.58±0.17 cM distal to $hh^{bar3}$, based on 227 recombinants between $hh^{bar3}$ and tx.

The $fzo^1$ mutation was further localized by recombination with respect to restriction fragment length polymorphisms (RFLPs) in the interval between $hh^{bar3}$ and a $ry^+$ marked P element insertion in the pointed gene associated with the pnt$^{07825}$ allele. Briefly, females transheterozygous for ry$^{506}$ hh$^{bar3}$ fzo$^1$ (parental chromosome 1) and ry$^{506}$ pnt$^{07825}$ (parental chromosome 2) were crossed to ry$^{506}$ e hh$^{bar3}$ tx/TM3 males. Recombinant F1 Sb$^+$ progeny that were phenotypically either hh$^{bar3-}$ ry$^+$ or hh$^{bar3}$ $^+$ ry appeared at a frequency of 31 per 2995 flies, indicating that hh$^{bar3}$ and pnt$^{07825}$ were 1.04±0.18 cM apart. Males representing each of these two reciprocal recombinant classes were crossed individually to e fzo$^1$/TM3 females to score fzo on the recombinant chromosomes and to construct stocks with TM3. The fzo$^1$ mutation mapped in the center of the interval, 0.5 cM distal to hh$^{bar3}$ and 0.5 cM proximal to pnt$^{07825}$, in agreement with complementation of fzo$^1$ by Df(3R)EB6 but not by Df(3R)M95A.

RFLP Mapping. The fzo$^1$ mutation was further localized by RFLP mapping to an 11 kb region defined by polymorphic XbaI and EcoRI sites on an existing genomic phage walk as follows. RFLPs between the two parental chromosomes were identified using Southern blot analysis. Standard molecular biology techniques were used throughout this work, and DNA fragments were purified with a QIAquick kit (QIAGEN) as per the manufacturer's instructions. Genomic DNA was isolated from flies homozygous for parental chromosome 1 as well as from flies transheterozygous for parental chromosomes 1 and 2 (the P element insertion on parental chromosome 2 was a recessive lethal). The parental genomic DNAs were digested separately with 34 standard four-, five-, and six-cutter restriction enzymes, electrophoresed, blotted, and hybridized with several different radiolabeled DNA fragments from the distal third of a 90 kb genomic walk (Mohler et al. (1991) Mech. Devel. 34:3–10). At least one RFLP between the two parental chromosomes was detected for each probe. Genomic DNA was isolated from 35 recombinant stocks (either from homozygotes or from flies transheterozygous for the recombinant chromosome and parental chromosome 1). These DNAs were digested with the restriction enzymes previously shown to have polymorphic sites in the region, blotted, and probed with the appropriate fragments. Analysis of linkage between these molecular markers and fzo$^1$ defined the region of the fzo$^1$ mutation to be an 11 kb region between a polymorphic XbaI site at +11 and a polymorphic EcoRI site at +22 on the genomic phage walk of Mohler et al. (1991). The XbaI and EcoRI RFLPs segregated from fzo$^1$ in one and two of the 35 recombinants, respectively.

Example 2

Fzo is Required for Spermatoqenesis and Male Fertility in Drosophila

Fertility was determined by placing individual flies in yeasted vials with three males or virgin females as appropriate and scoring the presence or absence of larvae after seven days at 25° C. Progeny of tested females were counted. At least ten individual males and four individual females for each of the allelic combinations fzo$^1$/fzo$^1$, fzo$^1$/fzo$^2$, fzo$^1$/Df(3R)P2O, and fzo$^2$/Df(3R)P2O, as well as heterozygous sibling classes fzo/TM3 or Df(3R)P2O/TM3 were tested. (The fzo$^2$ chromosome carried a secondary lethal and could not be made homozygous.)

The effects of fzo$^1$ and fzo$^2$ mutations on viability were tested by crossing five individual females of each of the above allelic combinations to Df(3R)P2O/TM3 males at 25° C. and comparing numbers of fzo/Df progeny to total progeny. Progeny were collected for nine days after eclosion began.

Two EMS-induced alleles, fzo$^1$ and fzo$^2$, were characterized as described above. fzo$^1$/fzo$^1$, fzo$^1$/fzo$^2$, fzo$^1$/Df(3R) P2O, and fzo$^2$/Df(3R)P2O flies showed identical phenotypes, suggesting that both mutations are strong loss of function alleles. The severity of the phenotype was consistent among all spermatids in all testes observed. The fzo$^1$ and fzo$^2$ mutations did not noticeably affect female fertility or overall viability of the animal.

Mitochondria undergo dramatic morphogenetic changes during spermatid differentation in Drosophila (Fuller, 1993, "Spermatogenesis" In The Development of Drosophila, Bate et al, eds., Cold Spring Harbor Press, Cold Spring Harbor, N.Y., pp. 71–147. In early postmeiotic spermatids, mitochondria aggregate beside each haploid nucleus and fuse into exactly two giant mitochondrial derivatives that wrap around each other to form a spherical structure called a Nebenkern. The Nebenkern resembles an onion slice when viewed in cross section by transmission electron microscopy (TEM); the term "onion stage" thus refers to early round spermatids.

Spermatogenesis in fzo mutant male flies was examined by light and electron microscopy as follows. For light microscopy, testes from various fzo genotypes as well as from wild type Oregon R flies were dissected in TB1 buffer (7 mM K$_2$HPO$_4$, 7 mM KH$_2$PO$_4$ [pH 6.7], 80 mM KCl, 16 mM NaCl, 5 mM MgCl$_2$, 1% PEG-6000), opened with forceps to allow spillage of contents, placed under cover slips, and examined immediately by phase contrast microscopy with a Zeiss Axiophot microscope. To check for a mitochondrial membrane potential, 10 µg/ml rhodamine 123 was included in the dissection buffer and samples examined under epifluorescence.

For ultrastructural analysis by transmission electron microscopy, testes were dissected in TB1 and immediately placed in fixative (2% glutaraldehyde, 1% paraformaldehyde, 0.1M sodium phosphate or sodium cacodylate buffer [pH 7]). After overnight fixation, samples were washed in 0.1% phosphate or cacodylate buffer for 15 minutes and stained with 1% osmium tetroxide in the same buffer for two hours. Testes were washed three times in water, stained for 1 hour in 1% uranyl acetate, washed three times in water and dehydrated through an ethanol series (30%, 50%, 70%, 95%, 100%). After five minutes in 1:1 ethanol: propylene oxide and five minutes in propylene oxide, samples were embedded in Spurr's resin and polymerized overnight at 60° C. Thin sections (80–90 nm) were cut with a Reichert-Jung microtome, placed on Formvar-coated slot grids, and examined on a Phillips 410 transmission electron microscope.

Mutations in fzo result in defects in mitochondrial fusion during Nebenkern formation in post-meiotic early round spermatids. In wild type testes, mitochondria in each haploid spermatid aggregate beside the nucleus and fuse into a Nebenkern, a phase-dark spherical structure consisting of two interwrapped mitochondrial derivatives as viewed by TEM. In fzo mutant males, mitochondria aggregate in early haploid spermatids, forming somewhat misshapen Nebenkerns as viewed by phase contrast microscopy, but fail to fuse into two giant mitochondria. Instead, many smaller mitochondria appear to wrap around each other at the onion stage as viewed by TEM. Despite the prior defects in fusion, mitochondria unfurl and elongate in fzo mutants. At the early elongation stage, unfurling mitochondria in fzo mutants appear fragmented compared to wild type as seen by phase contrast microscopy. At the late elongation stage, two elongating mitochondrial derivatives per spermatid are seen in wild type. In contrast, many elongating mitochondria are associated with each haploid nucleus in fzo. Cross sections through wild type elongating spermatids viewed by TEM reveal two mitochondrial derivatives associated with each axoneme; the major derivative contains electron dense paracrystalline material while the minor does not. Each axoneme in fzo mutant males is associated with a large number of mitochondrial derivatives, with roughly half containing the paracrystalline material characteristic of major derivatives.

The defects in fzo mutant spermatids thus appear to be specific for mitochondrial fusion, as mitochondrial aggregation, membrane wrapping, and elongation all occur (although the unfused mitochondria do not elongate the full axonemal length because they lack sufficient membrane material). In addition, spermatid mitochondria in fzo mutants take up the dye rhodamine 123 in amounts similar to wild type, indicating presence of a membrane potential and suggesting that fzo mutations probably do not grossly affect respiration.

Example 3

Sequence Analysis of fzo cDNA Clones

Isolation of cDNAs. cDNA clones corresponding to transcripts from the fzo region were isolated from a testis cDNA library as follows. Radiolabeled EcoRI restriction fragments corresponding to +5 to +22 on the genomic walk were used to probe a λ-ZAP (Stratagene) testis cDNA library. Eighteen positive cDNA clones of various lengths were shown by Southern hybridization analysis to be from the same transcription unit. The seven longest cDNAs were 2.4 kb and had identical restriction maps. One of these was mapped to genomic DNA by Southern hybridization and, consistent with restriction mapping analysis, seemed to have no detectable introns. This cDNA was sequenced on both strands by the dideoxy chain termination method using the ABI PRISM™ dye terminator cycle sequencing system (Perkin-Elmer). T3 or T7 primers were used on the intact cDNA or dropout subclones, and 19- or 20-mer oligonucleotides were synthesized to prime sequencing runs through any remaining gaps. Representative members of each shorter cDNA class were restriction mapped, partially sequenced, and shown to be truncated versions of the longer class.

Amino Acid Sequence Analysis. The representative fzo cDNA (2399 bp) was sequenced fully on both strands and shown to have a complete open reading frame (ORF) comprising 718 amino acids, flanking AT-rich sequences and a single consensus translational start site. The cDNA ORF nucleotide sequence was translated in silico (that is, an algorithm was used to transform the nucleotide sequence into the corresponding amino acid sequence using the universal genetic code) using DNA Strider software. Analysis of the Fzo predicted protein with the BLOCKS program indicated similarity to the dynamin family in the vicinity of the P-loop, a motif found in nucleotide-binding proteins and designated as the G1 GTPase motif (Bourne et al., (1991) *Nature* 349:117–127).

Example 4

Expression Constructs Comprising fzo

To confirm that the transcription unit from which the fzo cDNA was prepared corresponds to fzo, a 4 kb genomic fragment containing the candidate locus, plus 1 kb of sequence upstream and approximately 500 bp of sequence downstream of the cDNA, was introduced into flies by P element mediated germline transformation as follows.

A 3 kb genomic fragment was isolated from an XhoI/XbaI digestion of phage D14 DNA (which corresponds to +3 to +16 on the genomic walk) and subcloned into the $w^+$-marked P element transformation vector pCaSpeR4 (Thummel and Pirrotta (1992) *Dros. Inf. Serv.* 71, 150) to make plasmid pKH2. The 2.4 kb EcoRI restriction fragment from phage D14 had previously been subcloned into pUC9 to make construct D5-19; a 1 kb XbaI/EcoRI fragment was isolated from a digestion of D5-19 and subcloned into pKH2 to make pKH3fzo$^+$. The resulting 4 kb insert in the pKH3fzo$^+$ rescue construct contained the genomic region of the full length fzo cDNA plus approximately 1 kb 5' and 500 base pairs 3'.

Plasmid pKH3fzo$^+$ and a plasmid encoding the Δ2-3 constitutively active transposase (the enzyme that directs P element mobilization) were mixed in a 3:1 molar ratio to a final DNA concentration of 0.4 mg/ml and injected into y $w^{67}$ or $w^{1118}$ embryos. Three independent fzo$^+$ insertions, one on the second chromosome and two on the third, were isolated from the progeny of 32 fertile injectees. An additional insertion on the second chromosome was obtained by mobilizing one of the third chromosome insertions with the TM3, Sb Δ2-3 transposase source.

To test for rescue, all four independent fzo$^+$ insertions were crossed into w; fzo mutant backgrounds by independent assortment for the second chromosome insertions and by recombination onto a hh$^{bar3}$ fzo$^1$ chromosome and then independent assortment for the third chromosome insertions, which were tested for rescue only of allelic combinations with fzo$^1$. A single copy of any of four independent transgene insertions fully restored fertility and normal mitochondrial morphogenesis to fzo$^1$/fzo$^1$, fzo$^1$/Df(3R)P2O, and fzo$^1$/fzo$^2$ males (and also fzo$^2$/Df(3R)P2O males, for the second chromosome insertions).

Example 5

Site-Directed Mutagenesis of fzo and Retransformation with Mutant fzo Transgenes To introduce mutations into the Fzo predicted GTP-binding domain, a 1.8 kb XbaI/BamHI restriction fragment (representing the first two thirds of the fzo coding region) from the pKH3fzo$^+$ germline transformation construct (see above) was subcloned into Bluescript SK-. Using standard methods, mutagenesis was performed with oligonucleotides having the sequences 5'-ACCTCAAATGGAACTAGTGCCGTGATC-3'; (SEQ ID NO:25), and 5'-TACTCMCAATCTATGGGATMG-3'; (SEQ ID NO:26).

The former (SEQ ID NO:25) exchanges AA for CT at nucleotides corresponding to those at positions 369–370 in the fzo cDNA, introducing a SpeI restriction site and changing the encoded amino acid at position 99 from a lysine to a threonine. The latter (SEQ ID NO:26) replaces a G with a T at nucleotide 819, eliminating a ClaI restriction site and changing the encoded amino acid at position 249 from an arginine to a leucine. Mutagenized constructs were selected by virtue of the above mentioned altered restriction sites. In like fashion, the mutation K110T was introduced into a fzo-encoding nucleic acid.

For each mutagenized construct, a 1.8 kb XbaI/BamHI restriction fragment was subcloned back into the 10 kb XbaI/BamHI vector fragment from plasmid pKH3fzo$^+$ to create two new germline transformation constructs, pKH3fzo$^{K99T}$ and pKH3fzo$^{R249L}$, which were injected into fly embryos as described in preceding Examples. In both of these constructs, the XbaI and BamHI restriction sites used for the final subcloning were regenerated during the ligation step. In addition, the reading frame remained unchanged at the mutagenesis and subcloning sites, as shown by detection of mutant proteins with anti-Fzo[605-718] antibodies, which only recognize epitopes that are encoded by regions 3' to the sites of ligation and mutagenesis and which thus require translation in the correct reading frame upstream (5') therefrom.

To test for rescue of the mutant phenotype by the fzo$^{K99T}$ and fzo$^{R249L}$ mutant transgenes, respectively, appropriate crosses were made to introduce separately the eight and five independent second chromosome transgene insertions into fzo mutant backgrounds. To test for any dominant effect, appropriate crosses were made to obtain males with one wild type copy of fzo and as many as four (fzo$^{K99T}$) or six (fzo$^{R249L}$) different copies of the mutated transgenes.

Conserved residues in the GTPase domain are required for Fzo function but not for targeting of the protein to mitochondria. Mediation of mitochondrial fusion by Fzo appears to require the predicted GTPase activity. Missense mutations (K99T and R249L) in the fzo transgene that alter conserved residues (lysine-99 and arginine-249, respectively) required in other GTPases for guanine nucleotide binding were introduced into the fzo transgene construct. For the fzo$^{K99T}$ and fzo$^{R249L}$ transgenes, respectively, none of the eight and five independent insertions on the second chromosome (in one copy or two, for those that were viable as homozygotes) were able to restore fertility or sperm motility to fzo$^1$/fzo$^1$, fzo$^1$/Df(3R)P2O, or fzo$^2$/Df(3R)P2O mutant males. In two copies, the fzo$^{K99T}$ transgene did not detectably improve the subcellular mutant phenotype, while the fzo$^{R249L}$ transgene appeared to allow some mitochondrial fusion. In a wildtype background, neither of the mutant transgenes impaired fertility or mitochondrial fusion; thus, neither mutant Fzo protein seems to act in a negative dominant mutant in this system. Fzo$^{K99T}$ and Fzo$^{R249L}$ mutant proteins were properly localized to spermatid mitochondria with wild type timing of appearance and disappearance.

The fzo$^{K99T}$ and fzo$^{R249L}$ mutations are recessive. Analogous mutations in mammalian dynamins cause dominant negative phenotypes when expressed in tissue culture cells; formation of macromolecular dynamin ring-shaped complexes appears to require GTP binding by all subunits. In contrast to dynamins, Fzo molecules may act individually or form complexes in which only some subunits must bind GTP for proper assembly or function.

Example 6

Expression of fzo in Primary Spermatocytes

RNA in situ Hybridization. For in situ hybridization to testes, digoxygenin-labeled RNA probes representing both the fzo cDNA sense and antisense strands (primed with T7 or T3 primers on a linearized cDNA construct) were made and submitted to alkaline hydrolysis (1 hour) as described in the Genius 4 RNA Labeling Kit user's guide (Boehringer Mannheim). Paraformaldehyde fixation of freshly dissected testes was as in Tautz (1989) *Chromosoma* 98:81–85 except no heptane or methanol was used. Subsequent treatment was as in Gonzalez (1994) "Techniques for studying mitosis in *Drosophila*" In *The Cell Cycle: A Practical Approach,* R. Brookes and P. Fantes, eds.: IRL, Oxford University Press), pp. 143–175, except 50 µg/ml heparin was included in the hybridization solution (HS); hybridization and early washes were at 65° C., and the secondary antibody was preadsorbed to *Drosophila* embryos and diluted 1:2000. Mounted preparations were examined under Nomarski optics with a Zeiss Axiophot microscope.

The fzo message, which hybridizes to and is detected by the antisense RNA probe, was highly expressed in pre-meiotic primary spermatocytes during their growth period but was not detectable at earlier stages in germline stem cells or mitotically dividing spermatogonia. The transcript persisted in meiotic cells but was not detectable in differentiating spermatids. The transcript was present in both fzo$^1$/fzo$^1$ and fzo$^2$/Df(3R)P2O testes. A control sense-strand sense fzo RNA probe did not hybridize in cells of any stage.

Example 7

Fusion Proteins Derived from Fzo and Antibodies Thereto

Production of a Fzo Fusion Protein. An expression construct that encodes and directs the production of a fusion protein containing a 6-histidine (6×His) tag, an amino acid sequence that binds Nickel (Ni), and the carboxy terminal 115 amino acids of Fzo was prepared as follows. A 0.5 kb BamHI/HindIII restriction fragment from the fzo cDNA1 (the HindIII site is from the Bluescript SK-multiple cloning site) was subcloned into vector pQE30 (QIAGEN). Expression of the fusion protein was induced, protein was harvested under denaturing conditions, and the 6×His/Fzo fusion protein was purified on a Ni-NTA column with imidazole elution as described in the QIAexpressionist manual (QIAGEN). Aliquots from each column fraction were electrophoresed on an SDS-polyacrylamide gel and stained with Coomassie Blue. Fractions with the highest degree of purity and highest concentration of the fusion protein were dialyzed in 1.5 M urea, 0.1 M Na phosphate, 0.01 M Tris-HCl, and 500 mM NaCl, pH 7.

Generation of Antibodies to Fzo Amino Acid Sequences. After dialysis, precipitated fusion protein was emulsified in complete Freund's adjuvant and injected into rabbits; standard schedules were followed for booster injections and serum collections (Berkeley Antibody Company, Richmond Calif.). The fusion protein formed a precipitate at urea concentrations below 4 M. Approximately 500 mg and 250 mg of the fusion protein were used for initial and booster injections, respectively.

Western Blots. Protein extracts were electrophoresed in 10% SDS-polyacrylamide gels and transferred to nitrocellulose filters in methanol buffer using standard methods. Testis extracts were prepared by placing freshly dissected testes into a solution containing 8 M urea, 0.1 M sodium phosphate, and 0.01 M Tris-Cl, pH 7 and mixing thoroughly until all proteins had dissolved. One volume of SDS-PAGE sample buffer was added, and the samples were then boiled for 15 minutes and spun at top speed in a microcentrifuge for ten minutes. Eight testes' worth of extract supernatant was loaded in each lane. Whole fly extracts were prepared by homogenizing flies in the above urea solution, with further treatment as above. One fifth of a fly's worth of extract was loaded per lane.

Filters were blocked in Blotto with 0.1% Tween 20 and incubated for two hours at room temperature in either control (preimmune) or anti-Fzo[604-718] serum (fourth bleed) diluted 1:1200, or mouse monoclonal anti-actin antibody (Amersham) diluted 1:100, in the blocking solution. Subsequent washes, incubation with horseradish peroxidase-conjugated secondary antibodies, and detection were performed as described in the ECL Western Blotting manual (Amersham). The secondary antibodies were diluted 1:7000 (anti-rabbit IgG) or 1:2000 (anti-mouse IgG).

Immunofluorescence. Fly testes were prepared for immunofluorescence staining as described in Hime (1996) *J. Cell Sci.* 109:2779–2788. The resulting slides were incubated overnight at 4° C. in preimmune or anti-Fzo$^{604-718}$ serum (fourth bleed) diluted 1:150 in PBTB (phosphate-buffered saline with 0.1% Triton X-100 and 3% bovine serum albumin), washed four times at room temperature in PBTB, and incubated for one hour at 37° C. in FITC-conjugated anti-rabbit IgG (Jackson Labs) diluted 1:200 in PBTB (0.5 mg/ml RNAse was included for samples to be later stained with propidium iodide). Slides were washed 4×10 minutes in PBTB and mounted in 85% glycerol, 2.5% N-propyl gallate. For some samples, 1 μg/ml DAPI (Sigma) was included in the second PBTB wash after incubation in secondary antibody; for others, 1 μg/ml propidium iodide was included in the mounting medium. Samples were examined using epifluorescence on a Zeiss Axiophot microscope; images were collected with a Photometrics cooled CCD camera (courtesy of Bruce Baker). Emissions from different fluorochromes on the same sample were collected separately and overlaid using Adobe Photoshop.

Antibodies raised against a fusion protein containing the C-terminal 115 residues of Fzo detected a wide doublet in Western blots of wild type testis extracts. The Fzo protein was partially resistant to extraction and denaturation and under standard denaturing conditions ran predominantly in streaky globs at an apparent molecular weight of 67 kD. When subjected to additional boiling and denaturants, some of the protein shifted up to a smoother band at an apparent molecular weight of 82 kD, the predicted size for Fzo. The wide Fzo doublet was greatly reduced in fzo$^1$ and fzo$^2$/Df(3R)P2O mutant testes and, as expected, increased in testes from wild type flies carrying six copies of a fzo$^+$ transgene.

Very low levels of Fzo or a cross-reacting protein with the same mobility pattern were apparent in extracts from whole adult agametic males, indicating expression in somatic tissues. Similar low levels of this protein were seen in agametic females, ovaries, and embryos of all stages and were unaffected in fzo$^2$/Df(3R)P2O whole male extracts. However, in fzo$^1$/fzo$^1$ males, the Fzo protein is highly expressed in somatic tissues despite its downregulation in fzo$^1$/fzo$^1$ testes. The fzo$^1$ mutation therefore appears to affect tissue specific expression of Fzo. Extracts from whole wild type males carrying six copies of the fzo$^+$ transgene showed more Fzo protein than agametic males but considerably less than fzo$^1$/fzo$^1$ males. Fzo may normally be expressed weakly in somatic tissues; it is therefore possible that Fzo is required elsewhere in addition to the testis and that the fzo$^1$ and fzo$^2$ alleles cause loss of function in the male germline only. Alternatively, the weakly-expressed somatic protein could be a Fzo isoform or an unrelated cross-reacting protein.

The Fzo protein is associated with mitochondria in early spermatids during a short time period that spans mitochondrial fusion. The anti-Fzo$^{604-718}$ antiserum stained onion stage Nebenkerns brightly in wild type spermatids but was undetectable or present at greatly reduced levels in fzo$^1$/fzo$^1$ or fzo$^2$/Df(3R)P2O testes, respectively. A wild type fzo transgene in a fzo$^1$/fzo$^1$ mutant background restored detectable Fzo protein to the Nebenkern.

The Fzo protein was associated with mitochondria in wild type spermatids during a narrow developmental window corresponding to the time that Fzo function is required. Mitochondria align on the spindle equator throughout meiotic divisions; however, the Fzo protein was not detected associated with mitochondria until the end of meiosis, during telophase II. In post-meiotic haploid spermatids, Fzo was associated with aggregating mitochondria and was detected at highest levels associated with onion stage Nebenkerns. The Fzo protein was detected at lower levels associated with early elongation-stage mitochondrial derivatives and was not detected associated with more elongated mitochondria. In testes from flies carrying multiple different copies of the fzo$^+$transgene, the anti-Fzo antibody stained mitochondria much more brightly but with a similar time course to wild type. Preimmune serum did not stain wild type testes.

Example 8

Fzo Homologs and Mitofusins

The fzo transcription unit encodes a predicted protein of 718 amino acids (see SEQ ID NO:2 and GenBank accession number U95821). The predicted Fzo protein sequence was compared using the BLAST program to nucleotide sequences in GenBank and dbEST translated in all reading frames. Significant homology was detected to predicted proteins in mammals (*Homo sapiens, Mus musculus* and *Rattus norvegica*), worms (*Caenorhabditis elegans*), and yeast (*Saccharomyces cerevisiae*). Predicted proteins encoded by Fzo homologs were themselves subjected to homology searches as above. Alignments were done with the help of the CLUSTALW program using DNAstar software.

ORFs from *C. elegans* (U29244, ORF 14) and *S. cerevisiae* (Z36048) encode complete predicted proteins with 28% and 19% identity to Fzo, respectively. The *S. cerevisiae* predicted protein is itself 24% identical to a partial predicted protein from the thermophilic bacterium *Caldocellum saccharolyticum* (L18965 ORF 6), which is 11% identical to Fzo. As the latter cells lack mitochondria, the *C. saccharolyticum* protein is unlikely to play the role of a mitofusin perse in its natural activties, although it may play a role in the fusion of bacterial cells and may function as a mitofusin if contacted with mitochondria. The *C. saccharolyticum* protein is, in any event, a Fzo homolog as defined herein.

Genetic and biochemical analysis in *S. cerevisiae* confirms that the yeast homolog, fzo1p, is required for mitochondrial fusion (Hermann et al. (1998), *J. Cell Biol.* 143:359–374; Rapaport et al., (1998) *J. Biol. Chem.* 273:20150–20155). Depletion of Fzo1p activity from yeast cells rapidly blocks mitochondrial fusion and causes defects in mitochondrial distribution. In time, loss of Fzop1 activity leads to cells depleted in mitochondrial DNA (as determined by DAPI staining) and a petite growth phenotype. Moreover, the yeast Fzo homolog is associated with mitochondria as an integral membrane protein. As with the *Drosophila* gene, mutations in the predicted GTPase domains of the yeast fzo homolog destroys the ability of the protein to mediate mitochondrial fusion. The yeast Fzop1 protein is thus both a Fzo homolog and a mitofusin.

Partial or complete reading frames for mouse, rat and human Fzo homolog proteins were initially assembled in silico from ESTs. These sequences are used to prepare probes and PCR primers that are used to isolate full-length cDNAs according to methods known in the art. The mammalian species have two forms of related Fzo homologs (which are designated as mitofusins herein due to their localization to mitochondria) which are referred to herein as Mfn1 and Mfn2. Furthermore, Mfn1-specific sequences are present on two RNA species of different sizes, suggesting that two related but distinct forms of the Mfn1 protein are expressed in some instances. These isoforms of Mfn1 are referred to as Mfn1a and Mfn1b.

Example 9

Expression Constructs Encoding Human Fzo Homologs and Mitofusins

The BLAST search with the predicted Fzo protein identified a human cDNA clone from which a human fetal brain EST (GenBank T06373) is derived. The human cDNA clone was obtained from the American Type Culture Collection (ATCC, Manassas, Va.) and its nucleotide sequence was determined according to standard methods.

The predicted amino acid sequences of hMfn1 and hMfn2 are provided in the sequence listing. A plasmid comprising a hMfn2 cDNA sequence was obtained as a gift from the Kazusa DNA Research Institute (Chiba, Japan), and a cDNA encoding hMfn2 was prepared therefrom as follows. The plasmid was used as a template for polymerase chain reaction (PCR) in order to generate a hMfn2-encoding cDNA. Two synthetic oligonucleotides, having the following sequences, were used as primers in the PCR reactions:

5'-GACTCTAGAATGTCCCTGCTCTTCTCTCG (SEQ ID NO:27), and
5'- GCCCACTATCTGCTGGGCTGCAGG (SEQ ID NO:28).

In the above descriptions of the PCR primers, sequences corresponding to hMfn2 sequences are underlined and the start (ATG) and stop (CTA, i.e., the reverse complement of TAG) codons for hMfn2 are doubly underlined. SEQ ID NO:27 includes an XbaI restriction site (5'-TCTAGA) near its 5' end.

The Taq-amplified PCR products were directly ligated ligated into an expression vector, pCR®2.1 (Invitrogen, Carlsbad, Calif.) that has ends complementary to Taq-amplified PCR products. The resultant plasmid, pCR-hMFN2 is both an expression construct (when transcription is driven by the T7 promoter, RNA molecules that encode hMFN2 are produced) and an antisense construct (when transcription is driven by the lacZ promoter, which is oriented in the opposite orientation from that of the T7 promoter, the resulting RNA molecules have the reverse complement of a sequence that encodes hMFN2).

Transient overexpression of hMfn2, or of an hMfn2-GFP fusion protein that has a N-terminal deletion that removes GTPase motif G1 (motifs G2, G3 and G4 are retained in this fusion protein) in mamallian cells caused severe aberrations in mitochondrial morphology and distribution leading to colapse into a few mitochondrial aggregates per cell if expression was allowed to continue unchecked. This ability to promote mitochondrial fusion is one activity or function of mitofusins that is used to evaluate the properties of derivatives of Mfn proteins and to screen for or assay agents thought to enhance, modulate or inhibit mitofusin functions or activities. Expression of the hMfn2-GFP fusion protein in these cells did not affect the morphology of other cellular compartments, i.e., the Golgi network, microtubule network and endoplasmic reticulum, these other compartments having been visualized with antibodies directed to markers specific therefor (beta-COP, alpha-tubulin and PDI, respectively).

Example 10

Functional Derivatives of Human Fzo Homologs and Mitofusins

Preparation of hMfn2 Fusion Proteins. Plasmid pCR-hMfn2 was digested with XhoI and EcoRI and electrophoresed on an agarose gel, and the restriction fragment, which had the predicted the predicted size of 2.3 kb, was purified from the gel using standard methods. Plasmid pEGFP-N1 (Clontech, Palo Alto, Calif.) was digested with XhoI and EcoRI and mixed with the purified hMfn2-encoding restriction fragment. T4 DNA ligase was added to the mixture, which was incubated at 4° C. overnight. Competent *E. coli* cells were transformed with the ligation mix, and several transformants were independently isolated. The expression construct DNA contained in transformants was purifed as in the preceding Examples and restriction mapped.

An isolate comprising an hMfn2-GFP expression construct was identified by virtue of having the predicted restriction map, and this construct was used in further studies. In the hMfn2-GFP fusion protein, the most carboxy terminal amino acid residue of hMfn2 (R757) is joined to a short linker sequence (ILQSTVPRARDPPVAT, SEQ ID NO:29), which is in turn directly joined to the most amino terminal amino acid (M1) of the GFP portion of the protein. When transiently expressed in murine 10T1/2 fibroblasts, the hMfn2-GFP fusion protein localized to mitochondrial compartments, as demonstrated by fluorescence microscopy.

A hMfn2-myc fusion protein was prepared in similar fashion. In this derivative, the hMfn2 amino acid residues at the amino terminal end of the fusion protein are linked to a short polypeptide sequence that corresponds to an epitope derived from the human c-myc protein. Antibodies specific for this polypeptide epitope are available from a number of commercial sources and may be used in the detection (or affinity purification) of myc fusion proteins. During transient expression in COS-7 cells, the hMfn2-myc fusion protein co-localized with a fluorescent fusion protein (ATP-translocase-GFP) known to localize to mitochondria.

These mitofusin fusion proteins, and others like them, are tested for other biochemical and biological activities and functions (other than mitochondrial localization) of mitofusins using methods and compositions described in the present disclosure, as well as those described in Bereiter-Hahn et al., 1994, *Microscopy Research and Technique* 27:198–219; Kuroiwa et al., 1994, *Microscopy Research and Technique* 27:220–232; Hales et al., 1997, *Cell* 90:121–129; Hermann et al., 1998, *J. Cell Biol.* 143:359–373; and Rapaport et al., 1998, *J. Biol. Chem.* 273:20150–20155. Mitochondrial fusion and megamitochondria formation can be monitored according to a variety of methods known in the art using commercially available reagents such as, for example, MitoTracker™ CMXRos (Molecular Probes, Eugene, Or.; Karbowski et al., 1999, *Biochim. Biophys. Acta* 1449:25–40).

A variety of functional derivatives of mitofusins, having different activities and functions of the mitofusins from which they are derived, are prepared, identified and characterized in this manner. Functional derivatives of one type are used as guides to prepare related functional derivatives. For example, deletion analysis of the mitofusin fusion proteins (see following section) is used to identify portions of mitofusin proteins that are necessary for mitofusin activties and functions such as, by way of non-limiting example, mitochondrial localization; ability to complement fzo and fzo1p mutations in *D. melanogaster* and *S. cerevisiae,* respectively; and the ability to promote mitochondrial fusion in vivo or in vitro, etc. Synthetic oligopeptides, having amino acid sequences corresponding to the omited segments of mitofusin deletion derivatives that lack a specific activity or function, are tested for their capacity to enhance, modulate or inhibit the activity or function. Oligopeptides (or other derivatives) having such properties are functional derivatives of mitofusins.

Deletion of Sequences Associated with the Transmembrane Domain. In order to see if carboxy terminal amino acid residues of hMfn2 are required for mitochondrial location of hMfn2, the following experiments were carried out. The hMfn2 reading frame includes an NcoI site that straddles a codon (ATG) that encodes M603 of hMfn2. In the GFP expression vector pEGFP (Clontech), the portion of the expression vector that encodes the GFP polypeptide has an NcoI site that straddles the start codon for the GFP reading frame. When combined, these two NcoI sites are in-frame with respect to each other.

An expression construct comprising the nucleotide sequences for hMfn2-GFP was digested with NcoI and mixed with NcoI-digested pEGFP DNA. The mixture was treated with DNA Ligase, and used to transform cells. Several transformants were independently selected, and expression construct DNA contained therein was purifed. The DNAs were restriction mapped, and an isolate having the predicted restriction map was identified, designated phMfn2-GFPΔNcoI(a), and used for further studies.

The reading frame in phMfn2-GFPΔNcoI(a) results in the deletion of the amino terminus (amino acids 604–757) of hMfn2 and the fusion of M603 of hMfn2 to V2 of GFP. The putative transmembrane domain of hMfn2 includes amino acids 618–637 and is thus entirely deleted in the hMfn2-GFPΔNcoI(a) gene product.

The hMfn2-GFPΔNcoI(a) gene product was transiently expressed in mouse 10T1/2 fibroblasts, and the distribution of the fluorescent fusion protein in the cells was examined by fluorescence microscopy. Unlike the intact hMfn2-GFP fusion protein, which localizes to mitochondria, the hMfn2-GFPΔNcoI(a) fusion protein was distributed throughout the cytosol. Thus, all or some of amino acid residues 604–757 of hMfn2 are required for its proper insertion into the mitochondrial membrane.

The hMfn2-GFPΔNcoI(a) gene product is one example of a functional derivative of a mitofusin protein that is a hydrophilic and water soluble, rather than membrane-bound, protein. The hMfn2-GFPΔNcoI(a) gene product retains the predicted GTPase domain that mutational analysis demonstrates is required for mitofusin function (Example 5), and is thus expected to retain the biochemical functions associated with the predicted GTPase domain. Because hydrophilic and water-soluble proteins are easier to incorporate into screening assays, including high throughput screening assays, in which reactions and binding events necessary for such assays take place in the aqueous phase, such water-soluble functional derivatives of mitofusins have distinct advantages over hydrophobic, membrane-bound forms of mitofusins.

Another functional derivative of hMfn2 is prepared as follows. The above-described plasmid encoding the hMfn2-GFP fusion protein is partially digested with NcoI that has been diluted 10× or 100× in 1× reaction buffer for varying periods of time. The reactions are stopped by addition of phenol and or heat inactivation of NcoI (65° C., 10 min.) and the partically digested DNAs are ethanol precipitated according to standard methods. The resuspended DNAs, as well as molecular weight markers and a control NcoI digest that has been allowed to go to completion, are electrophoresed on agarose gels that are stained with ethidium bromide. Partial digests are identified, and the corresponding DNAs are diluted and treated with DNA ligase. The ligation mixtures are used to transform cells, and several colonies are independently isolated. The plasmid DNAs present in the isolated transformants are prepared and restriction mapped, and a deletion derivative that has lost the short DNA fragment present between the two NcoI sites in the hMfn1 reading frame is identified. The gene product encoded by this deletion derivative is designated hMfn2-GFPΔNcoI(b). In the hMfn2-GFPΔNcoI(b) gene product, amino acids 600–612 (having the sequence MVTGLASLTSRTS, SEQ ID NO:14) are deleted from the full-length hMfn2 sequence. The deleted amino acids are immediately adjacent to, and on the amino terminal side of, the transmembrane domain and may be necessary for localization of hMfn2 to the mitochondrial membrane. The localization of the hMfn2-GFPΔNcoI(b) gene product is determined in the same manner as was that of the hMfn2-GFPΔNcoI(a) gene product.

The above-described deletion derivatives of hMfn2, hMfn2-GFPΔNcoI(a) and hMfn2-GFPΔNcoI(b), are tested for their ability to function as dominant negative forms of hMfn2 as were the above-described missense mutants. The NcoI deletion derivatives of hMfn2 are expected to retain the ability to bind other components of the molecular machinery that mediates mitochondrial fusion, but do not localize to the mitochondrial membrane. Accordingly, other mitochondrial fusion components that bind to the NcoI deletion derivatives are directed away from their site of action within or at the surface of mitochondria and are thus unable to mediate mitochondrial fusion or do so with a limited efficiency.

Many mitochondrial proteins have an amino terminal sequence that is necessary for or stimulates mitochondrial localization. However, hMfn2(aa1–96)-GFP, a fusion protein in which amino acids 1–96 of hMfn2 are fused to GFP (expressed from an expression construct prepared in similar fashion as that expressing hMfn2-GFPΔNcoI), did not localize to mitochondria and was distributed throughout the cytosol. Further, a fusion protein in which amino acids 97–757 of hMfn2 are fused to a c-myc eptiope, hMfn2(aa97–757)-myc, was effectively localized to mitochondria.

Example 11

Hybridization Analyses of Human Mitofusin (hMfn) Genes

DNAs comprising sequences specific for hMfn1 or hMfn2 were radiolabelled and used in Northern blot analyses of mRNA isolated from a variety of human tissues. The results indicate that there are two transcripts (approximately 4 and 6.5 kb in size as estimated by comparison to molecular weight standards) comprising hMfn1-specific sequences in a variety of tissues. Expression of hMfn1 was most pronounced in heart and pancreas. In contrast, a single transcript approximately 5 kb in size was detected by hMfn2-specific probes, and its expression was most pronounced in heart and muscle.

Labelled hMfn1 and hMfn2 probes were also used to probe filters onto which human RNAs from a variety of healthy and diseased cell types, and from tissues prepared at various times of development, in order to determine if the genes are differentially expressed in different diseases or at different stages of development. These experiments indicate that hMfn1 is preferentially expressed in certain cancer cell lines and in fetal tissue.

Example 12

Informational and Structural Features of Fzo Homologs

Fzo homologs, including mitofusins, comprise a variety of distinguishing informational features (e.g., nucleotide and amino acid sequences) and structural features (e.g., predicted coil or transmembrane regions). These features include the following.

GTPase Motifs. The *Drosophila* fzo gene encodes a conserved predicted GTPase required for mitochondrial fusion during spermatogenesis and associated with mitochondria only during a short time spanning the fusion event. Fzo contains four motifs common to virtually all known GTPases and conserved among Fzo homologs from mammals to yeast. Fzo is the first protein to be assigned a function in this new family of large predicted transmembrane GTPases. Within this family, the GTPase domain placement, motif spacing, and protein size (but not overall sequence) suggest a possible distant relationship with dynamins, which play a central biomechanical role in endocytic membrane trafficking.

Mutations predicted by analogy to diminish guanine nucleotide binding (see preceding Examples) do not affect localization of Fzo to mitochondria but eliminated or reduced its ability to mediate mitochondrial fusion. The $fzo^{K99T}$ mutation, predicted to disallow key hydrogen bonds with the GTP β and γ phosphates, caused a severe loss of function phenotype. In contrast, the $fzo^{R249L}$ mutation appeared to allow some mitochondrial fusion to occur, though not enough to restore normal sperm morphology or motility. The Fzo arginine-249 is part of the G4 motif and is predicted to contact the ribose moiety of GTP. Nearly all known GTPases have a lysine at positions analogous to $Fzo^{R249}$ perhaps the conservative change to arginine in Fzo and its higher eukaryotic homologs reflects somewhat decreased importance of this residue for stable nucleotide binding. Mutations analogous to $fzo^{R249L}$ in H-ras reduce but do not eliminate GTP binding. It is possible that $Fzo^{R249L}$ may have residual GTP affinity, explaining its partial function.

The region of highest homology between the Fzo, human fetal brain (50% identity to Fzo), *C. elegans* (49%), and *S. cerevisiae* (20%) predicted proteins is a 186 amino acid region containing four completely conserved signature motifs found in virtually all GTPases. The *C. saccharolyticum* predicted protein also contains these motifs. Outside the individual motifs there is no significant similarity to any known GTPase. However, the spacing between the GTPase motifs, their N-terminal placement in Fzo and homologs, and the overall predicted protein size are reminiscent of the dynamin family (Warnock and Schmid, 1996 *BioEssays* 18:885–893). The G2 motif (Bourne et al., 1991 *Nature* 349:117–127) consists only of a conserved threonine and has not been defined in dynamins. Both the Fzo and dynamin families have a conserved threonine exactly 20 residues beyond the G1 motif that may represent G2. Exemplary consensus amino acid sequences in the Fzo homologs are described in Table 2.

Consensus Sequences for GTPase Domains in Fzo Homologs

| GTPase Motif | Consensus Sequence | Sequences in Fzo and Fzo Homologs | | SEQ ID NO: |
|---|---|---|---|---|
| G1 | MKVAFFGRTSNGKSTVINA | | | 30 |
| | | MKVAFFGRTSNGKSAVINA | (Fzo) | 31 |
| | | MKVVFFGRTSNGKSTTINA | (C. elegans) | 32 |
| | | MKVAFFGRTSSGKSTVINA | (hMnf1) | 33 |
| | | MKVAFFGRTSNGKSTVINA | (hMnf2) | 34 |
| G3 | DLVLMDSPGTDVTTELD | | | 35 |
| | | DVVLMDTPGVDVTAQLD | (Fzo) | 36 |
| | | DVVILDSPGVDLSPEFD | (C. elegans) | 37 |
| | | DLVLVDSPGTDVTTELD | (hMfn1) | 38 |
| | | DLVLMDSPGTDVTTELD | (hMfn2) | 39 |
| G4 | PNIFILNNRWDASAS | | | 40 |
| | | PNLFILNNRWDKASS | (Fzo) | 41 |
| | | PNVFILNNRWDASAA | (C. elegans) | 42 |
| | | PNIFILNNRWDASAS | (hMnf1) | 43 |
| | | PNIFILNNRWDASAS | (hMnf2) | 44 |

Outside the GTPase motifs, Fzo and its homologs have moderate homology at the amino acid level (30%, 21%, and 19% identity between Fzo and the human fetal brain, *C. elegans*, and *S. cerevisiae* homologs, respectively). However, the following results indicate that the Fzo homologs share several predicted structural features.

Transmembrane Domains and Flanking Regions. The sequences of Fzo and homologs were analyzed for predicted transmembrane domains and regions likely to form coiled coils with the TMpredict program and the COILS program, respectively. The Compute pI/Mw program on the ExPASy Molecular Biology Server was used to calculate predicted isoelectric points. All of the Fzo homologs have a predicted transmembrane domain near the C terminus embedded in a large (~35 amino acids) uncharged region interrupted by one to three basic residues.

Although transmembrane domains of proteins are sometimes difficult to identify based on homology alone, the sequences of hMfn1 and hMfn2 are particularly homologous to each other. These sequences, IIVGGVIWKTIGWKLLSV (SEQ ID NO:45) in hMfn1 and LWGGVVWKAVGWR-LIAL (SEQ ID NO:46) in hMfn2, are thus useful for identifying mitofusins from mammals, particularly primates.

All the Fzo homologs have a predicted coiled coil region located to the C-terminal side of a predicted transmembrane domain, although the C terminal coiled coil probability in the *S. cerevisiae* homolog is lower than in other homologs. The *C. elegans* and *S. cerevisiae* homologs have strongly predicted coiled coil regions near their N termini. The analogous region in Fzo has a lower coiled coil probability (0.23) but is strikingly similar to the *C. elegans* homolog in its α helical projection, showing clear acidic, hydrophobic, and basic/polar faces. All four homologs are acidic overall between the N terminus and the transmembrane domain, with predicted isoelectric points (pI) near 5, and are basic in the C terminal tail, with predicted pIs near 9.

Example 12

Control of Mitochondrial Morphology by Human Mitofusin

Material and Methods

Identification of human Mitofusin genes. Human Mfn1 sequences were identified by searching the human genome and EST databases. Appropriate primers were designed to amplify the ORF bearing part of the predicted hMfn1 message by OneStep RT-PCR (Qiagen) from 50 ng of human heart poly-A$^+$-RNA (Clontech, Palo Alto, Calif.). The resulting 2.2 kb cDNA fragment was recovered, subcloned into pCR2.1TOPO (Invitrogen, Carlsbad, Calif.) and sequenced. Human Mfn2 was identified as the KIAA0214 cDNA (Nagase et al.(1996) DNA Res. 3:321–329, 341–354) by searching the GenBank database with the *Drosophila* Fzo protein sequence using TBLASTN. The hMfn2/KIAA0214 cDNA clone (GenBank Accession No. D86987) is 4.55 kb in size and covers the entire 2274 bp ORF as well as additional sequences of the 5'- and 3'-UTR.

Generation of expression constructs. The human Mfn1 coding region was excised with EcoRI from pCR2.1TOPO::hMfn1 and cloned into pEGFP-C2 (GFP-fusion constructs) or inserted into pIRES-GFP (Clontech, Palo Alto, Calif.) to generate express untagged Mfn1. GFP- or myc-tagged forms of hMfn2 were generated by amplification of the hMfn2 ORF using appropriate primers and Turbo-Pfu-polymerase (Stratagene, La Jolla, Calif.). PCR products were subcloned into pcDNA3A-myc/His (Invitrogen, Carlsbad, Calif.) or appropriate pEGFP expression vectors (Clontech, Palo Alto, Calif.) for N- or C-terminal GFP-fusion constructs. Deletion constructs were derived from these by dropping out fragments or using PCR to amplify defined regions of the hMfn2 cDNA. Missense mutations were introduced in hMfn2 using the Quickchange Mutagenesis kit (Stratagene, La Jolla, Calif.). The ANT-GFP expression construct (clone VLP32), and expression plasmids for HA-tagged human Drp1 and mutant Drp1$^{K38A}$ were used.

Cell culture and transfection. COS-7 cells, HeLa cells, and mouse 10T1/2 and LA fibroblasts were grown in DMEM supplemented with 10% fetal bovine serum and 100U/ml streptomycin, 100 U/ml penicillin. Cells were seeded on LabTekII glass slides and transfected using Super-Fect (Qiagen) per manufacturer's instructions. Pools of stably transfected cell populations expressing hMfn2-myc were prepared by incubating transfected COS-7 cells in DMEM+10% FBS and 0.8 mg/ml Geniticin, maintained in selection medium for several passages over a period of 10 weeks, then processed for immunochemistry.

Antibodies and indirect immunofluorescence. Primary antibodies were: mouse monoclonal anti-cytochrome C-oxidase I subunit 1:60 (anti-COXI, Molecular Probes), rabbit polyclonal anti-mouse Tfam 1:1000 (Larsson et al. (1998) *Nat Genet.* 18:231–236), mouse monoclonal anti-myc-9E10 1:40, mouse monoclonal anti-HA 1:500 (Covance, Richmond, Calif.), mouse monoclonal anti-protein disulfide isomerase 1:50 (anti-PDI; Sigma), rabbit polyclonal anti-β-COP 1:100 (Sigma) and mouse monoclonal anti-α-tubulin 4AI 1:100. Mitotracker Red CXRos (Molecular Probes) was used to label mitochondria per manufacturer's protocol. About 19–24 hours after transfection, cells were rinsed twice with Dulbecco's PBS (phosphate buffered saline), fixed with 4% formaldehyde/PBS for 15 minutes at room temperature, then rinsed three times and permeabelized for 15 minutes in PBTD (PBS with 0.1% Triton X-100 and 0.05% sodium deoxycholate), followed by 30 minutes block with PBTB (PBS with 0.1% Trition X-100 and 3% bovine serum albumin). Slides were incubated with primary antibody two hours at 37° C., rinsed four times with PBTB, incubated two hours at 37° C. in FITC-/TRITC/Rhodamine-conjugated anti-rabbit or anti-mouse IgG (Jackson Immunochemicals; 1:200 in PBTB), washed extensively in PBS, and examined by epifluorecence on a Zeiss Axiophot microscope. Images recorded by CCD camera (Princeton Instruments, Trenton, N.J.; IPLab Sofware, Spectrum Sofware Signal Analytics Corp.) and processed with Adobe (Adobe, Mountain View, Calif.) Photoshop.

Results

Two human genes encode Fzo homologs. Two human genes designated Mitofusin 1 and 2 (hMfn1 and hMfn2) encode homologs of *Drosophila* fzo. The human Mfn1 and Mfn2 predicted proteins had highest homology to *Drosophila* fzo protein in the N-erminal, predicted GTPase-domain. Overall, hMfn1 (741 amino acids) was 32% identical and 50% similar to *Drosophila* fzo protein, while hMfn2 (757 amino acids) was 33% identical and 54% similar to *Drosophila* fzo protein. The predicted hMfn1 and hMfn2 proteins were 60% identical and 77% similar to each other, with the most extensive homology in the predicted GTPase domain and the least conserved regions in the N- and C-terminal ends. Expressed sequence tags (ESTs) homologous to the hMfn1 and hMfn2 genes were also found in mouse, cow, *Xenopus* and zebrafish.

Mammalian Mitofusins associate with mitochondria. Human Mfn proteins co-localized with mitochondrial markers when expressed in stably transfected COS-7 cells (myc-tagged hMfn2) or after transient transfection with constructs encoding full-length hMfn2 protein fused to GFP in all cell types tested (HeLa, LA9, 10T1/2, COS-7). hMfn2 epitope tagged with myc and hMfn1 untagged ortagged with N-terminal GFP (GFP-hMfn1) also associated with mitochondria when expressed after transient transfection.

Expression of human Mfn proteins alters mitochondrial morphology. Mitochondrial morphology was dramatically altered in transiently transfected cells expressing hMfn2. The effect ranged from conversion of the normal dispersed distribution of punctate mitochondia to more reticular structures, to extensive perinuclear clustering. Perinuclear clustering of mitochondria was observed in over 90% of transiently transfected cells expressing either hMfn2-myc or hMfn2-GFP. Perinuclear clusters usually appeared to contain most of the mitochondria in the cell, based on counter-staining with an independent mitochondrial marker. The perinuclear clusters varied in size and shape from cell to cell, but were usually crescent-shaped aggregates or perinuclear rings of distinct fluorescent particles. Expression of C-terminal myc hMfn2, N-terminal GFP hMfn2, and untagged or C-terminal GFP-hMfn1 protein after transient transfection also resulted in perinuclear mitochondrial clustering. Mitochondrial morphology appeared unaffected in parallel control transient transfections with an ATP-translocase-GFP construct, which drives overexpression of a protein of the inner mitochondrial membrane. Although the shape of the clustered mitochondrial mass in hMfn2-GFP-transfected cells was reminiscent of the Golgi apparatus, counterstaining with a Golgi marker revealed that the Golgi apparatus and the mitochondrial cluster in hMfn2-GFP expressing cells did not co-localize. Transient expression of hMfn2-GFP did not grossly affect the structure and subcellular localization of the Golgi apparatus, microtuble cytoskeleton, or endoplasmic reticulum, based on co-staining with anti-β-COP, anti-α-tubulin or anti-PDI.

The hMfn2 GTPase is not required for mitochondrial clustering. Mitochondrial clustering after transient overexpression of hMfn2 may not be due to excessive mitochondrial fusion activity in transfected cells. Conserved residues in the predicted GTPase domain of *Drosophila* fzo protein and yeast Fzo1p are required for mitochondrial fusion. A corresponding missense mutation in the predicted GTPase domain of hMfn2 (hMfn2$^{K1097}$-GFP) did not reduce mitochondrial clustering or association of the fusion protein with mitochondria, suggesting that the predicted GTPase activity is not responsible for mitochondrial clustering. In addition, N-terminal deletion constructs encoding human Mfn2 or mouse Mfn1 lacking parts of the predicted GTPase domain (deletion of hMfn2 from N terminus through G1; deletion of mMfn1 from N terminus through G3, still showed mitochondrial clustering upon transient expression.

Residues near the hMfn2 C-terminus, however, were required for mitochondrial clustering. Both the Mfn1 and Mfn2 predicted proteins have a high probability of forming a coiled coil structure in the C-terminal 20 to 30 amino acids based on the algorithms of Lupas and Wolf (Wolf et al. (1997) *Protein Sci.* 6:1179–1189), a feature conserved in *Drosophila* Fzo. Truncated hMfn2 lacking the last C-terminal 54 residues and fused to GFP (hMfn2$^{1-703}$-GFP co-localized with the mitochondrial marker COXI when expressed in COS-7, HeLa or 10T1/2 cells after transient transfection. However, mitochondrial clustering was strongly reduced in hMfn2$^{1-703}$-GFP transfected cells compared to cells transfected with full-length hMfn2-GFP, suggesting a role for the predicted coiled-coil domain in perinuclear mitochondrial clustering.

A GTPase dependent hMfn function in mitochondrial morphology revealed by altering activity of the predicted mitochondrial fission protein Drp1. In vegetatively growing yeast cells, mitochondrial fusion is balanced by ongoing mitochondrial fission mediated by action of the dynamin related protein Dnm1. To test if effects of overexpression of hMfn on mitochondrial fusion might be masked by rapid mitochondrial fission, we co-expressed hMfn fusion protein and a mutant form of the mammalian dynamin related protein Drp1 predicted to dominantly interfere with function of endogenous Drp1 activity. Expression of hMfn2 caused formation of long strings and networks of mitochondria in the presence of the dominant mutant human Drp1$^{K38A}$ protein. Formation of the mitochondrial strings and networks was blocked by a point mutation in a critical GTPase motif of hMfn2, suggesting that they require Mfn GTPase activity.

Transiently expressed, HA-tagged wild type human Drp1 protein was distributed ubiquitously in the cytoplasm of COS-7 cells transiently transfected with HA-Drp1 and the mitochondrial marker ATP-Translocase-GFP (ANT-GFP). Expression of wildtype HA-Drp1 after transient transfection did not visibly affect mitochondrial morphology compared to transfection with the ANT-GFP mitochondrial marker alone. Co-expression of wild-type HA-Drp1 with wild-type hMfn2-GFP resulted in mitochondrial clustering resembling that observed after expression of Mfn2-GFP alone. HA-Drp1 partially co-localized with the clustered mitochondria.

A point mutation in a key GTPase residue of Drp1 resulted in an altered subcellular distribution of the Drp1 protein. HA-Drp1$^{K38A}$ appeared in dot-like structures after transient transfection, in contrast to the diffuse cytoplasmic distribution observed for the wild type fusion protein. In addition, transient transfection with the HA-Drp1$^{K38A}$ construct affected mitochondrial morphology, resulting in formation of perinuclear aggregates.

When hMfn2-GFP was co-expressed with GTPase-mutant HA-Drp1$^{K38A}$, mitochondria formed thin GFP-positive tubules extending from the perinuclear mitochondrial cluster toward the cell periphery. In addition, many cells displayed an interconnected network of tubular GFP-positive structures. The GFP-positive threads and networks were mitochondria based on co-staining with anti-COXI.

Formation of mitochondrial threads and networks depended on a wild type hMfn2-GTPase domain. Mutation of a key predicted GTPase residue in hMfn2 blocked formation of mitochondrial threads and networks upon co-transfection with Drp1$^{K38A}$, resulting in mitochondrial clusters indistinguishable from those in cells expressing hMfn2-GFP alone. The HA-tagged Drp1$^{K38A}$ mutant fusion protein appeared in dot-like structures in the hMfn2$^{K1097}$-GFP/HA-Drp1$^{K38A}$ doubly transfected cells but did not appear associated with the perinuclear mitochondria.

An internal region of Mfn2 is sufficient for mitochondrial targeting. Little is known about the pathways governing targeting of nuclear encoded proteins to the mitochondrial outer membrane. To identify sequences required for association of hMfn proteins with mitochondria, we tested a variety of hMfn2 fusion proteins expressed after transient transfection. Although analysis of the hMfn2 sequence by PSORT and MITOPROT indicated a predicted mitochondrial targeting signal at the N-terminus, the N-terminal 96 amino acids of hMfn2 was neither sufficient nor necessary for association with mitochondria. hMfn2$^{97-757}$-myc protein co-localized with mitochondrial markers and caused perinuclear clustering of mitochondria when expressed after transient transfection.

A 93 amino acid internal fragment of hMfn2 containing the predicted transmembrane domain (TM) and C-terminal flanking sequences was sufficient to target a GFP reporter to mitochondria, although a small amount of GFP fluorescence also appeared throughout the cell. Expression of hMfn2$^{610-703}$-GFP did not cause perinuclear mitochondrial clustering. The predicted transmembrane domain contains two stretches of hydrophobic residues separated by one (fzo) or two (Mfns) charged residues. This bipartite hydrophobic region is followed by a predicted alpha-helical region characterized by a conserved stretch of charged residues. When the bipartite hydrophobic region was deleted from otherwise full-length hMfn2-GFP, the protein no longer localized to mitochondria, as expected if the region acted as a transmembrane domain. Although the hydrophobic region is relatively short, it appeared important, as changing three hydrophobic amino acids into charged residues abolished mitochondrial targeting of the full-length fusion protein (hMfn2$^{RRE}$-GFP). Instead, the GFP reporter was distributed diffusely in the cytoplasm. GFP fluorescence also appeared high in the nucleus for the hMfn2$^{RRE}$-GFP and hMfn2$^{\Delta 608-643}$-GFP constructs, either because the cells were thicker over the nuclear region or because the mutant hMfn2$^{RRE}$-GFP was preferentially localized to the nucleus. In contrast, substituting other hydrophobic residues for these same amino acids (construct hMfn2$^{AAL}$-GFP) did not affect mitochondrial targeting. Mutations in the AH-region that changed conserved charged residues to non-charged residues did not abolish either targeting of the hMfn2-GFP fusion protein to mitochondria or formation of perinuclear mitochondrial clusters. Although many precursor proteins are imported into mitochondria by an amino-terminal cleavable pre- or targeting sequence, internal targeting sequences have been described for other nuclear encoded mitochondrial outer membrane proteins, including mammalian OMP25, which also has a C-terminal transmembrane domain containing region capable of correct mitochondrial localization.

The functional similarities between the yeast and *Drosophila* Fzo proteins suggest that mammalian fzo homologs also mediate mitochondrial fusion. Consistent with this hypothesis, we found that expression of the human Mfn2 protein by transient transfection in cells also expressing a dominant interfering form of Drp1 caused formation of long strings and extensive networks of mitochondria. Formation of the mitochondrial cables and networks was dependent on a wild type GTPase domain of hMfn2, suggesting a central role for GTPase activity in the mechanism of action of the Mfn proteins, as in their homologs yfzo1 and *Drosophila* fzo. The mitochondrial networks closely resembled those formed by mitochondrial fusion in dnm1 mutant yeast cells due to unopposed activity of the Mfn homolog yFzo1p. Dnm1 encodes a yeast homolog of human Drp1 required for mitochondrial fission.

In mammalian cells, as in yeast, the size and morphological arrangement of mitochondria is due to a dynamic balance between Mfn dependent mitochondrial fusion and Drp1 dependent mitochondrial fission. Overexpression of Drp1$^{K38A}$ may interfere with mitochondrial fission by blocking function of the endogenous Drp1 protein. Accordingly, the formation of mitochondrial cables and networks observed in the doubly transfected cells appears to have resulted from excessive mitochondrial fusion due to overexpression of Mfn protein combined with decreased mitochondrial fission due to interference by the mutant Drp1.

In cells transfected with wild type hMfn alone or co-transfected with hMfn2 and wild type Drp1, continuous mitochondrial fission may mask the effects of overexpression of hMfn by rapidly cleaving up any long mitochondria that form. In this case, a second, GTPase independent role of hMfn proteins in mitochondrial morphogenesis or function may be revealed in the perinuclear aggregation of mitochondria. The predicted C terminal coiled coil domain and other parts of the Mfn protein could be involved in mechanisms essential for normal mitochondrial distribution, such as transport or positioning of mitochondria or lipid metabolism of mitochondrial membranes. Disruption of the mouse kinesin motor protein KIF5B also results in perinuclear mitochondrial clustering. Likewise, transient overexpression of the mammalian mitochondrial outer membrane protein OMP25 leads to perinuclear aggregation of mitochondria, possibly due to recruitment of synaptojanin 2A to mitochondria and local modulation of inositol phospholipid metabolism. Alternatively, overexpression of hMfn proteins could cause perinuclear clustering if the high levels of the protein expressed after transient transfection block mitochondrial import channels, causing defects in import or function of other mitochondrial proteins.

Biochemical analysis of the yeast Fzo 1p homolog indicated that the protein is anchored to the mitochondrial outer membrane with both its N-terminal GTPase domain and C-terminal ends exposed to the cytoplasm. If hMfns are associated with mitochondria via similar topology, the bipartite hydrophobic region could pass through the mitochondrial outer membrane and back out. The carboxy terminal predicted coiled-coil region (trimer-type for hMfn1; dimer-type for hMfn2) could form an integral part of the fusion mechanism, reminiscent of membrane fusion by influenza virus Hemagglutinin or the SNARE protein complex. If so, we propose that the Mfn GTPase domain displayed on the cytoplasmic face of the mitochondrial outer membrane could interact with the C-terminal coiled coil region to regulate mitochondrial fusion.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule comprising a sequence encoding a mitofusin 2 polypeptide wherein said mitofusin 2 comprises the amino acid sequence set forth in any one of SEQ ID NO:4; or SEQ ID NO:16.

2. The isolated nucleic acid of claim 1, wherein said nucleic acid comprises the sequence set forth in any one of SEQ ID NO:3; or SEQ ID NO:15.

3. An isolated nucleic acid molecule comprising a sequence encoding a mammalian mitofusin polypeptide comprising the amino acid sequence set forth in any one of SEQ ID NO:6; SEQ ID NO:14 or SEQ ID NO:16.

4. The isolated nucleic acid of claim 3, wherein said nucleic acid comprises a sequence set forth in any one of SEQ ID NO:5; SEQ ID NO:11; SEQ ID NO:13; SEQ ID NO:15; and SEQ ID NO:12.

5. An expression construct comprising a transcriptional initiation region functional in an expression host, a nucleic acid having a sequence of the isolated nucleic acid of claim 1 or claim 3 under the transcriptional regulation of said transcriptional initiation region, and a transcriptional termination region functional in said expression host.

6. An isolated cell comprising the expression construct of claim 5 integrated into the genome of said cell.

7. An isolated cell comprising a nucleic acid according to claim 1 or claim 3 as part of an extrachromosomal element or integrated into the genome of a host cell as a result of introduction of said expression cassette into said host cell, and the cellular progeny of said host cell.

8. A method for producing a mitofusin protein, said method comprising:

growing the cell of claim 6, whereby said mitofusin protein is expressed; and isolating said mitofusin protein essentially free of other proteins.

* * * * *

UNITED STATES PATENT AND TRADEMARK OFFICE
CERTIFICATE OF CORRECTION

| | | |
|---|---|---|
| PATENT NO. | : 6,953,680 B2 | Page 1 of 1 |
| APPLICATION NO. | : 10/117846 | |
| DATED | : October 11, 2005 | |
| INVENTOR(S) | : Fuller et al. | |

It is certified that error appears in the above-identified patent and that said Letters Patent is hereby corrected as shown below:

Col. 1, line 3, please insert:

-- FEDERALLY-SPONSORED RESEARCH OR DEVELOPMENT

This invention was made with Government support under contract HD029194 awarded by the National Institutes of Health. The Government has certain rights in this invention. --

Signed and Sealed this
Ninth Day of August, 2011

David J. Kappos
*Director of the United States Patent and Trademark Office*

SEQUENCE LISTING

<160> NUMBER OF SEQ ID NOS: 46

<210> SEQ ID NO 1
<211> LENGTH: 2399
<212> TYPE: DNA
<213> ORGANISM: Drosophila melanogaster

<400> SEQUENCE: 1

```
gagcaaaaca acatctacag ttgcctatat ttcataaata aatttgttaa cattttgta      60 atatctaatc ataatggcgg aatctgactc cggagaaagt acgtcgtcgg tgtcctcgtt     120
tatatcctca tcgtcgtctt cgcgattaag tgagtttgtg gacgcaaaga cagaactgca    180
ggatatatat cacgatttga gtaattacct gtccaatttc ctaaccattt tggaggagac    240
tgtcctctta aaagatcgac aaatgctgga gcacctgtgc gccttctcca gcagggtgga    300
ggccattgca aaggttcttt cacgtgatcg aatgaaggtg gcattttttg gacgcacctc    360
aaatggaaaa agtgccgtga tcaatgcact tctgcatgaa aaaatcctgc ccagcgccat    420
gggccatacc accagctgtt tttgtcaagt gcaagctaat ggctcgaatg aaaccgagca    480
```

-continued

| | |
|---|---|
| cgtaaaggtc gagcaggagg atgagcatat ggaactgagt gccctaagcc aactggccag | 540 |
| tgcacattct cctggggccc taaaaccctc aactctgctg caggtcaata tggccaagaa | 600 |
| ccgttgctcg atattggatt acgatgtggt tttgatggat acacctggag tggatgtaac | 660 |
| agcgcaactg gacgattgcc tagatagcta ctgcatggat gcggatgttt tcattctagt | 720 |
| tctcaacgcc gagtccactg tttcgcgcgt ggaaaggcag ttcttcaagg acgtggcatc | 780 |
| caaactctcg cgtccaaatc tctttatact caacaatcga tgggataagg ccagcagtct | 840 |
| ggagccggaa atggagcaga aggtaaagga tcagcatatg gaacgttgcg ttaacctgct | 900 |
| cgtggatgaa ttaggtgttt attcaactgc acaggaagcg tgggaaagga tctatcatgt | 960 |
| ttcagcactg gaggcattgc atataaggaa tggtcagatt acgaatccct cgggacaaac | 1020 |
| ccaacagcga tatcaggagt tctgcgtttt cgaaaatgat ttttcgaatt gcctcgcggt | 1080 |
| gtcagcgtta aaaccaaat ttggtccaca cttgctaagt gcgcagaaga tttttaaacca | 1140 |
| gttaaaatca actctgatat gcccttcat agagaaagta agtcgtctta cgatgagaa | 1200 |
| taaggagaga agagctaact tgaatgccga aatagaggac tggttaatac taatgcaaga | 1260 |
| ggatagagaa gcgcttcaat attgtttcga agaactgact gaaatgacac aaagagtagg | 1320 |
| tcggtgcgtt ttgagcgacc agataaaaac gttaataccc tcgtctgtgc tatcattctc | 1380 |
| gcaaccattt cacccggaat tcccagcaca aataggccag taccaacgct cgttatgtgc | 1440 |
| ccatttggat aaacttcttg aagatcgtgt ccttcaatgt ctctccatac ccctacaaag | 1500 |
| agaaatatta gatatagaga aagaaattgg gcttccgatc gccgagaact cttgcgattg | 1560 |
| gcaactaatc tacggcctgg attgccaatc ctatatgagt gactttcagc cagatcttag | 1620 |
| gttttcgattt tctttgggtt ttactgccct gtggcatcgc cttgaaggca acctaccgtt | 1680 |
| gcacgcaagt ccatttcgaa ttcaaaagtt acaaaatggt cacaagaaat gttcgcccct | 1740 |
| gccaccttta gttaacggaa accattggca gatgctggaa tctttggtga agtctaaagg | 1800 |
| tagcttgggc accgttttac tgagcgccat ggccatccgt tcgttcaact ggccaattgt | 1860 |
| attgatcctt ggtgggctcg tcggatcctt ttacatctac gagtacgccg cttggacaac | 1920 |
| tgccgcccaa gagcgaagtt tcaagagcca gtacgccagg ctcttgcaac aacgtctgcg | 1980 |
| gtcggatgtg cagcaaactg ttagcggttt tgagctccag ttgcgacagc acctggcaac | 2040 |
| ggtccgaaat tgctgggaag cccagtccaa tgagacactg aatgacctga cgtaaggac | 2100 |
| cgcggagctg accaaacaaa tacaatcgat ggaggtgttg cagctcagcc tgaagaagtt | 2160 |
| tcgggacaag ggacagctgc tggccagtcg gttgggagac tttcaagaga cctacttgac | 2220 |
| caagagctga caattatgag gggggttaca acaaattcta aatgttctta atagttttaa | 2280 |
| tttatttttg gttacctaat taagtattgt aattccgtta tgttacttag aaattttgta | 2340 |
| tgtatttggt tgaatatttt aaaatattaa acgattggtc ttcactactt taaagttaa | 2399 |

<210> SEQ ID NO 2
<211> LENGTH: 718
<212> TYPE: PRT
<213> ORGANISM: Drosophila melanogaster

<400> SEQUENCE: 2

Met Ala Glu Ser Asp Ser Gly Glu Ser Thr Ser Ser Val Ser Ser Phe
1               5                   10                  15

Ile Ser Ser Ser Ser Ser Arg Leu Ser Glu Phe Val Asp Ala Lys
        20                  25                  30

```
Thr Glu Leu Gln Asp Ile Tyr His Asp Leu Ser Asn Tyr Leu Ser Asn
         35                  40                  45

Phe Leu Thr Ile Leu Glu Glu Thr Val Leu Leu Lys Asp Arg Gln Met
 50                  55                  60

Leu Glu His Leu Cys Ala Phe Ser Ser Arg Val Glu Ala Ile Ala Lys
 65                  70                  75                  80

Val Leu Ser Arg Asp Arg Met Lys Val Ala Phe Phe Gly Arg Thr Ser
             85                  90                  95

Asn Gly Lys Ser Ala Val Ile Asn Ala Leu Leu His Glu Lys Ile Leu
            100                 105                 110

Pro Ser Ala Met Gly His Thr Thr Ser Cys Phe Cys Gln Val Gln Ala
            115                 120                 125

Asn Gly Ser Asn Glu Thr Glu His Val Lys Val Glu Gln Glu Asp Glu
130                 135                 140

His Met Glu Leu Ser Ala Leu Ser Gln Leu Ala Ser Ala His Ser Pro
145                 150                 155                 160

Gly Ala Leu Lys Pro Ser Thr Leu Leu Gln Val Asn Met Ala Lys Asn
                165                 170                 175

Arg Cys Ser Ile Leu Asp Tyr Asp Val Val Leu Met Asp Thr Pro Gly
            180                 185                 190

Val Asp Val Thr Ala Gln Leu Asp Asp Cys Leu Asp Ser Tyr Cys Met
            195                 200                 205

Asp Ala Asp Val Phe Ile Leu Val Leu Asn Ala Glu Ser Thr Val Ser
210                 215                 220

Arg Val Glu Arg Gln Phe Phe Lys Asp Val Ala Ser Lys Leu Ser Arg
225                 230                 235                 240

Pro Asn Leu Phe Ile Leu Asn Asn Arg Trp Asp Lys Ala Ser Ser Leu
                245                 250                 255

Glu Pro Glu Met Glu Gln Lys Val Lys Asp Gln His Met Glu Arg Cys
                260                 265                 270

Val Asn Leu Leu Val Asp Glu Leu Gly Val Tyr Ser Thr Ala Gln Glu
            275                 280                 285

Ala Trp Glu Arg Ile Tyr His Val Ser Ala Leu Glu Ala Leu His Ile
290                 295                 300

Arg Asn Gly Gln Ile Thr Asn Pro Ser Gly Gln Thr Gln Gln Arg Tyr
305                 310                 315                 320

Gln Glu Phe Leu Arg Phe Glu Asn Asp Phe Ser Asn Cys Leu Ala Val
                325                 330                 335

Ser Ala Leu Lys Thr Lys Phe Gly Pro His Leu Leu Ser Ala Gln Lys
            340                 345                 350

Ile Leu Asn Gln Leu Lys Ser Thr Leu Ile Cys Pro Phe Ile Glu Lys
            355                 360                 365

Val Ser Arg Leu Ile Asp Glu Asn Lys Glu Arg Arg Ala Asn Leu Asn
370                 375                 380

Ala Glu Ile Glu Asp Trp Leu Ile Leu Met Gln Glu Asp Arg Glu Ala
385                 390                 395                 400

Leu Gln Tyr Cys Phe Glu Glu Leu Thr Glu Met Thr Gln Arg Val Gly
                405                 410                 415

Arg Cys Val Leu Ser Asp Gln Ile Lys Thr Leu Ile Pro Ser Ser Val
            420                 425                 430

Leu Ser Phe Ser Gln Pro Phe His Pro Glu Phe Pro Ala Gln Ile Gly
            435                 440                 445

Gln Tyr Gln Arg Ser Leu Cys Ala His Leu Asp Lys Leu Leu Glu Asp
```

|     | 450 |     |     |     | 455 |     |     |     | 460 |     |     |
|-----|-----|-----|-----|-----|-----|-----|-----|-----|-----|-----|-----|

Arg Val Leu Gln Cys Leu Ser Ile Pro Leu Gln Arg Glu Ile Leu Asp
465                 470                 475                 480

Ile Glu Lys Glu Ile Gly Leu Pro Ile Ala Glu Asn Ser Cys Asp Trp
            485                 490                 495

Gln Leu Ile Tyr Gly Leu Asp Cys Gln Ser Tyr Met Ser Asp Phe Gln
            500                 505                 510

Pro Asp Leu Arg Phe Arg Phe Ser Leu Gly Phe Thr Ala Leu Trp His
            515                 520                 525

Arg Leu Glu Gly Asn Leu Pro Leu His Ala Ser Pro Phe Arg Ile Gln
530                 535                 540

Lys Leu Gln Asn Gly His Lys Lys Cys Ser Pro Leu Pro Pro Leu Val
545                 550                 555                 560

Asn Gly Asn His Trp Gln Met Leu Glu Ser Leu Val Lys Ser Lys Gly
                565                 570                 575

Ser Leu Gly Thr Val Leu Leu Ser Ala Met Ala Ile Arg Ser Phe Asn
            580                 585                 590

Trp Pro Ile Val Leu Ile Leu Gly Gly Leu Val Gly Ser Phe Tyr Ile
            595                 600                 605

Tyr Glu Tyr Ala Ala Trp Thr Thr Ala Ala Gln Glu Arg Ser Phe Lys
            610                 615                 620

Ser Gln Tyr Ala Arg Leu Leu Gln Arg Leu Arg Ser Asp Val Gln
625                 630                 635                 640

Gln Thr Val Ser Gly Phe Glu Leu Gln Leu Arg Gln His Leu Ala Thr
                645                 650                 655

Val Arg Asn Cys Trp Glu Ala Gln Ser Asn Glu Thr Leu Asn Asp Leu
                660                 665                 670

Asn Val Arg Thr Ala Glu Leu Thr Lys Gln Ile Gln Ser Met Glu Val
            675                 680                 685

Leu Gln Leu Ser Leu Lys Lys Phe Arg Asp Lys Gly Gln Leu Leu Ala
            690                 695                 700

Ser Arg Leu Gly Asp Phe Gln Glu Thr Tyr Leu Thr Lys Ser
705                 710                 715

<210> SEQ ID NO 3
<211> LENGTH: 2501
<212> TYPE: DNA
<213> ORGANISM: Drosophila melanogaster

<400> SEQUENCE: 3

```
atggcggcct acttgaaccg caccatctcg atggtgaccg ggcaaacggg ccccgccgac      60
gacgaccgtc acgcctcctc cacggacacg gtggacaaat ccggacccgg ttccccgcta     120
tcccggttca actcatcgct gcaacaatcc ggctccacaa tggccgccaa tctgctaccg     180
gaatcgcggc tctatcaatc caacgacaaa tcaccgctcc agatctttgt gcgcgccaaa     240
aagaagatca cgatatcta cggcgagatc gaggagtatg ccatgagac gaccaccttt     300 atcaacgccc tgcacgcgga agcggagatc gtggacaagg cggaacggga gctgttcgaa     360
agctatgtgt acaaggtggc ggccattcgc gaagtactgc agcgggatca catgaaggtg     420
gccttctttg acgcaccctc caacggcaag agctcggtga ttaatgccat gttgcgcgag     480
aagatcctgc ccagcggcat tgggcacacc acgaattgct tctgccaagt ggagggcagc     540
aatggcggcg aggcgtatct tatgacagag ggctccgagg agaagctaaa tgtggtgaac     600
atcaaacaac tggcgaatgc cttgtgccag gagaagctct gcgagagcag tttggtgcgc     660
```

-continued

```
atcttttggc cgagggaacg ctgcagcctg ctgcgcgacg atgtcgtctt tgtggactca    720
cctggtgtgg atgtgtcggc caatttggac gactggatcg ataaccattg cctgaacgcc    780
gatgtctttg tgctggtcct gaatgccgag tcaacgatga cgcgtgcgga aagcagttc     840 tttcacaccg tctcgcagaa gctaagcaag ccgaacatct tcatcctgaa caatcgctgg    900
gatgcgtcgg ccaacgagcc cgagtgccag gaatcggtta agtctcagca cacgaacgc     960 tgcatcgact tcctcaccaa ggagctaaag gtgagcaacg agaaggaggc ggccgaaagg   1020
gtattcttcg tttccgccag ggaaacgctg caggcgcgca tcgaggaggc caagggcaat   1080
ccgccgcaca tgggtgccat tgccgagggc tttcagatac gctacttcga gttccaggac   1140
ttcgagcgca agttcgagga gtgcatctcg cagagtgctg tgaaaacaaa gttccagcag   1200
cacagttcgc gcggcaagag tgtttcgggt gacatgaaat caatgttgga caacatttac   1260
gagcggatca ccatattccg caatctgaag caggaccaga agaacctgct caccgaacgc   1320
atccagggca cagagacgca gatgatgcag gttacgcggg aaatgaagat gaagatccac   1380
aacatggtcg aggaggtgga ggagaaggtg tcaaaggcgc tgaacgagga gatctggcgc   1440
ctgggcgtac tcattgacga gttcaatatg cccttccatc cggagcgttt ggtgctgaac   1500
atctacaaaa aggaattgaa tgcccatgtg gagagcggcc tggcagcaa tctgcgcgcc    1560 cgcctatcca tggccctggc catgaacgtc gagtccgccc agacggagat gaccgatcgc   1620
atgcacgccc tggtgcccaa cgagcagctc ctggccacca gcaccaagat ggtggtgcgc   1680
acgcagccct tcgagatgct ctactcactg aattgccaga acctctgcgc cgacttccag   1740
gaggatctgg agtttaagtt cagctgggggc attgcggcga tgatccagcg cttcaccggc   1800
aaggtgcgcg agcgcagcaa gaagggccag ccggcgctgg tcaatcgaca gagcagtatt   1860
ggagtgagtt tctacagtat agttgtgttg caccaccttt actatatctc tgccatcgaa   1920
tctcgttcac agcacagcgt atcgacgccg accacgacgc ccgtggaagc cactcctgtg   1980
tgcctgctgc ccgctcccgt tgtggctggc attacgcccg agcagctgtc gttgatctca   2040
cgcttcgcgg tgtcctccat tggatcgcag ggcaccgttg tggtctcgt cgtagccggt    2100 gtcatgctga aaactatcgg ctggcgtgtc ctggtgggcg tgggtgccct ctacggctgc   2160
atctacctgt acgagcgcct ctcgtggaca aattcagcca aggagcgaac gttcaagtcg   2220
cagtacgtgc gccatgccac caagaagctc aagatgattg tcgacctcac ctcggccaac   2280
tgcagccacc aagtgcagca ggaattgtcg agcacctttg cccgtttgtg ccgcacggtt   2340
gataccgcca ccacggacat gaatgatgag ctcaagacgc tggactcgca gctgaacatc   2400
ctggaggcga accagaagca attgaagctg cttcgcaaca aggccaacta caacagaacg   2460
agctggacat cttcgagcac aactatatat cgccgcagta g                       2501
```

<210> SEQ ID NO 4
<211> LENGTH: 832
<212> TYPE: PRT
<213> ORGANISM: Drosophila melanogaster

<400> SEQUENCE: 4

```
Met Ala Ala Tyr Leu Asn Arg Thr Ile Ser Met Val Thr Gly Gln Thr
  1               5                  10                  15

Gly Pro Ala Asp Asp Asp Arg His Ala Ser Ser Thr Asp Thr Val Asp
                 20                  25                  30

Lys Ser Gly Pro Gly Ser Pro Leu Ser Arg Phe Asn Ser Ser Leu Gln
         35                  40                  45
```

```
Gln Ser Gly Ser Thr Met Ala Ala Asn Leu Leu Pro Glu Ser Arg Leu
 50                  55                  60

Tyr Gln Ser Asn Asp Lys Ser Pro Leu Gln Ile Phe Val Arg Ala Lys
 65                  70                  75                  80

Lys Lys Ile Asn Asp Ile Tyr Gly Glu Ile Glu Tyr Val His Glu
                 85                  90                  95

Thr Thr Thr Phe Ile Asn Ala Leu His Ala Glu Ala Glu Ile Val Asp
            100                 105                 110

Lys Ala Glu Arg Glu Leu Phe Glu Ser Tyr Val Tyr Lys Val Ala Ala
        115                 120                 125

Ile Arg Glu Val Leu Gln Arg Asp His Met Lys Val Ala Phe Phe Gly
    130                 135                 140

Arg Thr Ser Asn Gly Lys Ser Ser Val Ile Asn Ala Met Leu Arg Glu
145                 150                 155                 160

Lys Ile Leu Pro Ser Gly Ile Gly His Thr Thr Asn Cys Phe Cys Gln
                165                 170                 175

Val Glu Gly Ser Asn Gly Gly Glu Ala Tyr Leu Met Thr Glu Gly Ser
            180                 185                 190

Glu Glu Lys Leu Asn Val Val Asn Ile Lys Gln Leu Ala Asn Ala Leu
        195                 200                 205

Cys Gln Glu Lys Leu Cys Glu Ser Ser Leu Val Arg Ile Phe Trp Pro
    210                 215                 220

Arg Glu Arg Cys Ser Leu Leu Arg Asp Asp Val Val Phe Val Asp Ser
225                 230                 235                 240

Pro Gly Val Asp Val Ser Ala Asn Leu Asp Asp Trp Ile Asp Asn His
                245                 250                 255

Cys Leu Asn Ala Asp Val Phe Val Leu Val Leu Asn Ala Glu Ser Thr
            260                 265                 270

Met Thr Arg Ala Glu Lys Gln Phe Phe His Thr Val Ser Gln Lys Leu
        275                 280                 285

Ser Lys Pro Asn Ile Phe Ile Leu Asn Asn Arg Trp Asp Ala Ser Ala
    290                 295                 300

Asn Glu Pro Glu Cys Gln Glu Ser Val Lys Ser Gln His Thr Glu Arg
305                 310                 315                 320

Cys Ile Asp Phe Leu Thr Lys Glu Leu Lys Val Ser Asn Glu Lys Glu
                325                 330                 335

Ala Ala Glu Arg Val Phe Phe Val Ser Ala Arg Glu Thr Leu Gln Ala
            340                 345                 350

Arg Ile Glu Glu Ala Lys Gly Asn Pro Pro His Met Gly Ala Ile Ala
        355                 360                 365

Glu Gly Phe Gln Ile Arg Tyr Phe Glu Phe Gln Asp Phe Glu Arg Lys
    370                 375                 380

Phe Glu Glu Cys Ile Ser Gln Ser Ala Val Lys Thr Lys Phe Gln Gln
385                 390                 395                 400

His Ser Ser Arg Gly Lys Ser Val Ser Gly Asp Met Lys Ser Met Leu
                405                 410                 415

Asp Asn Ile Tyr Glu Arg Ile Thr Ile Phe Arg Asn Leu Lys Gln Asp
            420                 425                 430

Gln Lys Asn Leu Leu Thr Glu Arg Ile Gln Gly Glu Thr Gln Met Met
        435                 440                 445

Gln Val Thr Arg Glu Met Lys Met Lys Ile His Asn Met Val Glu Glu
    450                 455                 460
```

```
Val Glu Glu Lys Val Ser Lys Ala Leu Asn Glu Ile Trp Arg Leu
465                 470                 475                 480

Gly Val Leu Ile Asp Glu Phe Asn Met Pro Phe His Pro Glu Arg Leu
            485                 490                 495

Val Leu Asn Ile Tyr Lys Lys Glu Leu Asn Ala His Val Glu Ser Gly
                500                 505                 510

Leu Gly Ser Asn Leu Arg Ala Arg Leu Ser Met Ala Leu Ala Met Asn
            515                 520                 525

Val Glu Ser Ala Gln Thr Glu Met Thr Asp Arg Met His Ala Leu Val
    530                 535                 540

Pro Asn Glu Gln Leu Leu Ala Thr Ser Thr Lys Met Val Val Arg Thr
545                 550                 555                 560

Gln Pro Phe Glu Met Leu Tyr Ser Leu Asn Cys Gln Asn Leu Cys Ala
                565                 570                 575

Asp Phe Gln Glu Asp Leu Glu Phe Lys Phe Ser Trp Gly Ile Ala Ala
            580                 585                 590

Met Ile Gln Arg Phe Thr Gly Lys Val Arg Glu Arg Ser Lys Lys Gly
                595                 600                 605

Gln Pro Ala Leu Val Asn Arg Gln Ser Ser Ile Gly Val Ser Phe Tyr
    610                 615                 620

Ser Ile Val Val Leu His His Leu Tyr Tyr Ile Ser Ala Ile Glu Ser
625                 630                 635                 640

Arg Ser Gln His Ser Val Ser Thr Pro Thr Thr Thr Pro Val Glu Ala
                645                 650                 655

Thr Pro Val Cys Leu Leu Pro Ala Pro Val Val Ala Gly Ile Thr Pro
            660                 665                 670

Glu Gln Leu Ser Leu Ile Ser Arg Phe Ala Val Ser Ser Ile Gly Ser
                675                 680                 685

Gln Gly Thr Val Gly Gly Leu Val Val Ala Gly Val Met Leu Lys Thr
    690                 695                 700

Ile Gly Trp Arg Val Leu Val Gly Val Gly Ala Leu Tyr Gly Cys Ile
705                 710                 715                 720

Tyr Leu Tyr Glu Arg Leu Ser Trp Thr Asn Ser Ala Lys Glu Arg Thr
                725                 730                 735

Phe Lys Ser Gln Tyr Val Arg His Ala Thr Lys Lys Leu Lys Met Ile
            740                 745                 750

Val Asp Leu Thr Ser Ala Asn Cys Ser His Gln Val Gln Gln Glu Leu
    755                 760                 765

Ser Ser Thr Phe Ala Arg Leu Cys Arg Thr Val Asp Thr Ala Thr Thr
770                 775                 780

Asp Met Asn Asp Glu Leu Lys Thr Leu Asp Ser Gln Leu Asn Ile Leu
785                 790                 795                 800

Glu Ala Asn Gln Lys Gln Leu Lys Leu Leu Arg Asn Lys Ala Asn Tyr
                805                 810                 815

Ile Gln Asn Glu Leu Asp Ile Phe Glu His Asn Tyr Ile Ser Pro Gln
            820                 825                 830

<210> SEQ ID NO 5
<211> LENGTH: 2226
<212> TYPE: DNA
<213> ORGANISM: Homo sapiens

<400> SEQUENCE: 5
atggcagaac ctgtttctcc actgaagcac tttgtgctgg ctaagaaggg gattactgca     60
```

-continued

```
atctttgacc agttactgga gtttgttact gaaggatcac attttgttga agcaacatat      120
aagaatccgg aacttgatcg aatagccact gaagatgatc tggtagaaat gcaaggatat      180
aaagacaagc tttccatcat tggtgaggtg ctatctcgga gacacatgaa ggtggcattt      240
tttggcagga caagcagtgg gaagagctct gttatcaatg caatgttgtg ggataaagtt      300
ctccctagtg ggattggcca tataaccaat tgcttcctaa gtgttgaagg aactgatgga      360
gataaagcct atcttatgac agaaggatca gatgaaaaaa agagtgtgaa gacagttaat      420
caactggccc atgcccttca catggacaaa gatttgaagg ctggctgtct tgtacgtgtg      480
ttttggccaa aagcaaaatg tgccctcttg agagatgacc tggtgttagt agacagtcca      540
ggcacagatg tcactacaga gctggatagc tggattgata gttttgcct agatgctgat       600
gtctttgttt tggtcgcaaa ctctgaatca acactaatga atacggaaaa acacttttt       660
cacaaggtga atgagtggct ttccaagcct aatattttca ttctcaataa tcgttgggat      720
gcctctgcat cagagccaga atatatgaa gacgtacgca gacagcacat ggaaagatgc       780
ctgcatttct tggtggagga gctcaaagtt gcaaatgctt tagaagcaca gaatcgtatc      840
ttctttgttt cagcaaagga agttcttagt gctagaaagc aaaaagcaca ggggatgcca      900
gaaagtggtg tggcacttgc tgaaggattt catgcaagat tacaggaatt tcagaatttt      960
gaacaaatct tgaggagtg tatctcgcag tcagcagtga aaacaaagtt cgaacagcac       1020
actatcagag ctaaacagat actagctact gtgaaaaaca taatggattc agtaaacctg      1080
gcagctgaag ataaaaggca ttattcagtg gaagagaggg aagaccaaat tgatagactg      1140
gactttattc gaaaccagat gaaccttta acactggatg ttaagaaaaa aatcaaggag       1200
gttaccgagg aggtggcaaa caaagtttca tgtgcaatga cagatgaaat ttgtcgactg      1260
tctgttttgg ttgatgaatt tgttcagag tttcatccta atccagatgt attaaaaata       1320
tataaaagtg aattaaataa gcacatagag gatggtatgg gaagaaattt ggctgatcga      1380
tgcaccgatg aagtaaacgc cttagtgctt cagacccagc aagaaattat cgaaaatttg      1440
aagccattac ttccagctgg tatacaggat aaactacata cactgatccc ttgcaagaaa      1500
tttgatctca gttataatct aaattaccac aagttatgtt cagattttca agaggatatt      1560
gtatttcgtt tttccctggg ctggtcttcc cttgtacatc gattttttggg ccctagaaat      1620
gctcaaaggg tgctcctagg attatcagag cctatctttc agctccctag atctttagct      1680
tctactccca ctgctcctac cactccagca acgccagata tgcatcaca ggaagaactc       1740
atgattacat tagtaacagg attggcgtcc gttacatcta gaacttctat gggcatcatt      1800
attgtcggag gagtgatttg gaaaactata ggctggaaac tcctatctgt ttcattaact      1860
atgtatggag ctttgtatct ttatgaaaga ctgagctgga ccacccatgc caaggagcga      1920
gcctttaaac agcagtttgt aaactatgca actgaaaaac tgaggatgat tgttagctcc      1980
acgagtgcaa actgcagtca ccaagtaaaa caacaaatag ctaccacttt tgcccgcctg      2040
tgccaacaag ttgatattac tcaaaaacag ctggaagaag aaattgctag attacccaaa      2100
gaaatagatc agttggagaa aatacaaaac aattcaaagc tcttaagaaa taagctgtt       2160
caacttgaaa atgagctgga gaattttact aagcagtttc taccttcaag caatgaagaa      2220
tcctaa                                                                 2226
```

<210> SEQ ID NO 6
<211> LENGTH: 741
<212> TYPE: PRT
<213> ORGANISM: Homo sapiens

<400> SEQUENCE: 6

```
Met Ala Glu Pro Val Ser Pro Leu Lys His Phe Val Leu Ala Lys Lys
1               5                   10                  15

Gly Ile Thr Ala Ile Phe Asp Gln Leu Leu Glu Phe Val Thr Glu Gly
            20                  25                  30

Ser His Phe Val Glu Ala Thr Tyr Lys Asn Pro Glu Leu Asp Arg Ile
        35                  40                  45

Ala Thr Glu Asp Asp Leu Val Glu Met Gln Gly Tyr Lys Asp Lys Leu
    50                  55                  60

Ser Ile Ile Gly Glu Val Leu Ser Arg Arg His Met Lys Val Ala Phe
65                  70                  75                  80

Phe Gly Arg Thr Ser Ser Gly Lys Ser Ser Val Ile Asn Ala Met Leu
                85                  90                  95

Trp Asp Lys Val Leu Pro Ser Gly Ile Gly His Ile Thr Asn Cys Phe
            100                 105                 110

Leu Ser Val Glu Gly Thr Asp Gly Asp Lys Ala Tyr Leu Met Thr Glu
        115                 120                 125

Gly Ser Asp Glu Lys Lys Ser Val Lys Thr Val Asn Gln Leu Ala His
    130                 135                 140

Ala Leu His Met Asp Lys Asp Leu Lys Ala Gly Cys Leu Val Arg Val
145                 150                 155                 160

Phe Trp Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ser Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Trp Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His
                245                 250                 255

Met Glu Arg Cys Leu His Phe Leu Val Glu Glu Leu Lys Val Ala Asn
            260                 265                 270

Ala Leu Glu Ala Gln Asn Arg Ile Phe Phe Val Ser Ala Lys Glu Val
        275                 280                 285

Leu Ser Ala Arg Lys Gln Lys Ala Gln Gly Met Pro Glu Ser Gly Val
    290                 295                 300

Ala Leu Ala Glu Gly Phe His Ala Arg Leu Gln Glu Phe Gln Asn Phe
305                 310                 315                 320

Glu Gln Ile Phe Glu Glu Cys Ile Ser Gln Ser Ala Val Lys Thr Lys
                325                 330                 335

Phe Glu Gln His Thr Ile Arg Ala Lys Gln Ile Leu Ala Thr Val Lys
            340                 345                 350

Asn Ile Met Asp Ser Val Asn Leu Ala Ala Glu Asp Lys Arg His Tyr
        355                 360                 365

Ser Val Glu Glu Arg Glu Asp Gln Ile Asp Arg Leu Asp Phe Ile Arg
    370                 375                 380

Asn Gln Met Asn Leu Leu Thr Leu Asp Val Lys Lys Lys Ile Lys Glu
385                 390                 395                 400

Val Thr Glu Glu Val Ala Asn Lys Val Ser Cys Ala Met Thr Asp Glu
```

-continued

```
            405                 410                 415
Ile Cys Arg Leu Ser Val Leu Val Asp Glu Phe Cys Ser Glu Phe His
        420                 425                 430
Pro Asn Pro Asp Val Leu Lys Ile Tyr Lys Ser Glu Leu Asn Lys His
        435                 440                 445
Ile Glu Asp Gly Met Gly Arg Asn Leu Ala Asp Arg Cys Thr Asp Glu
        450                 455                 460
Val Asn Ala Leu Val Leu Gln Thr Gln Gln Glu Ile Ile Glu Asn Leu
465                 470                 475                 480
Lys Pro Leu Leu Pro Ala Gly Ile Gln Asp Lys Leu His Thr Leu Ile
                485                 490                 495
Pro Cys Lys Lys Phe Asp Leu Ser Tyr Asn Leu Asn Tyr His Lys Leu
                500                 505                 510
Cys Ser Asp Phe Gln Glu Asp Ile Val Phe Arg Phe Ser Leu Gly Trp
            515                 520                 525
Ser Ser Leu Val His Arg Phe Leu Gly Pro Arg Asn Ala Gln Arg Val
        530                 535                 540
Leu Leu Gly Leu Ser Glu Pro Ile Phe Gln Leu Pro Arg Ser Leu Ala
545                 550                 555                 560
Ser Thr Pro Thr Ala Pro Thr Thr Pro Ala Thr Pro Asp Asn Ala Ser
                565                 570                 575
Gln Glu Glu Leu Met Ile Thr Leu Val Thr Gly Leu Ala Ser Val Thr
                580                 585                 590
Ser Arg Thr Ser Met Gly Ile Ile Ile Val Gly Val Ile Trp Lys
                595                 600                 605
Thr Ile Gly Trp Lys Leu Leu Ser Val Ser Leu Thr Met Tyr Gly Ala
        610                 615                 620
Leu Tyr Leu Tyr Glu Arg Leu Ser Trp Thr Thr His Ala Lys Glu Arg
625                 630                 635                 640
Ala Phe Lys Gln Gln Phe Val Asn Tyr Ala Thr Glu Lys Leu Arg Met
                645                 650                 655
Ile Val Ser Ser Thr Ser Ala Asn Cys Ser His Gln Val Lys Gln Gln
                660                 665                 670
Ile Ala Thr Thr Phe Ala Arg Leu Cys Gln Gln Val Asp Ile Thr Gln
                675                 680                 685
Lys Gln Leu Glu Glu Glu Ile Ala Arg Leu Pro Lys Glu Ile Asp Gln
        690                 695                 700
Leu Glu Lys Ile Gln Asn Asn Ser Lys Leu Leu Arg Asn Lys Ala Val
705                 710                 715                 720
Gln Leu Glu Asn Glu Leu Glu Asn Phe Thr Lys Gln Phe Leu Pro Ser
                725                 730                 735
Ser Asn Glu Glu Ser
            740
```

<210> SEQ ID NO 7
<211> LENGTH: 3148
<212> TYPE: DNA
<213> ORGANISM: Homo sapiens

<400> SEQUENCE: 7

```
aacttctcgg gaagatgagg cagtttggca tctgtggccg agttgctgtt gccgggtgat      60
agttggagcg gagacttagc ataatggcag aacctgtttc tccactgaag cactttgtgc     120
tggctaagaa ggcgattact gcagtctttg accagttact ggagtttgtt actgaaggat     180
```

```
cacattttgt tgaagcaaca tataagaatc cggaacttga tcgaatagcc actgaagatg    240
atctggtaga aatgcaagga tataaagaca agctttccat cattggtgag gtgctatctc    300
ggagacacat gaaggtggca ttttttggca ggacaagcag tgggaagagc tctgttatca    360
atgcaatgtt gtgggataaa gttctcccta gtgggattgg ccatataacc aattgcttcc    420
taagtgttga aggaactgat ggagataaag cctatcttat gacagaagga tcagatgaaa    480
aaaagagtgt gaagacagtt aatcaactgg cccatgccct tcacatggac aaagatttga    540
aagctggctg tcttgtacgt gtgttttggc caaaagcaaa atgtgccctc ttgagagatg    600
acctggtgtt agtagacagt ccaggcacag atgtcactac agagctggat agctggattg    660
ataagttttg cctagatgct gatgtctttg ttttggtcgc aaactctgaa tcaacactaa    720
tgaatacgga aaaacacttt tttcacaagg tgaatgagcg gctttccaag cctaatattt    780
tcattctcaa taatcgttgg gatgcctctg catcagagcc agaatatatg gaagacgtac    840
gcagacagca catggaaaga tgcctgcatt tcttggtgga ggagctcaaa gttgtaaatg    900
ctttagaagc acagaatcgt atcttctttg tttcagcaaa ggaagttctt agtgctagaa    960
agcaaaaagc acaggggatg ccagaaagtg gtgtggcact tgctgaagga tttcatgcaa   1020
gattacagga atttcagaat tttgaacaaa tctttgagga gtgtatctcg cagtcagcag   1080
tgaaaacaaa gttcgaacag cacactatca gagctaaaca gatactagct actgtgaaaa   1140
acataatgga ttcagtaaac ctggcagctg aagataaaag gtttcatgtg caatgacaga   1200
tgaaatttgt cgactgtctg ttttggttga tgaattttgt tcagagtttc atcctaatcc   1260
agatgtatta aaaatatata aaagtgaatt aaataagcac atagaggatg gtatgggaag   1320
aaatttggct gatcgatgca ccgatgaagt aaacgcctta gtgcttcaga cccagcaaga   1380
aattattgaa aatttgaagc cattacttcc agctggtata caggataaac tacatacact   1440
gatcccttgc aagaaatttg atctcagtta taatctaaat taccacaagt tatgttcaga   1500
ttttcaagag gatattgtat ttcgtttttc cctgggctgg tcttcccttg tacatcgatt   1560
tttgggccct agaaatgctc aaagggtgct cctaggatta tcagagccta tctttcagct   1620
ccctagatct ttagcttcta ctcccactgc tcctaccact ccagcaacgc cagataatgc   1680
atcacaggaa gaactcatga ttacattagt aacaggattg gcgtccgtta catctagaac   1740
ttctatgggc atcattattg ttggaggagt gatttggaaa actataggct ggaaactcct   1800
atctgtttca ttaactatgt atggagcttt gtatctttat gaaagactga gctggaccac   1860
ccatgccaag gagcgagcct ttaaacagca gtttgtaaac tatgcaactg aaaaactgag   1920
gatgattgtt agctccacga gtgcaaactg cagtcaccaa gtaaaacaac aaatagctac   1980
cacttttgct cgcctgtgcc aacaagttga tattactcaa aaacagctgg aagaagaaat   2040
tgctagatta cccaaagaaa tagatcagtt ggagaaaata caaacaattc aaagctctt    2100 aagaaataaa gctgttcaac ttgaaaatga gctggagaat tttactaagc agtttctacc   2160
ttcaagcaat gaagaatcct aacaatagag attgctttgg tgaccatgat aggaggaaac   2220
gaaacttgta agattggaac agttgttatt tttatgaaat tactttaaat atgaattgta   2280
ctaactgtac ctaaatagca aagccctgtg tagattctgg taatgatctg tctcagggta   2340
tgtgtatttt tgaagagtgt tatgtcctta gtttaatttt tgagtaaaga aaaggctaaa   2400
atcatgaatt agttacaagc aacagtacca acttatgtga cccctgaggg gtggggctgt   2460
gagctcttaa tttgtttttg attctgaaaa actctgcttc ctggcatcca ggagttagag   2520
attgagcctt tcatcttctt tctcaaaact agttttttgat gctttctttc atgggaatag   2580
```

```
tcactttttt atttagtaaa tcgcattgct ggaaccacca aggagtgtgg aatgtccttg    2640
agtgtattat ttatgcaagt cacagtcacg ttgccatcat ggcagctatg tgaaacacta    2700
ataaatgtgt ttttactttt tattcccgtt aaaactgatg taaaacagga taaaggcttg    2760
ttatagtcac ttataagtat ctgggtctaa gtaatttcct tagatgtttc taaagaaaca    2820
ttttcagctt tgctcccatt atgattccaa taaggaacgc tttcctagtg caattttagg    2880
agtaaagttt gaagagataa aaatagccaa agataggaga cgtctgaatt ttgaatgata    2940
aacagtgatg ttttaaaaaa gctgttgttc ttcaggaggc atttgcctag gatattgctg    3000
gattataccc cattggaggc ttttaatttt atttgtatga attttccagg atttcattaa    3060
aaattattat tgtattttt accttaatga aagattttgg gttcaaatat ctttctatat     3120
taaaagctga ttgagtctgt acatatgt                                       3148
```

<210> SEQ ID NO 8
<211> LENGTH: 370
<212> TYPE: PRT
<213> ORGANISM: Homo sapiens

<400> SEQUENCE: 8

```
Met Ala Glu Pro Val Ser Pro Leu Lys His Phe Val Leu Ala Lys Lys
 1               5                  10                  15

Ala Ile Thr Ala Val Phe Asp Gln Leu Leu Glu Phe Val Thr Glu Gly
            20                  25                  30

Ser His Phe Val Glu Ala Thr Tyr Lys Asn Pro Glu Leu Asp Arg Ile
        35                  40                  45

Ala Thr Glu Asp Asp Leu Val Glu Met Gln Gly Tyr Lys Asp Lys Leu
    50                  55                  60

Ser Ile Ile Gly Glu Val Leu Ser Arg Arg His Met Lys Val Ala Phe
65                  70                  75                  80

Phe Gly Arg Thr Ser Ser Gly Lys Ser Ser Val Ile Asn Ala Met Leu
                85                  90                  95

Trp Asp Lys Val Leu Pro Ser Gly Ile Gly His Ile Thr Asn Cys Phe
            100                 105                 110

Leu Ser Val Glu Gly Thr Asp Gly Asp Lys Ala Tyr Leu Met Thr Glu
        115                 120                 125

Gly Ser Asp Glu Lys Lys Ser Val Lys Thr Val Asn Gln Leu Ala His
    130                 135                 140

Ala Leu His Met Asp Lys Asp Leu Lys Ala Gly Cys Leu Val Arg Val
145                 150                 155                 160

Phe Trp Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ser Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Arg Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His
                245                 250                 255

Met Glu Arg Cys Leu His Phe Leu Val Glu Glu Leu Lys Val Val Asn
            260                 265                 270
```

-continued

```
Ala Leu Glu Ala Gln Asn Arg Ile Phe Phe Val Ser Ala Lys Glu Val
            275                 280                 285
Leu Ser Ala Arg Lys Gln Lys Ala Gln Gly Met Pro Glu Ser Gly Val
        290                 295                 300
Ala Leu Ala Glu Gly Phe His Ala Arg Leu Gln Glu Phe Gln Asn Phe
305                 310                 315                 320
Glu Gln Ile Phe Glu Cys Ile Ser Gln Ser Ala Val Lys Thr Lys
                325                 330                 335
Phe Glu Gln His Thr Ile Arg Ala Lys Gln Ile Leu Ala Thr Val Lys
            340                 345                 350
Asn Ile Met Asp Ser Val Asn Leu Ala Ala Glu Asp Lys Arg Phe His
        355                 360                 365
Val Gln
    370

<210> SEQ ID NO 9
<211> LENGTH: 4550
<212> TYPE: DNA
<213> ORGANISM: Homo sapiens

<400> SEQUENCE: 9
gtaggcgggg cgagccggct gggctcaggg tccaccagct cacccgggtc gaggggcaat      60
ctgaggcgac tggtgacgcg cttatccact tccctcctcc cgcctccccc cggggtggcg     120
ctcgctggtg acgtagtgag tgtgatggcc gccgcgaggc cgggaaggtg aagtcaggac     180
tggtggagtc aacacagtca atcaatagcc aacctcaacc tgagacagga cagaagagaa     240
ctcagaatct ttttgtcttt tggacttcag ccatgtccat gatgcctacc ctgtgaagat     300
ctctcaccat ccaaaaaacg caatgtccct gctcttctct cgatgcaact ctatcgtcac     360
agtcaagaaa aataagagac acatggctga ggtgaatgca tccccactta agcactttgt     420
cactgccaag aagaagatca atggcatttt tgagcagctg ggggcctaca tccaggagag     480
cgccaccttc cttgaagaca cgtacaggaa tgcagaactg accccgttaa ccacagaaga     540
acaggttctg gacgtcaaag gttacctatc aaagtgagag gcatcagtga ggtgctggc     600
tcggaggcac atgaaagtgg cttttttttgg ccggacgagc aatgggaaga gcaccgtgat     660
caatgccatg ctctgggaca agttctgcc tctgggatt ggccacacca ccaattgctt     720
cctgcgggta gagggcacag atggccatga ggccttttctc cttaccgagg gctcagagga     780
aaagaggagt gccaagactg tgaaccagct ggcccatgcc ctccaccagg acaagcagct     840
ccatgccggc agcctagtga gtgtgatgtg cccaactct aagtgcccac ttctgaagga     900
tgacctcgtt ttgatggaca gccctggtat tgatgtcacc acagagctgg acagctggat     960
tgacaagttt tgtctggatg ctgatgtgtt tgtgctggtg ccaactcag agtccaccct    1020
gatgcagacg gaaaagcact tcttccacaa ggtgagtgag cgtctctccc ggccaaacat    1080
cttcatcctg aacaaccgct gggatgcatc tgcctcagag cccgagtaca tggaggagt    1140
gcggcggcag cacatggagc gttgtaccag cttcctggtg gatgagctgg gcgtggtgga    1200
tcgatcccag gccggggacc gcatcttctt tgtgtctgct aaggaggtgc tcaacgccag    1260
gattcagaaa gcccagggca tgcctgaagg agggggcgct ctcgcagaag ctttcaagt    1320
gaggatgttt gagtttcaga attttgagag agatttgag gagtgcatct cccagtctgc    1380
agtgaagacc aagtttgagc agcacacggt ccggccaag cagattgcag aggcggttcg    1440
actcatcatg gactccctgc acatggcggc tcggagcag caggtttact gcgaggaaat    1500
```

-continued

```
gcgtgaagag cggcaagacc gactgaaatt tattgacaaa cagctggagc tcttggctca   1560
agactataag ctgcgaatta agcagattac ggaggaagtg gagaggcagg tgtcgactgc   1620
aatggccgag gagatcaggc gcctctctgt actggtggac gattaccaga tggacttcca   1680
cccttctcca gtagtcctca aggtttataa gaatgagctg caccgccaca tagaggaagg   1740
actgggtcga acatgtctg accgctgctc cacggccatc accaactccc tgcagaccat   1800
gcagcaggac atgatagatg gcttgaaacc cctccttcct gtgtctgtgc ggagtcagat   1860
agacatgctg gtcccacgcc agtgcttctc cctcaactat gacctaaaact gtgacaagct   1920 gtgtgctgac ttccaggaag acattgagtt ccatttctct ctcggatgga ccatgctggt   1980
gaataggttc ctgggcccca agaacagccg tcgggcttg atgggctaca atgaccaggt   2040
ccagcgtccc atccctctga cgccagccaa ccccagcatg ccccactgc cacagggctc   2100 gctcacccag gaggagttca tggttttcat ggttaccggc ctggcctcct tgacatccag   2160
gacctccatg ggcattcttg ttgttggagg agtggtgtgg aaggcagtgg gctggcggct   2220
cattgccctc tcctttgggc tctatggcct cctctacgtc tatgagcgtc tgacctggac   2280
caccaaggcc aaggagaggg ccttcaagcg ccagtttgtg gagcatgcca gcgagaagct   2340
gcagcttgtc atcagctaca ctggctccaa ctgcagccac caagtccagc aggaactgtc   2400
tgggaccttt gctcatctgt gtcagcaagt tgacgtcacc cggagaaacc tggagcagga   2460
aattgccgcc atgaacaaga aaattgaggt tcttgactca cttcagagca aagcaaagct   2520
gctcaggaat aaagccggtt ggttggacag tgagctcaac atgttcacac accagtacct   2580
gcagcccagc agatagtggg cacctgaggc ggagtctgcg tggagagggg cggtgctgcc   2640
agccctaagt gccgtgtggg ctcccccagg ggcacgtgtg gctcctgccc cctggccact   2700
gccaagagaa tgaagcaccc agtctcgtac cattttgagc cctccagcac tacttatttt   2760
cccccacctt tgcctgctgt tgctggaaga gctggctcat accccaaag gacactttca   2820 gcgacagcta tggacagcat ggtaccaagg agttaagttg aggctttttc cagctttctc   2880
tggttcattt gattgcttga taaggcctca ggatctcagc attgcacaat gcctcatgga   2940
agcctttgag ggtatcacac agacacccc accttcctcc agcctgtgcg cacctgccct   3000
ccttgcagcc cagcacacct gcaggtgtaa gggacgattg gagtttcttc ccagagagtc   3060
tgtcccagaa ggactgtggc ttgtgtgtgt ccatctcgcc tgttggctca gtgcttcatc   3120
ccatttgcag agcctcagac acgtcttggt ggtgaggctc agttacccct gggcttaggc   3180
tgaggcgggc cctgtgctgg gggtggtaga aaggatgctg ctgaggcagc tggaggagtg   3240
ggagtagctc agaggggagg gctgttggat gtatggggag ctggcagagc aggtggcagt   3300
cactgggaca aggagggact tgcctctctt ctcattattg tgtcctttgc tttagtgtca   3360
gtcctggact tgtgcaggcc tgttttgtgt agatctgttt tggaagatgg catggtctag   3420
gtggttgaag gatgtagtag aaggatggat ggtggaaggt ggggacgttg gtggctggct   3480
gaggtgcatg ggccccacac aggacagctg gagaatgggc cgtccacttg gcctcgttct   3540 gcgagggct catgggtctg agagccccca cccactaggc ttgattgcat ccctgttgtg   3600 cccctttaaga gacatgtttc cacccccacc ccaaccttgt cccaagtgcc ctggactaaa   3660
tttcctgtgc cagtgactgc agttggccaa gggacaatgt ggaaaaccca gtgtccatct   3720 ttccacccte cctgatctcc agaaccttcg actgaccccc ttgtctttat gctgatgttg   3780
agttttggga ttgttactgg ttgaagtggg ggcagatgcc tgtcaccaag gtgttgactg   3840
```

-continued

```
tgtgagaaaa gcagtttggg tgacaaatcc tgtgtggcac aagttggatc gcttcctaga    3900
aataagcaac acctctccca aaaaagcagc ccacaaggca ggggcccagc agcccagcca    3960
tcactcatct ttgaggaaat gagttggtag cctctgtgca ctgtttggtg gccacatcac    4020
aggtgatgtc ctgttcacat acctgcttgt atttaaagcc ctcagtctgt cctgttgtgt    4080
ggggcgaagt gatggactct gccaggtgga catgctgtgg gtggatgttc ccggcgtgtg    4140
ccgggcctga atggacaggg gccacttcac agcatgtcag ggaaaatcac tgtcacacaa    4200
ttccaatgga ttttgtgctc tttttgaaaa aaaaaaattc tttagcgtaa acatgaattt    4260
tttttcaatg tagcccctgg ggaatgaatg aaattttgag cttcttcaat acgtaaaatt    4320
aaatttatac cactgaggga gagacccttt ctgaaagaag tatggccaaa agcactttaa    4380
tgctgctgac attgttgttt ttatgttcat ttgctggagc gcaagacgtg ctgacacagt    4440 gagtttctc tgatgtattt aaggtgatgt atttgcttga gttactcctg tatcattgct    4500
cataatattg gaaactaaaa taaaacctag ttggaaatcc aaaaaaaaac             4550
```

<210> SEQ ID NO 10
<211> LENGTH: 757
<212> TYPE: PRT
<213> ORGANISM: Homo sapiens

<400> SEQUENCE: 10

```
Met Ser Leu Leu Phe Ser Arg Cys Asn Ser Ile Val Thr Val Lys Lys
 1               5                  10                  15

Asn Lys Arg His Met Ala Glu Val Asn Ala Ser Pro Leu Lys His Phe
            20                  25                  30

Val Thr Ala Lys Lys Lys Ile Asn Gly Ile Phe Glu Gln Leu Gly Ala
        35                  40                  45

Tyr Ile Gln Glu Ser Ala Thr Phe Leu Glu Asp Thr Tyr Arg Asn Ala
    50                  55                  60

Glu Leu Asp Pro Val Thr Glu Glu Gln Val Leu Asp Val Lys Gly
65                  70                  75                  80

Tyr Leu Ser Lys Val Arg Gly Ile Ser Glu Val Leu Ala Arg Arg His
                85                  90                  95

Met Lys Val Ala Phe Phe Gly Arg Thr Ser Asn Gly Lys Ser Thr Val
            100                 105                 110

Ile Asn Ala Met Leu Trp Asp Lys Val Leu Pro Ser Gly Ile Gly His
        115                 120                 125

Thr Thr Asn Cys Phe Leu Arg Val Glu Gly Thr Asp Gly His Glu Ala
    130                 135                 140

Phe Leu Leu Thr Glu Gly Ser Glu Glu Lys Arg Ser Ala Lys Thr Val
145                 150                 155                 160

Asn Gln Leu Ala His Ala Leu His Gln Asp Lys Gln Leu His Ala Gly
                165                 170                 175

Ser Leu Val Ser Val Met Trp Pro Asn Ser Lys Cys Pro Leu Leu Lys
            180                 185                 190

Asp Asp Leu Val Leu Met Asp Ser Pro Gly Ile Asp Val Thr Thr Glu
        195                 200                 205

Leu Asp Ser Trp Ile Asp Lys Phe Cys Leu Asp Ala Asp Val Phe Val
    210                 215                 220

Leu Val Ala Asn Ser Glu Ser Thr Leu Met Gln Thr Glu Lys His Phe
225                 230                 235                 240

Phe His Lys Val Ser Glu Arg Leu Ser Arg Pro Asn Ile Phe Ile Leu
                245                 250                 255
```

```
Asn Asn Arg Trp Asp Ala Ser Ala Ser Glu Pro Glu Tyr Met Glu Glu
            260                 265                 270

Val Arg Arg Gln His Met Glu Arg Cys Thr Ser Phe Leu Val Asp Glu
        275                 280                 285

Leu Gly Val Val Asp Arg Ser Gln Ala Gly Asp Arg Ile Phe Phe Val
    290                 295                 300

Ser Ala Lys Glu Val Leu Asn Ala Arg Ile Gln Lys Ala Gln Gly Met
305                 310                 315                 320

Pro Glu Gly Gly Gly Ala Leu Ala Glu Gly Phe Gln Val Arg Met Phe
                325                 330                 335

Glu Phe Gln Asn Phe Glu Arg Arg Phe Glu Glu Cys Ile Ser Gln Ser
            340                 345                 350

Ala Val Lys Thr Lys Phe Glu Gln His Thr Val Arg Ala Lys Gln Ile
        355                 360                 365

Ala Glu Ala Val Arg Leu Ile Met Asp Ser Leu His Met Ala Ala Arg
    370                 375                 380

Glu Gln Gln Val Tyr Cys Glu Glu Met Arg Glu Glu Arg Gln Asp Arg
385                 390                 395                 400

Leu Lys Phe Ile Asp Lys Gln Leu Glu Leu Leu Ala Gln Asp Tyr Lys
                405                 410                 415

Leu Arg Ile Lys Gln Ile Thr Glu Glu Val Arg Gln Val Ser Thr
            420                 425                 430

Ala Met Ala Glu Glu Ile Arg Arg Leu Ser Val Leu Val Asp Asp Tyr
        435                 440                 445

Gln Met Asp Phe His Pro Ser Pro Val Val Leu Lys Val Tyr Lys Asn
    450                 455                 460

Glu Leu His Arg His Ile Glu Glu Gly Leu Gly Arg Asn Met Ser Asp
465                 470                 475                 480

Arg Cys Ser Thr Ala Ile Thr Asn Ser Leu Gln Thr Met Gln Gln Asp
                485                 490                 495

Met Ile Asp Gly Leu Lys Pro Leu Leu Pro Val Ser Val Arg Ser Gln
            500                 505                 510

Ile Asp Met Leu Val Pro Arg Gln Cys Phe Ser Leu Asn Tyr Asp Leu
        515                 520                 525

Asn Cys Asp Lys Leu Cys Ala Asp Phe Gln Glu Asp Ile Glu Phe His
    530                 535                 540

Phe Ser Leu Gly Trp Thr Met Leu Val Asn Arg Phe Leu Gly Pro Lys
545                 550                 555                 560

Asn Ser Arg Arg Ala Leu Met Gly Tyr Asn Asp Gln Val Gln Arg Pro
                565                 570                 575

Ile Pro Leu Thr Pro Ala Asn Pro Ser Met Pro Pro Leu Pro Gln Gly
            580                 585                 590

Ser Leu Thr Gln Glu Glu Phe Met Val Ser Met Val Thr Gly Leu Ala
        595                 600                 605

Ser Leu Thr Ser Arg Thr Ser Met Gly Ile Leu Val Val Gly Gly Val
    610                 615                 620

Val Trp Lys Ala Val Gly Trp Arg Leu Ile Ala Leu Ser Phe Gly Leu
625                 630                 635                 640

Tyr Gly Leu Leu Tyr Val Tyr Glu Arg Leu Thr Trp Thr Thr Lys Ala
                645                 650                 655

Lys Glu Arg Ala Phe Lys Arg Gln Phe Val Glu His Ala Ser Glu Lys
            660                 665                 670
```

```
Leu Gln Leu Val Ile Ser Tyr Thr Gly Ser Asn Cys Ser His Gln Val
        675                 680                 685

Gln Gln Glu Leu Ser Gly Thr Phe Ala His Leu Cys Gln Gln Val Asp
    690                 695                 700

Val Thr Arg Glu Asn Leu Glu Gln Glu Ile Ala Ala Met Asn Lys Lys
705                 710                 715                 720

Ile Glu Val Leu Asp Ser Leu Gln Ser Lys Ala Lys Leu Leu Arg Asn
                725                 730                 735

Lys Ala Gly Trp Leu Asp Ser Glu Leu Asn Met Phe Thr His Gln Tyr
            740                 745                 750

Leu Gln Pro Ser Arg
        755

<210> SEQ ID NO 11
<211> LENGTH: 1812
<212> TYPE: DNA
<213> ORGANISM: Homo sapiens

<400> SEQUENCE: 11
agcagtggga agagctctgt taacaatgca atgttgtggg ataaagttct cactagtggg      60
attggccata taccaactg cttcctaagt gttgaaggaa ccgatggaga taaatcctat     120
cttatgacag aaggatcaga tgaaaaaaga gtgtaaagac aattaatcaa ctggcccatg     180
cccttcacat ggacaaaaac ttgaaagctg gctgtcttgt acatgtgttt tggccaaaag     240
caaaatgtgc cctcttgaga gattacctgg tgttagtaga cagtccaggc acagatgtta     300
ctacagagct ggatagctgg attgataagt tttgcctaga tgctgatgtc tttgttttgg     360
ttgcaaactc tgaatcaaca ctaacgaata cggaaaaaca tgttttcaca acatgaatga     420
gtggctttcc aagcctaata ttttcattct caataatcgt tgggatgcct ctgcatcaga     480
gccagaatat atggaagatg tgggccacct gctgaaggat ttcaggcaag attacaggaa     540
tttcagaatt ttgaacaaat ctttgaggag tgtatctcac agtcagcagt gaaaacaaag     600
tttgaacagc acactatcag agctaaacag atactagcta ctgtgaaaaa caatggatt     660
caataaacat ggcagctgaa cagaaaaggc attatgcagt ggaagagaag gaagaccaaa     720
ttgatagact ggactttatc tgaaaccaga tgaacctttt aacactggat gttaacaaaa     780
aaaccaggga ggttactggg gaggtggcaa acaaagtgtc atgtgcaatg acagatgaaa     840
tttgtcaact gtctgttttg gttgatgaat tttgttcagt ttcatcctac tccagatgta     900
ttaaaaatat ataaaagtga attaaataag catatagagg atggtatggg aagaaatttg     960
gctgattgat gcaccaatga agtaaacacc ttagtgcttc agttccagca agaaattgtt    1020
gaaaatttga agccattact tccagctggt atataggata aactacatac actgatccct    1080
tgcaagaaat ttgatcttag ttataatcta aattaccaca agttatgttc agattttcaa    1140
gaagatattg tgtttcattt ttccctgggc tggtcttccc tcgtacctca atttttgggc    1200
cctagaaatg ctcaaatggt gctcctagga ttatcagagc ctatctttca gctccctaga    1260
tctttagctt ctactcccac tgctcctacc agtccagcaa tgccagataa tgcatcacag    1320
gcagaactca tgattacatt agtaacagga ttggcttctc ttacatctag aacttctatg    1380
ggcatcgata atgttggagg aatgatttgg aaaactatag cgtggaaact catatctgtt    1440
tcattaacta tgtatggagc tttgtatctt tatgaaagac tgtcctggac cacccatgcc    1500
aaggagagag cctttaaaca gcagtttgta aactatgcaa ctggaaaact gaagatgatt    1560
gctagctcca caagtgcaaa ctgcagccac caagtaaaac aacaaatggc taccactttt    1620
```

```
gctcgcctgt gccaacaagc tgatattact caaagacaac tggaagaaga aattgctaga    1680
ttacccaaag aaatagatca gtgggagaaa atacaaaaca atttaaagct cttaagaaat    1740
aaagctgttc aacttgaata tgagctggag aattttacta agcagtttct accttcacgc    1800
gatgaagaat cc                                                       1812

<210> SEQ ID NO 12
<211> LENGTH: 2465
<212> TYPE: DNA
<213> ORGANISM: Homo sapiens

<400> SEQUENCE: 12
ctccactgaa acactttgtg ctggataaga aggcaattac tgaaatcttt gaccagttac      60
tggagtttgt tactgaggat cacatattgt tgaagtatgt gaatctccct tctcagctca     120
agatctgaag atccaatcag gtggaataaa aatagcaac atataagaat ctagaacttg      180
actgagctac tgaggataat caagtagaaa tgtaagaata taaaaacaag ctttctatca     240
ttggtaaggt gctatctcgg agacaaatga aggtggcatt ttttggcagg acaagctctg     300
ttatcaatgc aatgttgtgg gataaagctc tccttagtgg gattgatcat acaaccaatt     360
gcttccaaag tgtttaagag accaatggag ataaaaccta tcttatgaca aaaggataag     420
atgaaaaaac agtgtaaaca cagttcatca gctgtcctat gcccttcatg tggacaaagg     480
cttggaagct ggctgtctta tacatgtgtt ttggccaaag acaaagtgtg tcctcttgaa     540
aggtgagctg gttttagtag acagtccagg cacagatgtc actacagagc tggatacctg     600
gattgatgag tgttgcttag atgcttatgt catcattttg tttgtaaact ctgaatcaac     660
actaatgaac acagaaaaac attttttttca caaggtaaat gagcagcttt ccaagcctaa     720
taatttaatt ctgaataatc actgggatgt cgcttcatca gagccagaat atatggaaga     780
tgtatgtaga cagcacatgg aaagatgctt gcatttcttt gtggaggagg ttaaagttgt     840
ggatccttta gaagcacaga atcatatatt cttcatttca gcaaaggaag ttcttagtgc     900
tagacagcac aaaccacagg ggatgccaga agcagtgaa gtacttggta aacgatttca     960
ggcaagatta caggagtttc agaattttaa caaatcttta aggagtgtat ctcacaatca    1020
gcagtgaaaa cagggttgaa acagcacact atcggagcta agccaatact agatattgtg    1080
aaaaacacaa tggattcaat aaacgtggca gcaacagaga gagtttatt caaagaaaga    1140 gcgggaagaa caaatcgaca gactgagctt tatcccaaac cagatgaacc ttttaacact    1200
agatgttaag aaaaaaatca ggaaggccgg gcgcagtggc tcacgcctgt aatcccagca    1260
ctttgggagg ctgaggcagg tggatcacga ggtcaggagt tcaagaccag cctggccaac    1320
atggtgaaac cccgtctcta ctaaaaagac aaaaattact ctggcgtggt ggcgggtgcc    1380
tgtaatccca gctacttggg aggctgaggc aggtaattgc ttgaacctgg aagggaagg    1440 ttgcagtgag ccaagatcgc accactgcac tccagcctgg gcaacagagt gagactccat    1500
ctcaagaaaa ataaaaaata aaaaataaaa aaatcaggga ggttaccaag gaagtggcaa    1560
acaaggtttc acgtgcaaag acagatgaaa tttgttgact gtctgttttg gttgatgaat    1620
tttattcagt ttcatcctac tccacgtgta ttgaaagtat gtaaaggtga cttaaattag    1680
cacttagaag acgtatcag aagaaatatg gctgattgat gcaccaatta agacaatgcc    1740
tcaatgttta atccaagcaa gaattatta aaaatttgaa accattactt tcagctatat    1800
atagaataaa ctgcatacac taatcccttg caagaaattt gatctcagtc atgacctata    1860
```

| | | | | |
|---|---|---|---|---|
| ttgccacaag | ttatgaccag | attttcaaga | gggtattgta | ttccattttt ccctgggctg | 1920 |
| gtcttcactt | gtgcattgat | tcctgggccc | tacaaatgct | cagagggtgc tcctaggatt | 1980 |
| gtcagagcct | aactttccct | agctctttag | cctgtactcc | cactgcttct atcaacccag | 2040 |
| caacaccaga | taatgcatca | cacaaagaac | tcatggttac | cttaataaca ggattagctt | 2100 |
| ctcttacatc | taggacttct | acggacatca | ctgttggagg | agtaatttgg aaaactatag | 2160 |
| gctggcaatt | cgtatatgtt | tcattatgta | tgtatggagt | ttggtatctt tatggaaggc | 2220 |
| tgtcctggac | cacttgtgcc | aaggaaagag | gctttaaaca | acagtttgtg aactatgctt | 2280 |
| ctgaaaaact | tcagataatt | gctagcttca | ggaatgcaaa | ctgcagccat gaagtacaac | 2340 |
| aagaaatggc | tatcactttc | gcttgccagt | gccaacaagt | tgttactaaa agacatctgg | 2400 |
| aagaaattac | tagattatcc | aaagaaatag | atcagttaga | gaacatacaa aacaattcaa | 2460 |
| aactc | | | | | 2465 |

210> SEQ ID NO 13
<211> LENGTH: 2220
<212> TYPE: DNA
<213> ORGANISM: M. musculus
<220> FEATURE:
<221> NAME/KEY: misc_feature
<222> LOCATION: (1)...(2220)
<223> OTHER INFORMATION: n = A,T,C or G

<400> SEQUENCE: 13

| | | | | | |
|---|---|---|---|---|---|
| atggcagaaa | cggtatctcc | actgaagcac | tttgtgctgg | caaagaaagc catcactgca | 60 |
| atcttcggcc | agttactgga | gtttgttact | gagggctcac | attttgttga agcaacatac | 120 |
| aggaatccag | aacttgatcg | aatagcatcc | gaggatgatc | tggtggaaat acagggctac | 180 |
| agaaacaagc | ttgctgtcat | tggggaggtg | ctgtctcgga | gacatatgaa ggtggcattt | 240 |
| tttggcagga | caagtagtgg | caagagctct | gtcatcaatg | caatgctgtg ggataaagtc | 300 |
| ctccccagcg | ggattggtca | cacaaccaac | tgcttcctga | gtgtcgaggg gaccgatgga | 360 |
| gataaagcct | accttatgac | cgaagggtca | gatgaaaaga | aaagtgtgaa gactgttaat | 420 |
| cagctggccc | atgccctcca | tatggataaa | gacttgaaag | ctggctgtct tgtgcatgta | 480 |
| ttttggccca | aagcaaaatg | tgccctcttg | agagatgacc | tgnttttagt agacagccca | 540 |
| ggtacagatg | tcaccacaga | gctggatatc | tgtattgata | agttttgcct tgatgctgat | 600 |
| gtctntgtta | ttgttgcaaa | ctcngaatca | acactgatga | acacngagaa acatgtgttg | 660 |
| cattatgtga | atgagcggct | ctccaagctc | aacatcttca | ttctgaataa ccgttgggat | 720 |
| gcttctgctt | cggagccgga | gtacatggag | gatgtgcgca | gacagcacat ggagagatgt | 780 |
| cttcacttct | tggtagaaga | gctcaaggtt | gtaagtccgt | cggaagctcg gaatcggatc | 840 |
| ttttttgttt | cagccaagga | agttctcaac | tccagaaagc | ataaagctca ggggatgcca | 900 |
| gaaggtggtg | gggcacttgc | agaaggattt | caagcaagat | tacaggagtt tcaaaattttt | 960 |
| gaacaaactt | ttgaggagtg | tatctcgcag | tcagcagtga | aaacaaagtt tgaacagcac | 1020 |
| actatcagag | ctannnnnnn | nnnnnnnnnn | nnnnnnnnnn | nnnnnnnnnn nnnnnnnnnn | 1080 |
| nnnnnnnnnn | nnnnnnnnnn | nnnnnnnnnn | nnnnnnnnnn | nnnnnnnnnn nnnnnnnnnn | 1140 |
| nnnnnnnnnn | nnnnnnnnnn | nnnnnnnnnn | nnnnnnnnnn | nnnnnnnnnn nnnnnnnnnn | 1200 |
| nnnnnnnnnn | nnnnnnnnnn | nnnnnnnnnn | nnnnnnnnnn | nnnnnnnnnn cttatctgtt | 1260 |
| ttggttgatg | agttttgttc | tgagtttcat | cctaccccca | gtgtactgaa agtgtataag | 1320 |
| agtgagttaa | acaagcacat | agaagatggc | atgggaagaa | atttggctga tcggtgtacc | 1380 |

-continued

```
aatgaagtca atgcctccat tcttcaatct cagcaagaaa tcatcgaaaa cttgaagcca    1440
ctacttccag ctggtataca gaataaactt catacattaa tcccttgcaa aaagtttgac    1500
ctcagctatg atctcaattg ccacaagctg tgttcggatt ttcaagagga cattgtgttt    1560
cggttttccc tgggctggtc ttcccttgta catcgattcc tgggttccac aaatgcacag    1620
agggtgctgc tcgggctgtc ggagcccatc tttcaggtcc ctagatcttt agcttcaact    1680
cctactgctc cttctaaccc agcagccccg gataatgcag cccaggagga gctcatgatc    1740
accctgatca caggattggc gtccctcacg tcgagaacct ccatgggcat catcgttgtt    1800
gggggcgtga tttggaaaac agtgggctgg aaactaatct ctgtcacctt aagtatgtac    1860
ggagctctgt acctttatga gaggctgacg tggacgaccc gtgcgaaaga gagagcgttt    1920
aagcagcagt ttgtaaaacta tgcaaccgag aagctgcaga tgattgtgag cttcaccagt    1980
```

```
Glu Ser Thr Leu Met Asn Thr Glu Lys His Val Leu His Tyr Val Asn
    210                 215                 220
Glu Arg Leu Ser Lys Leu Asn Ile Phe Ile Leu Asn Asn Arg Trp Asp
225                 230                 235                 240
Ala Ser Ala Ser Glu Pro Glu Tyr Met Glu Asp Val Arg Arg Gln His
            245                 250                 255
Met Glu Arg Cys Leu His Phe Leu Val Glu Glu Leu Lys Val Val Ser
            260                 265                 270
Pro Ser Glu Ala Arg Asn Arg Ile Phe Phe Val Ser Ala Lys Glu Val
            275                 280                 285
Leu Asn Ser Arg Lys His Lys Ala Gln Gly Met Pro Glu Gly Gly Gly
    290                 295                 300
Ala Leu Ala Glu Gly Phe Gln Ala Arg Leu Gln Glu Phe Gln Asn Phe
305                 310                 315                 320
Glu Gln Thr Phe Glu Glu Cys Ile Ser Gln Ser Ala Val Lys Thr Lys
            325                 330                 335
Phe Glu Gln His Thr Ile Arg Ala Xaa Xaa Xaa Xaa Xaa Xaa Xaa
            340                 345                 350
Xaa Xaa Xaa Xaa Xaa Xaa Xaa Xaa Xaa Xaa Xaa Xaa Xaa Xaa Xaa
    355                 360                 365
Xaa Xaa Xaa Xaa Xaa Xaa Xaa Xaa Xaa Xaa Xaa Xaa Xaa Xaa Xaa
    370                 375                 380
Xaa Xaa Xaa Xaa Xaa Xaa Xaa Xaa Xaa Xaa Xaa Xaa Xaa Xaa Xaa Xaa
385                 390                 395                 400
Xaa Xaa Xaa Xaa Xaa Xaa Xaa Xaa Xaa Xaa Xaa Xaa Xaa Xaa Xaa
            405                 410                 415
Xaa Xaa Leu Ser Val Leu Val Asp Glu Phe Cys Ser Glu Phe His Pro
            420                 425                 430
Thr Pro Ser Val Leu Lys Val Tyr Lys Ser Glu Leu Asn Lys His Ile
            435                 440                 445
Glu Asp Gly Met Gly Arg Asn Leu Ala Asp Arg Cys Thr Asn Glu Val
    450                 455                 460
Asn Ala Ser Ile Leu Gln Ser Gln Gln Glu Ile Ile Glu Asn Leu Lys
465                 470                 475                 480
Pro Leu Leu Pro Ala Gly Ile Gln Asn Lys Leu His Thr Leu Ile Pro
            485                 490                 495
Cys Lys Lys Phe Asp Leu Ser Tyr Asp Leu Asn Cys His Lys Leu Cys
            500                 505                 510
Ser Asp Phe Gln Glu Asp Ile Val Phe Arg Phe Ser Leu Gly Trp Ser
            515                 520                 525
Ser Leu Val His Arg Phe Leu Gly Ser Thr Asn Ala Gln Arg Val Leu
    530                 535                 540
Leu Gly Leu Ser Glu Pro Ile Phe Gln Val Pro Arg Ser Leu Ala Ser
545                 550                 555                 560
Thr Pro Thr Ala Pro Ser Asn Pro Ala Ala Pro Asp Asn Ala Ala Gln
            565                 570                 575
Glu Glu Leu Met Ile Thr Leu Ile Thr Gly Leu Ala Ser Leu Thr Ser
            580                 585                 590
Arg Thr Ser Met Gly Ile Ile Val Val Gly Gly Val Ile Trp Lys Thr
            595                 600                 605
Val Gly Trp Lys Leu Ile Ser Val Thr Leu Ser Met Tyr Gly Ala Leu
    610                 615                 620
```

```
Tyr Leu Tyr Glu Arg Leu Thr Trp Thr Thr Arg Ala Lys Glu Arg Ala
625                 630                 635                 640

Phe Lys Gln Gln Phe Val Asn Tyr Ala Thr Glu Lys Leu Gln Met Ile
            645                 650                 655

Val Ser Phe Thr Ser Ala Asn Cys Ser His Gln Val Gln Gln Glu Met
            660                 665                 670

Ala Thr Thr Phe Ala Arg Leu Cys Gln Gln Val Asp Val Thr Gln Lys
        675                 680                 685

His Leu Glu Glu Glu Ile Ala Arg Leu Ser Lys Glu Ile Asp Gln Leu
    690                 695                 700

Glu Lys Ile Gln Asn Asn Ser Lys Leu Leu Arg Asn Lys Ala Val Gln
705                 710                 715                 720

Leu Glu Ser Glu Leu Glu Asn Phe Ser Lys Gln Phe Leu His Pro Ser
                725                 730                 735

Ser Gly Glu Ser
            740

<210> SEQ ID NO 15
<211> LENGTH: 2744
<212> TYPE: DNA
<213> ORGANISM: M. musculus
<220> FEATURE:
<221> NAME/KEY: misc_feature
<222> LOCATION: (1)...(2744)
<223> OTHER INFORMATION: n = A,T,C or G

<400> SEQUENCE: 15
atgtccctgc tcttttctcg atgcaactcc atcgtcaccg tcaagaagga taagcgacac      60
atggctgaag tgaatgcttc ccctctcaag cactttgtca ctgccaagaa aaagatcaat     120
ggaatctttg agcagctggg ggcctacatc aagagagcg ccagcttcct tgaagacacc      180
cacaggaaca cagaactgga ccccgttacc acggaagacc aggtcctgga cgtcaaaggg     240
tacctgtcca aggtcagggg tatcagcgaa gtgctggcca ggcggcacat gaaggtggct     300
ttttttggcc ggacgagcaa tgggaagagc accgngatca atgccatgct ctgggacaaa     360
gntctgccat ctgggattgg tcataccacc aattgcttnc tgcgggttgg gggcacagat     420
ggccatgagg ccttcctcct cacagagggc tcanaaaaga aaaaagtgt caagactgtg      480 aaccaactgg nccntgccct ccatnaggac gagcagttgc atgcangcag catggggagt     540
gtgatgtggc ccnactccna ntgtncgctc ctgaaggatg acctcntgct gatgacanc      600 cctgggatcg atgttaccac ggagctggac acctggattg anaaatttg cctggatgct      660 gatgtgtttg tgctggnggg ccaactcaan agtccacgct gatgcnaacc nanaaacaac     720
ttntttcaca aaagngagng gaacggtttt tnccggccca acatcttat tcngaataac      780 cgctgggatg cntntgcctn gggcctgagt acatggagga ggtgcggcg cagcacatgg      840 agcgctgcac cagcttttctg gtggatgagc tgggcgtggt ggatcgagct caggctgggg     900
accggatctt cttcgtgtct gccaaggagg ttctcagcgc cagggtccag aaagcccagg     960
gcatgccaga aggtctgggc cggaacctgt ctgaccgctg ctccactgcc attgccagtt    1020
cactgcagac tatgcagcag gacatgatag acggcttgaa gccccttctt cctgtatcta    1080
tgcggaatca gatagacatg ctggtccctc gacagtgttt ctccctcagc tatgacctga    1140
attgtgacaa gctgtgtgct gactttcagg aggacatcga gttccacttc tcccttggat    1200
ggactatgct agtgaacagg ttcctggggc ccaagaatag ccgccgggcc ttgctaggct    1260
acagtgatca ggttcagcgt cctctcccctc tgacacctgc caaccccagc atgcccccct    1320
```

-continued

```
tgncacagag cttcctcacc caggaggagc tcatggtctc catggttact ggcctggnct    1380
ctttgacgtc taggacctcc atgggcattc ttgtggtcgg angantggtg tggaaagcat    1440
nggctggaga cncatcnccc tctcctttgg actgtatggg ctcctggtac ggctatgagc    1500
cactgacctn gaccaccaaa cccaagaaa agggcctta agcgccngtt tgtggaaaac     1560
cccnngagaa cctacagctt atnatcagta caccgnnttt aattgnngcc accaagtcca    1620
caggaantgt ntgggganatt tgtcattttg tgccncaagt gacntccccn aanatntggn    1680
cagaaatntt gcntgaanaa aanaangggt ntgatttctt ttancaancc aactgtnaga    1740
anaanctggt tgtgganggg acttatattt aacncannnt tnccacaaa angtncacag     1800 ggcgncttta aaaaaanagg gcncctccaa tcttttttttt tcctggaccc caaagccaaa    1860
gagagggcct tcaagcgcca gtttgtggaa tacgccagtg agaagctaca gctcatcatc    1920
ngttacaccg gntctaactg cagccaccaa gtccagcagg aattgtctgg gacatttgct    1980
catctgtgcc agcaagttga catcacccga gataatctgg agcaggaaat tgctgccatg    2040
aacaagaaag tcgaggctct ggattcactt cagagcagag ccnaactgct caggaataaa    2100
gctggctggt tggacagcga actcaacatg ttcacacacc agtacctgca gcccagcaga    2160
tagtgggcag ccaggcgga cctgcacgaa naaaangcag ggncgcacct nccatcagct    2220
ctagtccttn gccgctgcag anagaangaa ancacccact cttgtaccaa gntactccct    2280
accccctgca ggaagacccc tggntcatac cctaatggag accaacaagg actgggcagc    2340
tnggnttcaa agaggtatgc atgtgnctgn gnctggntcc tcaccctcac cccgggtgga    2400
aaanactgtg catttgatna anaantttct caaaanngg cctgcaaag actgatgggn     2460 gcctttcagg cattaaggag ncctccttnt tttttcanct gggncacctt caaaaaaaaa    2520 antttgggg acaagatgcc cccaaaaann nggaaactttt tnaaaggcnt gttgtntaaa    2580
anttgttntt gngttgggcn cacnttanac tttttccctn ncnaanctttt aatggnntgg    2640 ggccngccan naccgggggt ttattnacnc tttnttggag gtgggacccc cccccacca    2700 cnanggttgg naaggtgtga acangntttt ttgngntncn nncc                    2744
```

<210> SEQ ID NO 16
<211> LENGTH: 758
<212> TYPE: PRT
<213> ORGANISM: M. musculus
<220> FEATURE:
<221> NAME/KEY: VARIANT
<222> LOCATION: (1)...(758)
<223> OTHER INFORMATION: Xaa = Any Amino Acid

<400> SEQUENCE: 16

```
Met Ser Leu Leu Phe Ser Arg Cys Asn Ser Ile Val Thr Val Lys Lys
1               5                   10                  15

Asp Lys Arg His Met Ala Glu Val Asn Ala Ser Pro Leu Lys His Phe
            20                  25                  30

Val Thr Ala Lys Lys Lys Ile Asn Gly Ile Phe Glu Gln Leu Gly Ala
        35                  40                  45

Tyr Ile Gln Glu Ser Ala Ser Phe Leu Glu Asp Thr His Arg Asn Thr
    50                  55                  60

Glu Leu Asp Pro Val Thr Thr Glu Asp Gln Leu Asp Val Lys Gly
65                  70                  75                  80

Tyr Leu Ser Lys Val Arg Gly Ile Ser Glu Val Leu Ala Arg Arg His
                85                  90                  95
```

```
Met Lys Val Ala Phe Phe Gly Arg Thr Ser Asn Gly Lys Ser Thr Xaa
            100                 105                 110
Ile Asn Ala Met Leu Trp Asp Lys Xaa Leu Pro Ser Gly Ile Gly His
        115                 120                 125
Thr Thr Asn Cys Xaa Leu Arg Val Gly Gly Thr Asp Gly His Glu Ala
    130                 135                 140
Phe Leu Leu Thr Glu Gly Ser Xaa Lys Lys Lys Ser Val Lys Thr Val
145                 150                 155                 160
Asn Gln Leu Xaa Xaa Ala Leu His Xaa Asp Glu Gln Leu His Ala Xaa
                165                 170                 175
Ser Met Gly Ser Val Met Trp Pro Xaa Ser Xaa Cys Xaa Xaa Xaa Xaa
            180                 185                 190
Xaa Xaa Xaa Xaa Xaa Xaa Xaa Pro Gly Ile Asp Val Thr Thr Glu
        195                 200                 205
Leu Asp Thr Trp Ile Xaa Lys Ile Cys Leu Asp Ala Asp Val Phe Val
    210                 215                 220
Leu Xaa Gly Gln Leu Xaa Ser Pro Arg Cys Xaa Pro Xaa Asn Asn Xaa
225                 230                 235                 240
Phe His Lys Xaa Glu Xaa Asn Gly Phe Xaa Arg Ala Asn Ile Phe Ile
                245                 250                 255
Xaa Asn Asn Arg Trp Asp Ala Xaa Ala Xaa Xaa Xaa Xaa Tyr Met Glu
            260                 265                 270
Glu Val Arg Arg Gln His Met Glu Arg Cys Thr Ser Phe Leu Val Asp
        275                 280                 285
Glu Leu Gly Val Val Asp Arg Ala Gln Ala Gly Asp Arg Ile Phe Phe
    290                 295                 300
Val Ser Ala Lys Glu Val Leu Ser Ala Arg Val Gln Lys Ala Gln Gly
305                 310                 315                 320
Met Pro Glu Gly Gly Gly Ala Leu Ala Glu Gly Phe Gln Val Arg Met
                325                 330                 335
Xaa Xaa Xaa Xaa Xaa Xaa Xaa Xaa Xaa Xaa Xaa Cys Ile Ser Gln
            340                 345                 350
Ser Ala Val Lys Thr Lys Phe Glu Gln His Thr Val Arg Ala Lys Gln
        355                 360                 365
Ile Ala Glu Ala Gly Arg Leu Ile Met Asp Ser Leu His Ile Ala Ala
    370                 375                 380
Gln Glu Gln Arg Val Tyr Cys Leu Lys Met Arg Glu Glu Arg Gln Asp
385                 390                 395                 400
Arg Leu Arg Val Ile Asp Lys Gln Leu Glu Leu Leu Ala Xaa Asp Tyr
                405                 410                 415
Lys Leu Arg Ile Lys Xaa Ile Thr Xaa Xaa Xaa Xaa Xaa Xaa Xaa
            420                 425                 430
Xaa Xaa Xaa Xaa Xaa Xaa Xaa Xaa Xaa Xaa Xaa Xaa Xaa Xaa Xaa
        435                 440                 445
Xaa Xaa Xaa Xaa Xaa Xaa Xaa Xaa Xaa Xaa Xaa Xaa Xaa Xaa Xaa
    450                 455                 460
Xaa Xaa Leu His Arg His Ile Glu Glu Gly Leu Gly Arg Asn Leu Ser
465                 470                 475                 480
Asp Arg Cys Ser Thr Ala Ile Ala Ser Ser Leu Gln Thr Met Gln Gln
                485                 490                 495
Asp Met Ile Asp Gly Leu Lys Pro Leu Leu Pro Val Ser Met Arg Asn
            500                 505                 510
Gln Ile Asp Met Leu Val Pro Arg Gln Cys Phe Ser Leu Ser Tyr Asp
```

```
                515                 520                 525
Leu Asn Cys Asp Lys Leu Cys Ala Asp Phe Gln Glu Asp Ile Glu Phe
            530                 535                 540
His Phe Ser Leu Gly Trp Thr Met Leu Val Asn Arg Phe Leu Gly Pro
545                 550                 555                 560
Lys Asn Ser Arg Arg Ala Leu Leu Gly Tyr Ser Asp Gln Val Gln Arg
                565                 570                 575
Pro Leu Pro Leu Thr Pro Ala Asn Pro Ser Met Pro Pro Leu Xaa Gln
            580                 585                 590
Ser Phe Leu Thr Gln Glu Glu Leu Met Val Ser Met Val Thr Gly Leu
        595                 600                 605
Xaa Ser Leu Thr Ser Arg Thr Ser Met Gly Ile Leu Val Val Gly Xaa
    610                 615                 620
Xaa Val Trp Lys Ala Xaa Xaa Xaa Xaa Xaa Xaa Xaa Xaa Xaa Xaa Xaa
625                 630                 635                 640
Xaa Xaa Xaa Xaa Xaa Xaa Tyr Glu Arg Leu Thr Trp Thr Xaa Lys
                645                 650                 655
Ala Lys Glu Arg Ala Phe Lys Arg Gln Phe Val Glu Tyr Ala Ser Glu
            660                 665                 670
Lys Leu Gln Leu Ile Ile Xaa Tyr Thr Gly Ser Asn Cys Ser His Gln
        675                 680                 685
Val Gln Gln Glu Leu Ser Gly Thr Phe Ala His Leu Cys Gln Gln Val
    690                 695                 700
Asp Ile Thr Arg Asp Asn Leu Glu Gln Glu Ile Ala Ala Met Asn Lys
705                 710                 715                 720
Lys Val Glu Ala Leu Asp Ser Leu Gln Ser Arg Ala Xaa Leu Leu Arg
                725                 730                 735
Asn Lys Ala Gly Trp Leu Asp Ser Glu Leu Asn Met Phe Thr His Gln
            740                 745                 750
Tyr Leu Gln Pro Ser Arg
        755

<210> SEQ ID NO 17
<211> LENGTH: 1986
<212> TYPE: DNA
<213> ORGANISM: R. rattus

<400> SEQUENCE: 17
atgaaggtgg cttttttggg ccggacgagc aatgggaaga gcaccgtgat caatgccatg      60
ctttgggaca agttctgcc atctgggatt ggccacacca ccaattgctt cctgcgggtt     120 ggggcacgg atggccacga ggccttcctc ctcacggagg ctcagaaga gaagaagagt     180 gtcaagaccg tgaaccagct agcccatgcc ctccatcagg atgagcagct gcatgcaggc     240
agcctggtga gtgtgatgtg gcccaactcc aagtgtccac ttctgaagga tgacctcgtg     300
ctgatggaca gccctgggat cgatgtcacc acggagctgg acagctggat tgataagttt     360
tgcctggatg ctgatgtgtt tgtactggtg gccaactcag agtccacgct gatgcagacg     420
gagaagcagt tcttccacaa agtgagtgag cgtctctccc ggcccaacat cttcatcctg     480
aacaaccgct gggatgcgtc tgcctcggag cctgagtaca tggaggaggt gcggcggcag     540
cacatggaac gctgcaccag ctttctggtg atgagctag gcgtggtgga tcgagctcag     600
gccggggacc ggatcttctt tgtgtctgcc aaggaggtgc tcagtgccag ggtccagaaa     660
gcccagggca tgccagaagg aggtggcgct cttgcagaag ttttcaagt gaggatgttt     720
```

```
gagtttcaga atttcgagag gcgatttgag gagtgcattt cccagtctgc agtaaagacc    780
aaatttgagc agcacacagt ccgggccaag cagattgcag aggccgtccg tctcatcatg    840
gattccctgc acattgcggc tcaggagcag cgggtttatt gtcttgaaat gcgggaagag    900
cggcaagacc ggctgagatt cattgacaag cagctggagc tcctggctca agactataag    960
ctacggatta agcagatgac agaggaagtg gaaaggcagg tgtccacagc catggctgaa   1020
gagatcaggc gcctctctgt gctggttgac gagtaccaga tggactttca cccatcccca   1080
gttgtcctca aggtttataa gaatgaactg caccgccata tagaggaagg cctgggacga   1140
aacatgtctg accgctgctc cacagccatt gccagttcac tgcagactat gcagcaagac   1200
atgatagacg gcttgaagcc ccttcttcct gtgtctgtgc ggaatcagat agacatgctg   1260
gtccctcgac agtgtttctc cctcagctat gacctgaact gtgacaagct gtgcgctgac   1320
tttcaggagg acatcgaatt ccatttctcc cttggatgga ctatgctagt gaataggttc   1380
ctgggcccta agaatagccg gcgggccttg ctgggctaca atgatcaggt tcagcgtcct   1440
ctccctctga cacctgccaa ccccagcatg ccacccttgc cacagggctc cctcacccag   1500
gaggagctca tggtctccat ggttactggc ctggcctctc tgacttccag gacctctatg   1560
ggcattctcg tggtcggagg agtggtgtgg aaggcagtgg gctggagact catcgccctc   1620
tcctttggac tgtatggcct cctgtacgtg tatgagcggc tgacctggac caccagagcc   1680
aaggagaggg ccttcaagcg ccagtttgtg gagtatgcca gtgagaagct gcagctcatt   1740
atcagttata ccggctctaa ctgcagccac caagttcagc aagaattgtc tgggacattt   1800
gctcatctgt gccagcaagt tgacatcacc cgggataatc tggagcagga aattgctgcc   1860
atgaacaaga aagttgaggc tctggattca cttcagagca aagccaaatt gctcaggaat   1920
aaagctggct ggttggacag cgaactcaac atgttcatac accagtacct gcagcccggc   1980
agatag                                                              1986

210> SEQ ID NO 18
<211> LENGTH: 134
<212> TYPE: PRT
<213> ORGANISM: C. saccharolytica

<400> SEQUENCE: 18

Ala Gly Ser Ile Lys Glu Lys Ile Glu Lys Asn Ala Phe Tyr Leu Val
 1               5                  10                  15

Val Leu Gly Gln Phe Lys Arg Gly Lys Ser Thr Leu Ile Asn Tyr Met
            20                  25                  30

Leu Gly Ala Asn Leu Leu Pro Thr Gly Val Leu Pro Leu Thr Ser Val
        35                  40                  45

Ile Thr Lys Ile Tyr Leu Asn Lys Asp Val Val Ile Val Asp Thr Pro
    50                  55                  60

Gly Ile Gly Ser Val Tyr Gln His Asn Thr Asp Val Thr Tyr Glu Phe
 65                  70                  75                  80

Ile Asp Lys Ser Asp Ala Val Val Phe Val Leu Ser Val Asp Pro Pro
                85                  90                  95

Ile Thr Phe Val Glu Lys Gln Phe Leu Leu Lys Ile Ala Glu Asn Val
            100                 105                 110

Asp Lys Ile Phe Phe Val Ile Asn Lys Ser Asp Leu Thr Ser Lys Asn
        115                 120                 125

Glu Ile Glu Lys Ile Val
    130
```

<210> SEQ ID NO 19
<211> LENGTH: 157
<212> TYPE: PRT
<213> ORGANISM: S. cerevisaie

<400> SEQUENCE: 19

```
Val Thr Asn His Leu Asn Ala Leu Lys Arg Val Asp Asp Val Ser
 1               5                  10                  15

Ser Lys Val Phe Ile Thr Gly Asp Val Asn Thr Gly Lys Ser Ala Leu
                20                  25                  30

Cys Asn Ser Leu Leu Lys Gln Arg Leu Leu Pro Glu Asp Gln Leu Pro
            35                  40                  45

Cys Thr Asn Val Phe Ser Glu Ile Leu Leu Lys Ile Tyr Ile Lys Asp
    50                  55                  60

Asp Lys Arg Pro Ala Ser Thr Ser Leu Leu Arg Asn Gly Thr Val Asp
65                  70                  75                  80

Ile Ser Leu Ile Asp Ser Pro Gly Leu Asn Met Asp Ser Leu Gln Thr
                85                  90                  95

Ala Glu Val Met Ser Arg Gln Glu Ile Asp Leu Val Ile Phe Val
                100                 105                 110

Val Asn Ala Glu Asn Gln Leu Thr Leu Ser Ala Glu Phe Ile Ser Leu
            115                 120                 125

Ala Ser Arg Glu Lys Lys Leu Met Phe Phe Val Val Lys Lys Phe Asp
    130                 135                 140

Lys Ile Arg Asp Lys Gln Arg Cys Lys Glu Leu Ile Leu
145                 150                 155
```

<210> SEQ ID NO 20
<211> LENGTH: 163
<212> TYPE: PRT
<213> ORGANISM: C. elegans
<220> FEATURE:
<221> NAME/KEY: VARIANT
<222> LOCATION: (1)...(163)
<223> OTHER INFORMATION: Xaa = Any Amino Acid

<400> SEQUENCE: 20

```
Ile Gly Asp Ser Ile Lys Thr Ile Met Asp Thr Phe Gln Arg Asp Asn
 1               5                  10                  15

Met Lys Val Val Phe Phe Gly Arg Thr Ser Asn Gly Lys Ser Thr Thr
                20                  25                  30

Ile Asn Ala Met Leu His Glu Lys Val Leu Pro Gln Gly Met Gly His
            35                  40                  45

Thr Thr Cys Cys Phe Leu Gln Val Leu Lys Val Phe His Pro Lys Lys
    50                  55                  60

Ser Glu Ser Gly Glu Cys Arg Leu Leu Gln Asn Asp Val Val Ile Leu
65                  70                  75                  80

Asp Ser Pro Gly Val Asp Leu Ser Pro Glu Phe Asp Ser Trp Ile Asp
                85                  90                  95

Xaa His Cys Arg Asp Ala Asp Val Phe Leu Val Ser Asn Ala Glu Ser
                100                 105                 110

Thr Leu Thr Gln Ala Phe Lys Asn Phe Phe Leu Arg Val Ala Lys Lys
            115                 120                 125

Leu Ser Lys Pro Val Phe Ile Leu Asn Asn Arg Trp Asp Ala Ser Ala
    130                 135                 140

Ala Glu Thr Glu Asn Ile Glu Asp Val Lys Lys Gln His Leu Thr Arg
145                 150                 155                 160
```

Phe Arg Gln

<210> SEQ ID NO 21
<211> LENGTH: 18
<212> TYPE: PRT
<213> ORGANISM: Artificial Sequence
<220> FEATURE:
<223> OTHER INFORMATION: consensus

<400> SEQUENCE: 21

Met Val Ala Phe Phe Gly Arg Thr Ser Asn Gly Lys Ser Thr Val Ile
1               5                   10                  15

Asn Ala

<210> SEQ ID NO 22
<211> LENGTH: 18
<212> TYPE: PRT
<213> ORGANISM: Artificial Sequence
<220> FEATURE:
<223> OTHER INFORMATION: consensus

<400> SEQUENCE: 22

Met Val Ala Phe Phe Leu Arg Thr Ser Asn Gly Lys Ser His Val Ile
1               5                   10                  15

Asn Ala

<210> SEQ ID NO 23
<211> LENGTH: 18
<212> TYPE: PRT
<213> ORGANISM: Artificial Sequence
<220> FEATURE:
<223> OTHER INFORMATION: consensus

<400> SEQUENCE: 23

Met Val Ala Phe Lys Leu Arg His Ser Asn Pro Lys Ser His Val Ile
1               5                   10                  15

Asn Ala

<210> SEQ ID NO 24
<211> LENGTH: 16
<212> TYPE: PRT
<213> ORGANISM: Artificial Sequence
<220> FEATURE:
<223> OTHER INFORMATION: consensus

<400> SEQUENCE: 24

Met Val Ala Phe Phe Arg Thr Ser Asn Gly Ser Thr Val Ile Asn Ala
1               5                   10                  15

<210> SEQ ID NO 25
<211> LENGTH: 27
<212> TYPE: DNA
<213> ORGANISM: Droshphila melanogaster

<400> SEQUENCE: 25
acctcaaatg gaactagtgc cgtgatc                                      27

<210> SEQ ID NO 26
<211> LENGTH: 23
<212> TYPE: DNA
<213> ORGANISM: Droshphila melanogaster

<400> SEQUENCE: 26

```
tactcaacaa tctatgggat aag                                              23
```

<210> SEQ ID NO 27
<211> LENGTH: 29
<212> TYPE: DNA
<213> ORGANISM: Homo sapiens

<400> SEQUENCE: 27

```
gactctagaa tgtccctgct cttctctcg                                        29
```

<210> SEQ ID NO 28
<211> LENGTH: 24
<212> TYPE: DNA
<213> ORGANISM: Homo sapiens

<400> SEQUENCE: 28

```
gcccactatc tgctgggctg cagg                                             24
```

<210> SEQ ID NO 29
<211> LENGTH: 16
<212> TYPE: PRT
<213> ORGANISM: Artificial Sequence
<220> FEATURE:
<223> OTHER INFORMATION: linker

<400> SEQUENCE: 29

```
Ile Leu Gln Ser Thr Val Pro Arg Ala Arg Asp Pro Pro Val Ala Thr
 1               5                  10                  15
```

<210> SEQ ID NO 30
<211> LENGTH: 19
<212> TYPE: PRT
<213> ORGANISM: Artificial Sequence
<220> FEATURE:
<223> OTHER INFORMATION: consensus

<400> SEQUENCE: 30

```
Met Lys Val Ala Phe Phe Gly Arg Thr Ser Asn Gly Lys Ser Thr Val
 1               5                  10                  15

Ile Asn Ala
```

<210> SEQ ID NO 31
<211> LENGTH: 19
<212> TYPE: PRT
<213> ORGANISM: Artificial Sequence
<220> FEATURE:
<223> OTHER INFORMATION: consensus

<400> SEQUENCE: 31

```
Met Lys Val Ala Phe Phe Gly Arg Thr Ser Asn Gly Lys Ser Ala Val
 1               5                  10                  15

Ile Asn Ala
```

<210> SEQ ID NO 32
<211> LENGTH: 19
<212> TYPE: PRT
<213> ORGANISM: Artificial Sequence
<220> FEATURE:
<223> OTHER INFORMATION: consensus

<400> SEQUENCE: 32

```
Met Lys Val Val Phe Phe Gly Arg Thr Ser Asn Gly Lys Ser Thr Thr
 1               5                  10                  15

Ile Asn Ala
```

<210> SEQ ID NO 33
<211> LENGTH: 19
<212> TYPE: PRT
<213> ORGANISM: Artificial Sequence
<220> FEATURE:
<223> OTHER INFORMATION: consensus

<400> SEQUENCE: 33

Met Lys Val Ala Phe Phe Gly Arg Thr Ser Ser Gly Lys Ser Thr Val
 1               5                  10                  15

Ile Asn Ala

<210> SEQ ID NO 34
<211> LENGTH: 19
<212> TYPE: PRT
<213> ORGANISM: Artificial Sequence
<220> FEATURE:
<223> OTHER INFORMATION: consensus

<400> SEQUENCE: 34

Met Lys Val Ala Phe Phe Gly Arg Thr Ser Asn Gly Lys Ser Thr Val
 1               5                  10                  15

Ile Asn Ala

<210> SEQ ID NO 35
<211> LENGTH: 17
<212> TYPE: PRT
<213> ORGANISM: Artificial Sequence
<220> FEATURE:
<223> OTHER INFORMATION: consensus

<400> SEQUENCE: 35

Asp Leu Val Leu Met Asp Ser Pro Gly Thr Asp Val Thr Thr Glu Leu
 1               5                  10                  15

Asp

<210> SEQ ID NO 36
<211> LENGTH: 17
<212> TYPE: PRT
<213> ORGANISM: Artificial Sequence
<220> FEATURE:
<223> OTHER INFORMATION: consensus

<400> SEQUENCE: 36

Asp Val Val Leu Met Asp Thr Pro Gly Val Asp Val Thr Ala Gln Leu
 1               5                  10                  15

Asp

<210> SEQ ID NO 37
<211> LENGTH: 17
<212> TYPE: PRT
<213> ORGANISM: Artificial Sequence
<220> FEATURE:
<223> OTHER INFORMATION: consensus

<400> SEQUENCE: 37

Asp Val Val Ile Leu Asp Ser Pro Gly Val Asp Leu Ser Pro Glu Phe
 1               5                  10                  15

Asp

<210> SEQ ID NO 38
<211> LENGTH: 17

```
<212> TYPE: PRT
<213> ORGANISM: Artificial Sequence
<220> FEATURE:
<223> OTHER INFORMATION: consensus

<400> SEQUENCE: 38

Asp Leu Val Leu Val Asp Ser Pro Gly Thr Asp Val Thr Thr Glu Leu
 1               5                  10                  15
Asp

<210> SEQ ID NO 39
<211> LENGTH: 17
<212> TYPE: PRT
<213> ORGANISM: Artificial Sequence
<220> FEATURE:
<223> OTHER INFORMATION: consensus

<400> SEQUENCE: 39

Asp Leu Val Leu Met Asp Ser Pro Gly Thr Asp Val Thr Thr Glu Leu
 1               5                  10                  15
Asp

<210> SEQ ID NO 40
<211> LENGTH: 15
<212> TYPE: PRT
<213> ORGANISM: Artificial Sequence
<220> FEATURE:
<223> OTHER INFORMATION: consensus

<400> SEQUENCE: 40

Pro Asn Ile Phe Ile Leu Asn Asn Arg Trp Asp Ala Ser Ala Ser
 1               5                  10                  15

<210> SEQ ID NO 41
<211> LENGTH: 15
<212> TYPE: PRT
<213> ORGANISM: Artificial Sequence
<220> FEATURE:
<223> OTHER INFORMATION: consensus

<400> SEQUENCE: 41

Pro Asn Leu Phe Ile Leu Asn Asn Arg Trp Asp Lys Ala Ser Ser
 1               5                  10                  15

<210> SEQ ID NO 42
<211> LENGTH: 15
<212> TYPE: PRT
<213> ORGANISM: Artificial Sequence
<220> FEATURE:
<223> OTHER INFORMATION: consensus

<400> SEQUENCE: 42

Pro Asn Val Phe Ile Leu Asn Asn Arg Trp Asp Ala Ser Ala Ala
 1               5                  10                  15

<210> SEQ ID NO 43
<211> LENGTH: 15
<212> TYPE: PRT
<213> ORGANISM: Artificial Sequence
<220> FEATURE:
<223> OTHER INFORMATION: consensus

<400> SEQUENCE: 43

Pro Asn Ile Phe Ile Leu Asn Asn Arg Trp Asp Ala Ser Ala Ser
 1               5                  10                  15
```

```
<210> SEQ ID NO 44
<211> LENGTH: 15
<212> TYPE: PRT
<213> ORGANISM: Artificial Sequence
<220> FEATURE:
<223> OTHER INFORMATION: consensus

<400> SEQUENCE: 44

Pro Asn Ile Phe Ile Leu Asn Asn Arg Trp Asp Ala Ser Ala Ser
 1               5                  10                  15

<210> SEQ ID NO 45
<211> LENGTH: 18
<212> TYPE: PRT
<213> ORGANISM: Homo sapiens

<400> SEQUENCE: 45

Ile Ile Val Gly Gly Val Ile Trp Lys Thr Ile Gly Trp Lys Leu Leu
 1               5                  10                  15

Ser Val

<210> SEQ ID NO 46
<211> LENGTH: 18
<212> TYPE: PRT
<213> ORGANISM: Homo sapiens

<400> SEQUENCE: 46

Leu Val Val Gly Gly Val Val Trp Lys Ala Val Gly Trp Arg Leu Ile
 1               5                  10                  15

Ala Leu
```